US010197557B2

(12) United States Patent
Cruz et al.

(10) Patent No.: US 10,197,557 B2
(45) Date of Patent: Feb. 5, 2019

(54) SMALL MOLECULES FOR ENDOTHELIAL CELL ACTIVATION

(75) Inventors: Daniel Cruz, Los Angeles, CA (US); Ohyun Kwon, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 554 days.

(21) Appl. No.: 13/981,912

(22) PCT Filed: Feb. 23, 2012

(86) PCT No.: PCT/US2012/026322
§ 371 (c)(1),
(2), (4) Date: Jul. 25, 2013

(87) PCT Pub. No.: WO2012/116181
PCT Pub. Date: Aug. 30, 2012

(65) Prior Publication Data
US 2013/0310417 A1    Nov. 21, 2013

Related U.S. Application Data

(60) Provisional application No. 61/446,466, filed on Feb. 24, 2011.

(51) Int. Cl.
C07D 207/48      (2006.01)
C07D 471/04      (2006.01)
C07D 487/04      (2006.01)
G01N 33/50       (2006.01)

(52) U.S. Cl.
CPC ....... G01N 33/5044 (2013.01); C07D 207/48 (2013.01); C07D 471/04 (2013.01); C07D 487/04 (2013.01); G01N 33/5047 (2013.01); G01N 33/5064 (2013.01)

(58) Field of Classification Search
None
See application file for complete search history.

(56) References Cited

U.S. PATENT DOCUMENTS

| 3,557,100 A | 1/1971 | Freed et al. ............... 546/81 |
| 2009/0124609 A1 | 5/2009 | Albrecht et al. ........ 514/230.5 |
| 2010/0279277 A1 | 11/2010 | Warren et al. |

FOREIGN PATENT DOCUMENTS

| WO | WO 2007059108 | 5/2007 |
| WO | WO2007/111948 | * 10/2007 |
| WO | WO 2008124083 | 10/2008 |

OTHER PUBLICATIONS

Wang et al. Chem. Eur. J., 2011, vol. 17, pp. 649-654, published online Nov. 9, 2010.*
Pandey, M. K. et al., 2009, "Design, synthesis and anti-inflammatory evaluation of PEGylated 4-methyl and 4,8-dimethylcoumarins," European Journal of Pharmaceutical sciences, 39(1-3): 134-140.
Kasama, T. et al., 2002, "Interaction of monocytes with vascular endothelial cells synergistically induces interferon γ inducible protein 10 expression through activation of specific cell surface molecules and cytokines," Cellular Immunology, 219(2): 131-139.
Starickova, E. A. et al., 2010, "Changes in the profiles of chemokines secreted by endothelial cells and monocytes under different coculturing conditions," Immunology and microbiology, 150(10): 446-449.
Cruz, D. et al., 2011, "Diversity through phosphine catalysis identifies octahydro-1,6-naphthyridin-4-ones as activators of endothelium-driven immunity," PNAS, 108(17): 6769-6774.
International Search Report for PCT/US2012/026322, 7 pages.
Extended European Search Report for EP 15177218.3, dated Sep. 17, 2015.
Wang et al., Chem. Eur. J. 17:649-654, 2011.

* cited by examiner

Primary Examiner — Savitha M Rao
Assistant Examiner — Gregg Polansky
(74) Attorney, Agent, or Firm — Norton Rose Fulbright US LLP

(57) ABSTRACT

The present invention provides small molecules for endothelial cell activation and compositions thereof and methods of making and using the same.

7 Claims, 15 Drawing Sheets

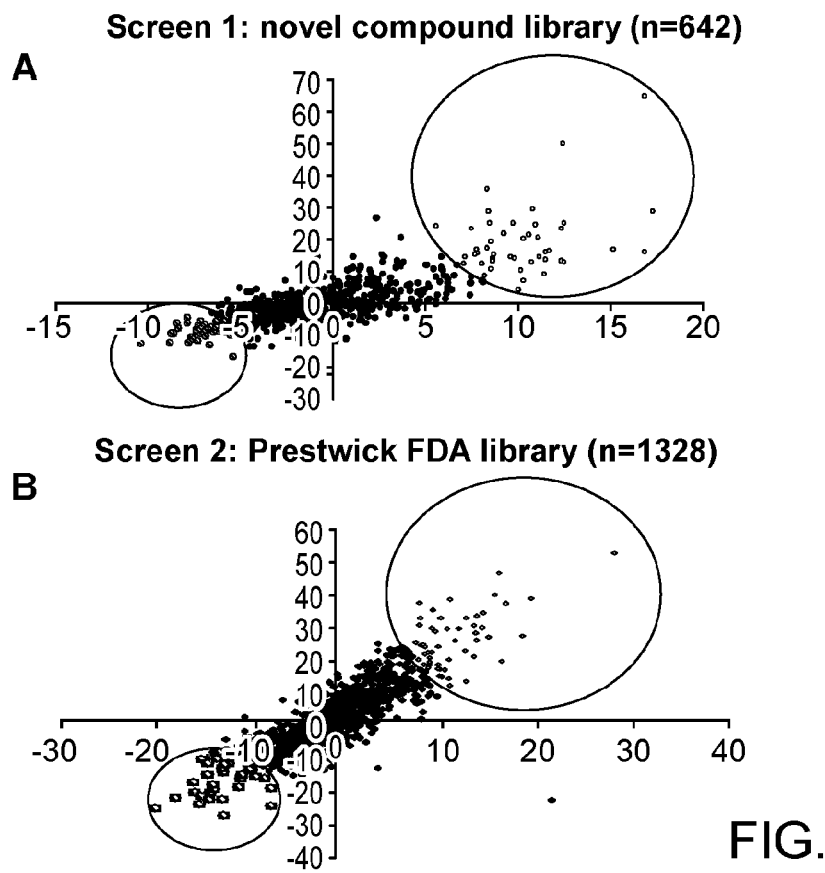
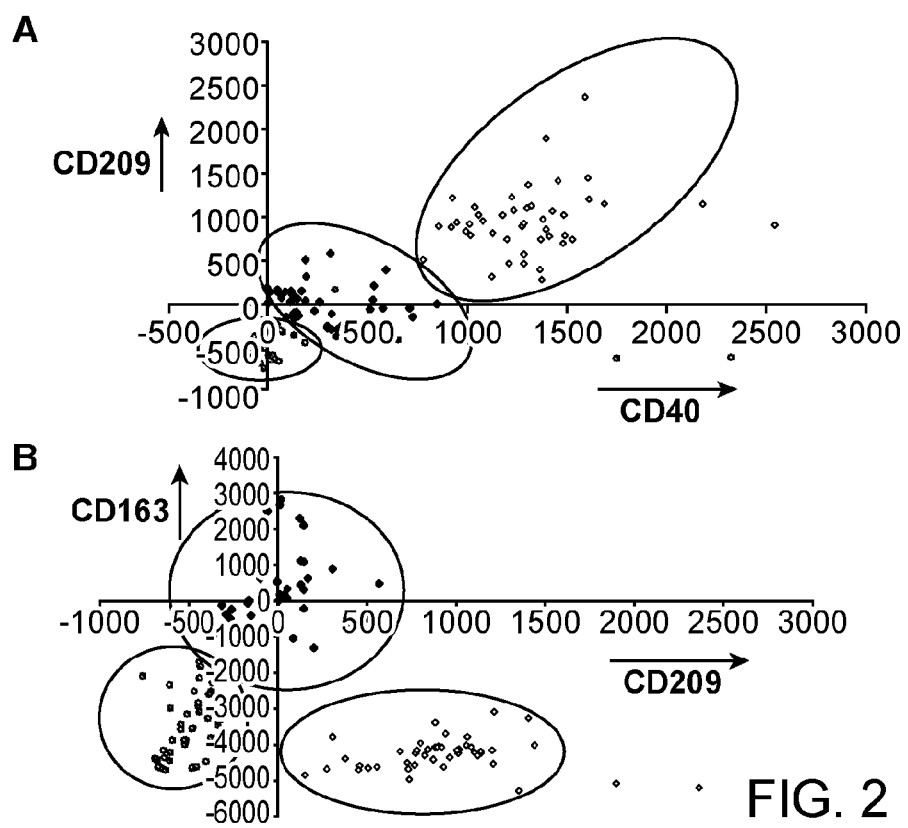
FIG. 1
FIG. 2

*N6*-benzene ring is required; benzene ring without a substituent is OK.
*Para*-methyl and chloro are good.
*Meta*-methyl and chloro are good.
*Ortho*-methyl shows varying results, but chloro is OK.

*C2*-benzene ring (without a substituent) and 2-thiophenyl are OK; 1-naphthyl group is not.
*Para*-methyl, chloro, bromo and ethyl group show varying results; methoxy group is bad.
*Meta*-methyl is OK, but chloro is not.
*Ortho*-methyl and fluoro are bad; chloro is OK.

*N1*-benzene ring is required and benzene ring itself is not enough (except 105A5).
*Para*-methyl, chloro, or bromo is necessary.
*Meta*-methyl is not good and chloro is OK.
*Ortho*-methyl shows varying results; nitro is bad and chloro is OK.

*C7*-benzene ring is not necessary,
but 1-naphthyl group abates activity
*Para*-methyl or methoxy is OK; chloro and ethyl group show varying results.
*Meta*-methyl is OK, but chloro is not.
*Ortho*-methyl or chloro is OK; fluoro shows varying results.

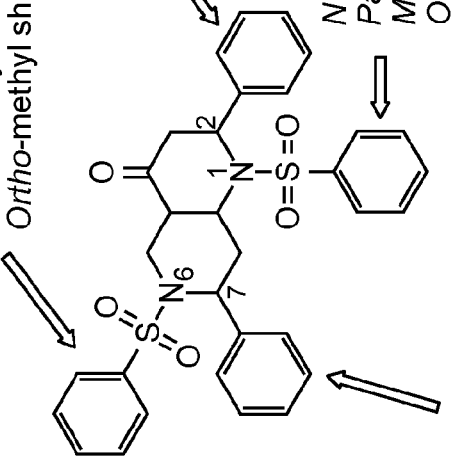

FIG. 7

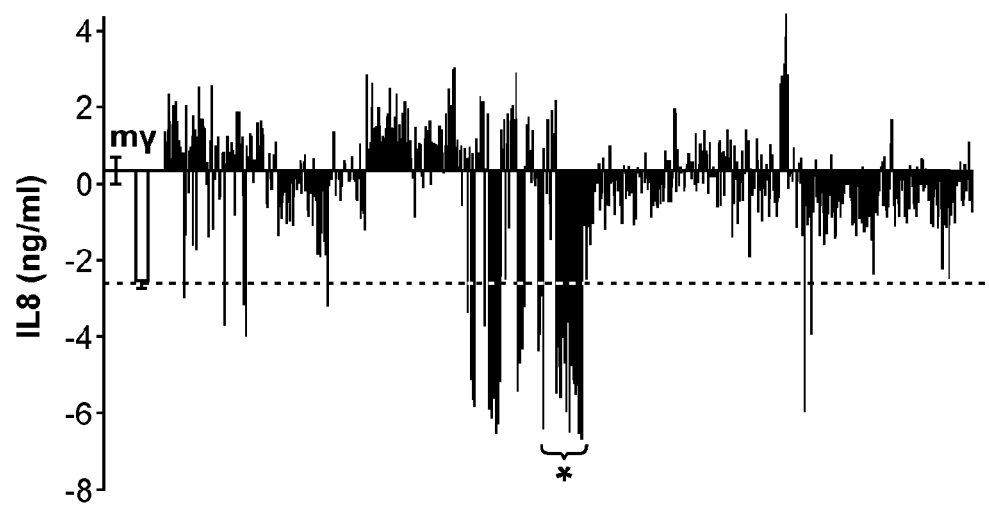
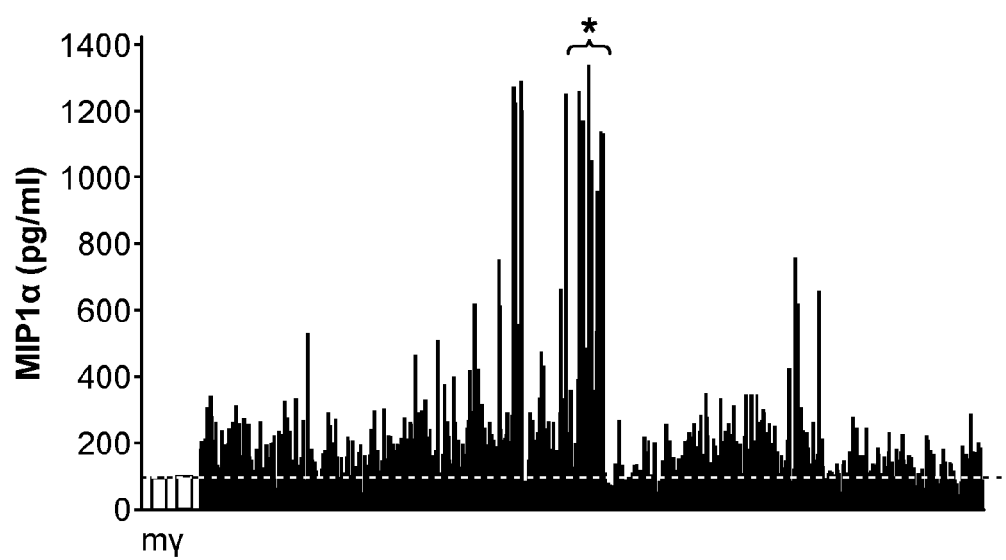
FIG. 10

A
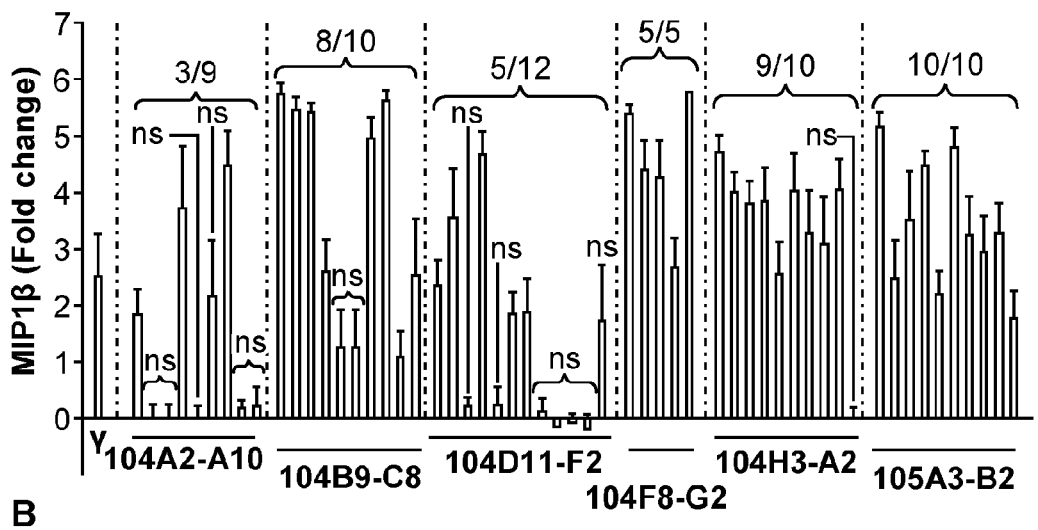
B
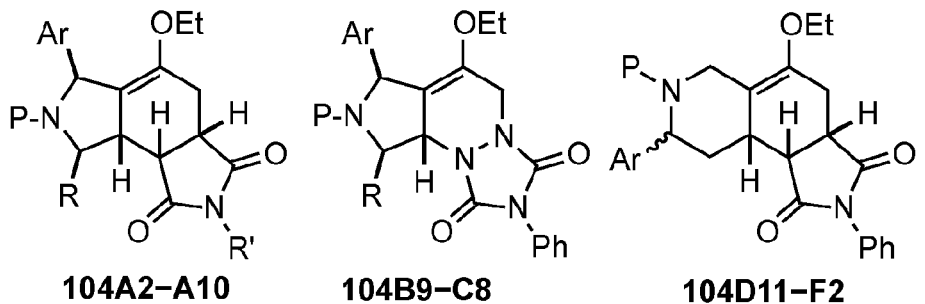
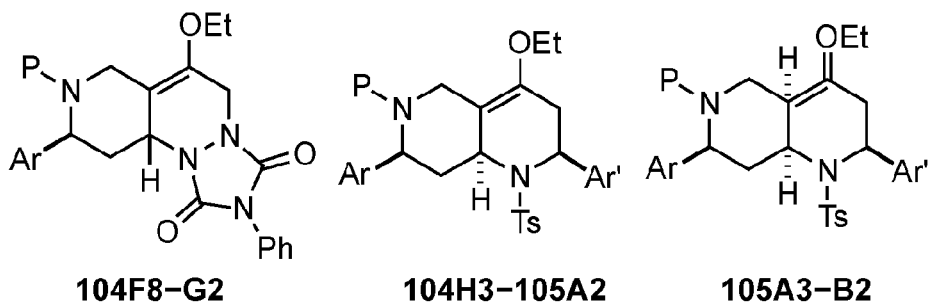
Ar = phenyl, 4-MeC$_6$H$_4$, 4-EtC$_6$H$_4$, 4-ClC$_6$H$_4$, 3-ClC$_6$H$_4$, 2-thiophenyl, 1-naphthyl
P = tosyl, benzenesulfonyl
R = H, isopropyl, *n*-pentyl, *t*-butyl, phenyl
R' = phenyl, ethyl, benzyl
Ar' = phenyl, 4-EtC$_6$H$_4$, 4-ClC$_6$H$_4$, 2-thiophenyl
FIG. 11

SMALL MOLECULES FOR ENDOTHELIAL CELL ACTIVATION

CROSS-REFERENCE TO RELATED APPLICATIONS

This application is a national stage entry of International Application No. PCT/US12/26322 filed on Feb. 23, 2012, which in turn claims the benefit of U.S. Provisional Patent Application No. 61/446,466, filed Feb. 24, 2011, the teaching of each of which is incorporated herein by reference in its entirety.

STATEMENT AS TO RIGHTS TO INVENTIONS MADE UNDER FEDERALLY SPONSORED RESEARCH AND DEVELOPMENT

This invention was made with Government support under Grant Nos. GM071779, GM081282, HL092290, NS035322, and NS052528, awarded by the National Institutes of Health. The Government has certain rights in the invention.

FIELD OF THE INVENTION

The invention provides small molecules for endothelial cell activation and compositions thereof and methods of making and using the same.

BACKGROUND OF THE INVENTION

The endothelium plays a critical role in promoting inflammation in cardiovascular disease and other chronic inflammatory conditions, and many small molecule screens have sought to identify agents that prevent endothelial cell activation. Conversely, an augmented immune response can be protective against microbial pathogens and in cancer immunotherapy. Yet, small molecule screens to identify agents that induce endothelial cell activation have not been reported. Small molecules for endothelial cell activation are thus limited.

On the other hand, to interrogate small molecule libraries, high-throughput screening (HTS) systems that detect compounds with pre-specified molecular targets have been developed. However, a limitation of most current screens is that they do not integrate the interactions that occur between heterogeneous cell types involved in disease pathogenesis-they are a severe oversimplification. This has resulted in a conceptual shift towards "systems biology" approaches, which, because of their increased complexity, are more difficult to automate for HTS. Therefore, a significant need exists for screening systems that can link a compound's molecular structure with biological function and gene expression in adequately complex systems.

The embodiments described below address the above mentioned issues and problems.

SUMMARY OF THE INVENTION

In one aspect of the present invention, it is provided a biological assay that detects a compound's capacity to perturb immune responses along a conserved spectrum of pro- and anti-inflammatory immune responses. The assay comprises:

co-culturing a plurality of endothelial cells (EC) and a plurality of monocytes in a culture, and designating the compound as pro-inflammatory if co-culturing results in chemokine production in the culture or as anti-inflammatory if co-culturing results in reduction of chemokine production in the culture;

wherein the endothelial cells are treated by the compound prior to co-culturing.

In some embodiments of the assay, the designating step comprises performing MIP1α and/or MIP1β expression analysis on a sample of supernatant of the culture.

In some embodiments of the assay, in combination with any of the above embodiments, the endothelial cells are harvested for flow cytometry, wherein the monocytes (e.g., human monocytes) are labeled with CD40, CD209, and CD163.

In some embodiments of the assay, in combination with any of the above embodiments, the flow cytometry comprises Parameters 1-10, where:

Parameter 1 comprises Gate on EC/monocytes using FSC vs SSC on whole co-culture population;

Parameter 2 comprises using SSC vs. CD40 to separate monocytes from EC where loss of EC population reflects compound toxicity;

Parameter 3 comprises Gate on CD40+ monocytes;

Parameter 4 comprises determining CD40 MFI on CD40+ macrophages;

Parameter 5 comprises determining CD209 MFI on CD40+ macrophages;

Parameter 6 comprises determining CD163 MFI on CD40+ macrophages;

Parameter 7 comprises subtracting vehicle control MFIs from each sample of interest;

Parameter 8 comprises scatter plot of CD40 vs CD209;

Parameter 9 comprises plot CD209 (or) CD40 vs. CD163 to further separate cell populations; and Parameter 10 comprises using the MIP1α and/or MIP1β expression analysis to corroborate pro- or anti-inflammatory effects wherein pro-inflammatory compounds promote EC-triggered innate immune activation, while anti-inflammatory compounds inhibit EC-triggered innate immune activation.

In another aspect of the present invention, it is provided a compound determined by the assay according to the various embodiments above as pro-inflammatory or as anti-inflammatory.

In another aspect of the present invention, it is provided a pro-inflammatory compound effective for augmenting innate immune responses in a mammal, wherein the compound is octahydro-1,6-naphthyridin-4-one or an analog thereof, a pharmaceutically acceptable salt thereof, or prodrug thereof.

In another aspect of the present invention, it is provided a composition comprising the pro-inflammatory compound effective for augmenting innate immune responses in a mammal, wherein the compound is octahydro-1,6-naphthyridin-4-one or an analog thereof, a pharmaceutically acceptable salt thereof, or prodrug thereof.

In another aspect of the present invention, it is provided a method of treating or ameliorating a medical condition, comprising administering to a patient in need thereof a pro-inflammatory compound effective for augmenting innate immune responses in a mammal, wherein the compound is octahydro-1,6-naphthyridin-4-one or an analog thereof, a pharmaceutically acceptable salt thereof, or prodrug thereof.

In some embodiments of the method, the compound is in an effective amount for the medical condition included in a composition.

In some further embodiments of the method, in combination with any of the above embodiments, the medical condition is cancer or a disease caused by a microbial pathogen.

In a further aspect of the present invention, it is provided a method of preparing an octahydro-1,6-naphthyridin-4-one compound or analog. The method comprises:

forming an enol ether intermediate via phosphine-catalyzed [4+2] annulation of an allenoate with a first imine building block followed by treatment with Tebbe reagent and anhydrous pyridine to form an enol ether intermediate, subjecting the enol ether intermediate to endo-selective Diels-Alder reaction with a second imine building block to yield an octahydro-1,6-naphthyridine interminate, and forming the octahydro-1,6-naphthyridine-4-one compound or analog.

In some embodiments of the method, the allenoate is formed by coupling a Wang resin having reactive hydroxyl groups with 2-methyl-2,3-butadienoic acid, and wherein the method is solid phase synthesis.

In some embodiments of the method, in combination with any of the above embodiments, the solid phase synthesis is carried out via combinatorial library construction.

In some embodiments of the method, in combination with any of the above embodiments, the solid support comprises Synphase lanterns wherein the first imine building block is encoded by tagging individual lanterns.

BRIEF DESCRIPTION OF THE DRAWINGS

FIGS. 1A and 1B show results of screens of invention on small molecule libraries. A. A library with no FDA approved compounds. B. Prestwick library of FDA approved compounds.

FIGS. 2A and 2B show data from 384-well plate of EC treated with IFNγ (n=44), DMSO (n=44) or TGFβ (n=44). A: differences in CD209 and CD40 MFI are plotted as described in Parameter "h". TGFβ (anti-inflammatory control), DMSO control, IFNγ (pro-inflammatory control). B: Same data as in the top (FIG. 2A), except the populations are further stratified by comparing CD163 vs. CD209 expression on EC-triggered CD40+ MF.

FIG. 7 shows structure-activity relationship (SAR) analysis of octahydro-1,6-naphthyridin-4-ones.

FIG. 10 shows identification of small molecules that activate human endothelial cells. IFNγ (10 ng/ml) and DMSO controls (n=60 total replicates) and 642 compounds (10 μM) were tested for their ability to promote (A) IL8 and (B) MIP1α production. For IL8, data is expressed as change in expression in comparison to DMSO. Dashed line represents the level for IFNγ-treated EC-PBMC co-culture. For MIP1α, DMSO and IFNγ-treated EC triggered comparable levels.

FIGS. 11A and 11B show validation of the seven scaffolds accounting for the majority of EC activating compounds. (A) After the initial screen, the six subfamilies (hits and non-hits) were repeated in two independent experiments. Data represents mean±s.e.m. for MIP1β fold-induction over DMSO control for all three experiments. To account for experimental variability, all individual data points were log base 2 transformed. Number of family members which were significantly induced over DMSO (p<0.05) is shown above each family of compounds. (B) The general structures of the seven families of EC-activating compounds.

Figure 12:
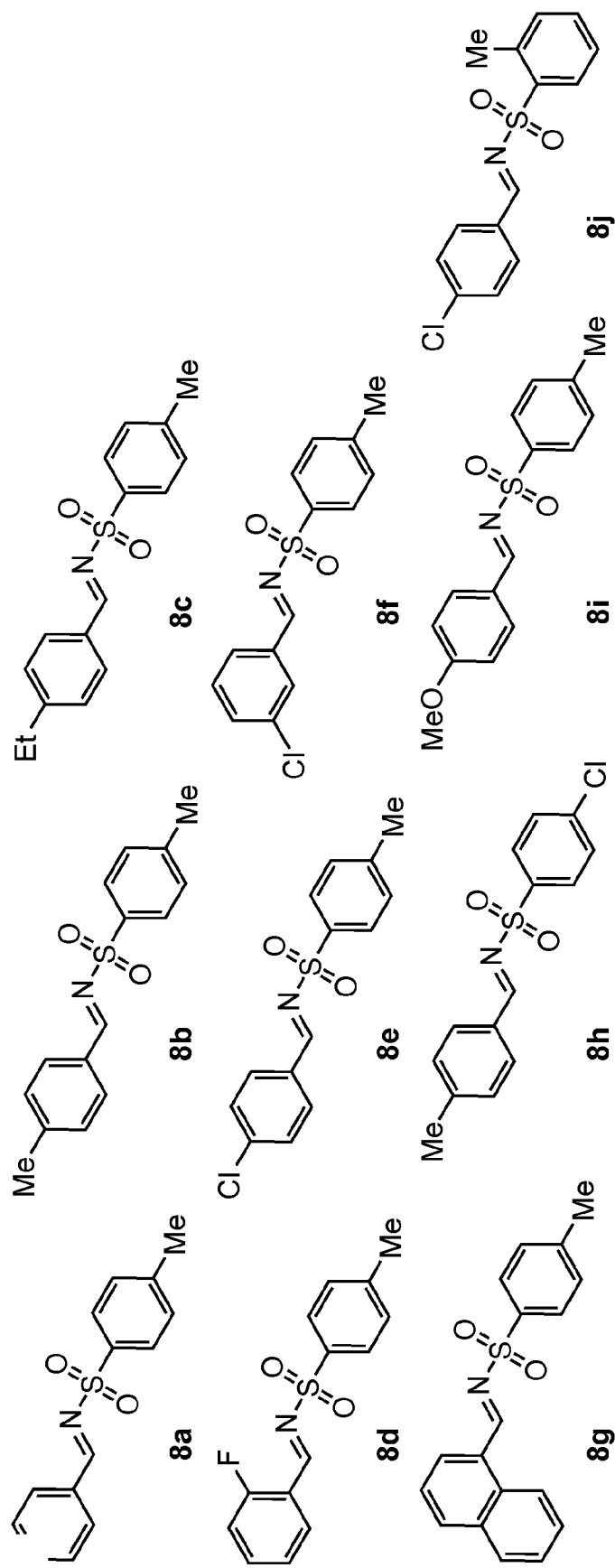

FIG. 12 shows ten N-sulfonylimine building blocks for the solid-phase octahydro-1,6-naphthyridin-4-one library.

Figure 13:
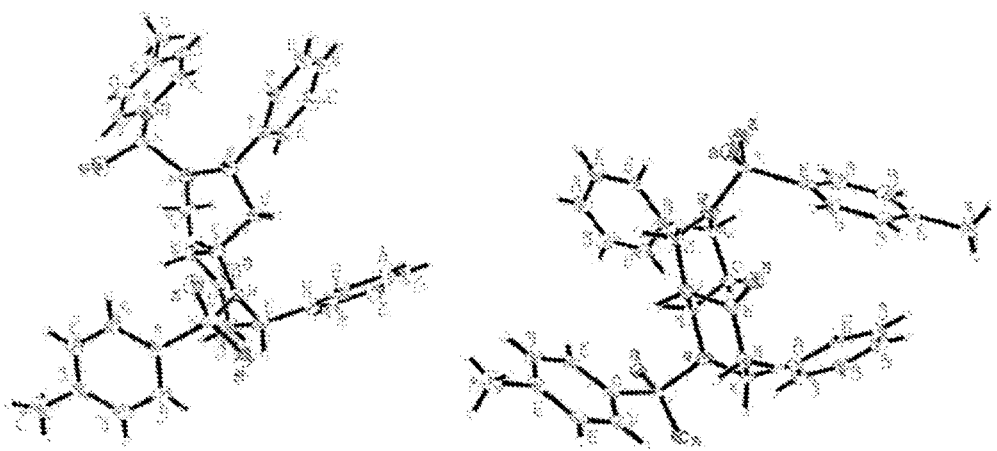

FIG. 13 shows crystallographic data for 8a8a (1a) and 8a8a' (1a').

DETAILED DESCRIPTION OF THE INVENTION

In one aspect of the present invention, it is provided a biological platform (assay) that detects a compound's capacity to perturb immune responses along a conserved spectrum of pro- and anti-inflammatory immune responses. The assay is multifaceted and highly reproducible across experiments, resulting in an approach capable of identifying lead compounds that either augment or dampen immune responses; distinguishing activity among structurally similar molecules, such as during SAR analysis; and identifying unexpected perturbations on immune responses among diverse classes of drugs. Pro-inflammatory compounds promote EC-triggered innate immune activation, while anti-inflammatory compounds inhibit EC-triggered innate immune activation. In some embodiments, the assay comprises co-culturing endothelial cell with monocyte (EC-monocyte co-culture).

As used herein, in some embodiments, the term "pro-inflammatory compound" is used interchangeably with the term "pro-inflammatory small molecule" and shall be understood in a way that that direct treatment of independent EC or a monocyte with such a small molecule(s) would not result in significant production of MIP1β or MIP1α; and, as with IFNγ, co-culture of EC and monocyte, both activated by such molecules, is required for chemokine induction. As used herein, the term significant production of MIP1β or MIP1α is generally known to a person of ordinary skill in the art, and in some embodiments, can mean production of MIP1β or MIP1α increased by at least 1%, 5%, 10% or 20% relative to the noise.

In another aspect of the present invention, it is provided a small molecule that activates human endothelial cells. Such small molecules mediates EC-triggered induction of innate immune activation in that direct treatment of independent EC or a monocyte with such a small molecule(s) would not result in significant production of MIP1β or MIP1α; and, as with IFNγ, co-culture of EC and monocyte, both activated by such molecules, is required for chemokine induction.

In some embodiments, the small molecule or compound is octahydro-1,6-naphthyridin-4-one compound or analog, or a pharmaceutically acceptable salt thereof. In some embodiments, the small molecule can be a prodrug of the small molecule.

In a further embodiment, the present invention provides a composition. The composition comprises a small molecule that activates human endothelial cells. Such small molecules mediates EC-triggered induction of innate immune activation in that direct treatment of independent EC or a monocyte with such a small molecule(s) would not result in significant production of MIP1β or MIP1α; and, as with IFNγ, co-culture of EC and monocyte, both activated by such molecules, is required for chemokine induction.

In some embodiments, the small molecule or compound is octahydro-1,6-naphthyridin-4-one compound or analog, or a pharmaceutically acceptable salt thereof. In some embodiments, the small molecule can be a prodrug of the small molecule.

In some embodiments, the composition can further include a carrier, which is further described below.

In another aspect of the present invention, it is provided a method augmenting innate immune response in a mammalian subject (e.g., a patient) wherein the mammalian subject suffers from a condition that can be treated or ameliorated by augmenting innate immune response in the mammalian subject. The method comprises administering to the mammalian subject (e.g., a patient) needing treatment a small molecule that activates human endothelial cells. Such small molecules mediates EC-triggered induction of innate immune activation in that direct treatment of independent EC or a monocyte with such a small molecule(s) would not result in significant production of MIP1β or MIP1α; and, as with IFNγ, co-culture of EC and monocyte, both activated by such molecules, is required for chemokine induction. In some embodiments, the condition is, for example, a cancer.

In some embodiments, the small molecule or compound is octahydro-1,6-naphthyridin-4-one compound or analog, or a pharmaceutically acceptable salt thereof. In some embodiments, the small molecule can be a prodrug of the small molecule.

In some embodiments of the method, the small molecule can be included in a composition. In some embodiment of the method, the composition can further include a carrier, e.g., a pharmaceutically acceptable carrier.

In a further aspect of the present invention, it is provided a method of forming an octahydro-1,6-naphthyridine-4-one compound or analog. The method comprises a modular synthetic route comprising:

forming an enol ether intermediate via phosphine-catalyzed [4+2] annulation of an allenoate with a first imine building block followed by treatment with Tebbe reagent and anhydrous pyridine to form an enol ether intermediate, subjecting the enol ether intermediate to endo-selective Diels-Alder reaction with a second imine building block to yield an octahydro-1,6-naphthyridine interminate, and forming the octahydro-1,6-naphthyridine-4-one compound.

In some embodiments of the method, the allenoate is formed by coupling a Wang resin having reactive hydroxyl groups with 2-methyl-2,3-butadienoic acid. In these embodiments, the method is solid phase synthesis. In some embodiments, the solid phase synthesis can be carried via combinatorial library construction using, e.g., Synphase lanterns as the solid support where the first imine building block can be encoded by tagging individual lanterns with, e.g., colored spindles and cogs to encode the imine building blocks.

In some further embodiments of the above method, the method further comprises performing structure-activity-relationship (SAR) studies.

General methods of synthesizing the compound can be found in, e.g., Stuart Warren and Paul Wyatt, Workbook for Organic Synthesis: The Disconnection Approach, second Edition, Wiley, 2010.

As used herein, the octahydro-1,6-naphthyridin-4-one analog refers to a small molecule functionally or structurally related to octahydro-1,6-naphthyridin-4-one. In some embodiments, the octahydro-1,6-naphthyridin-4-one analog is one of:

104A5
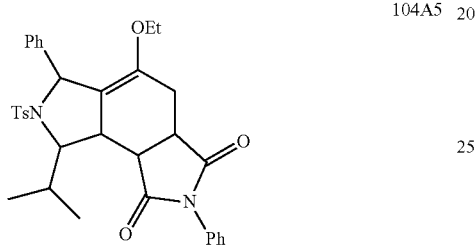

104A7
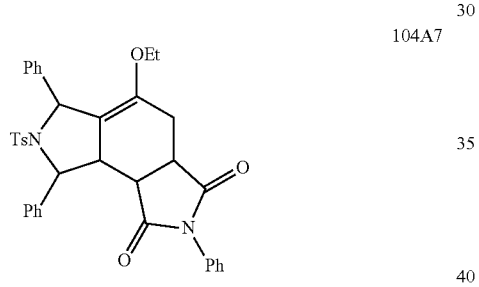

104A8
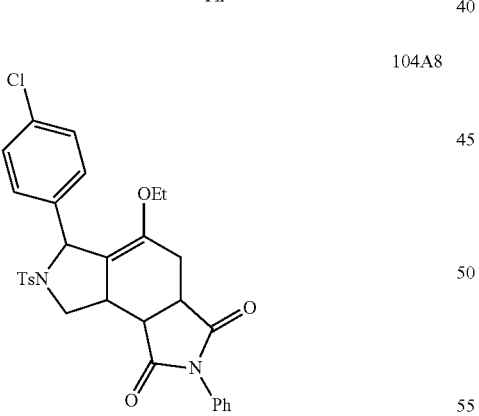

104B11
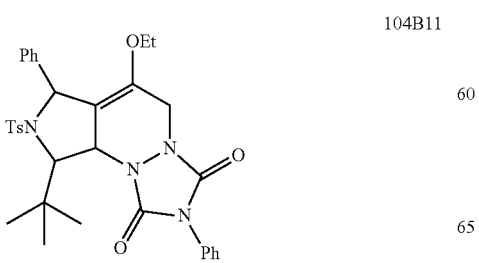

104B9
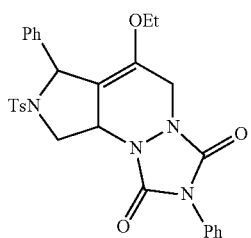

104B10
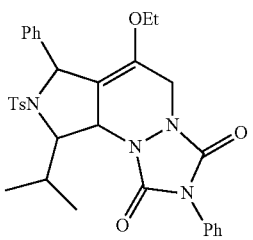

104C2
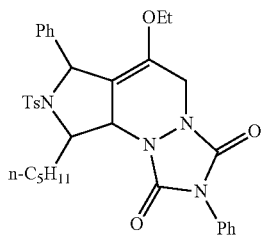

104C3
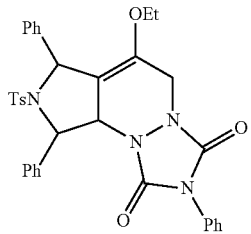

104C5
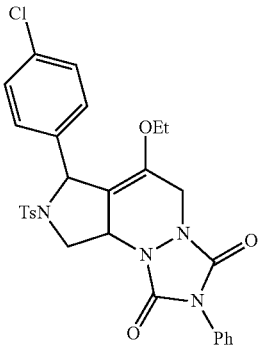

104C4
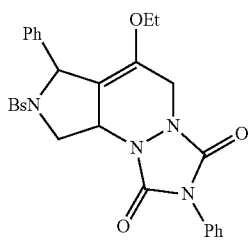

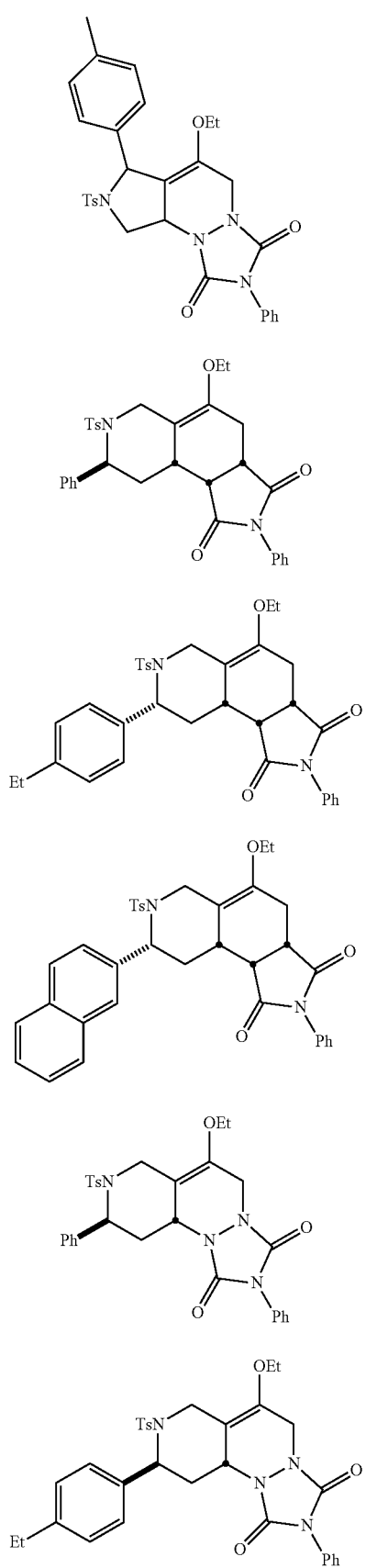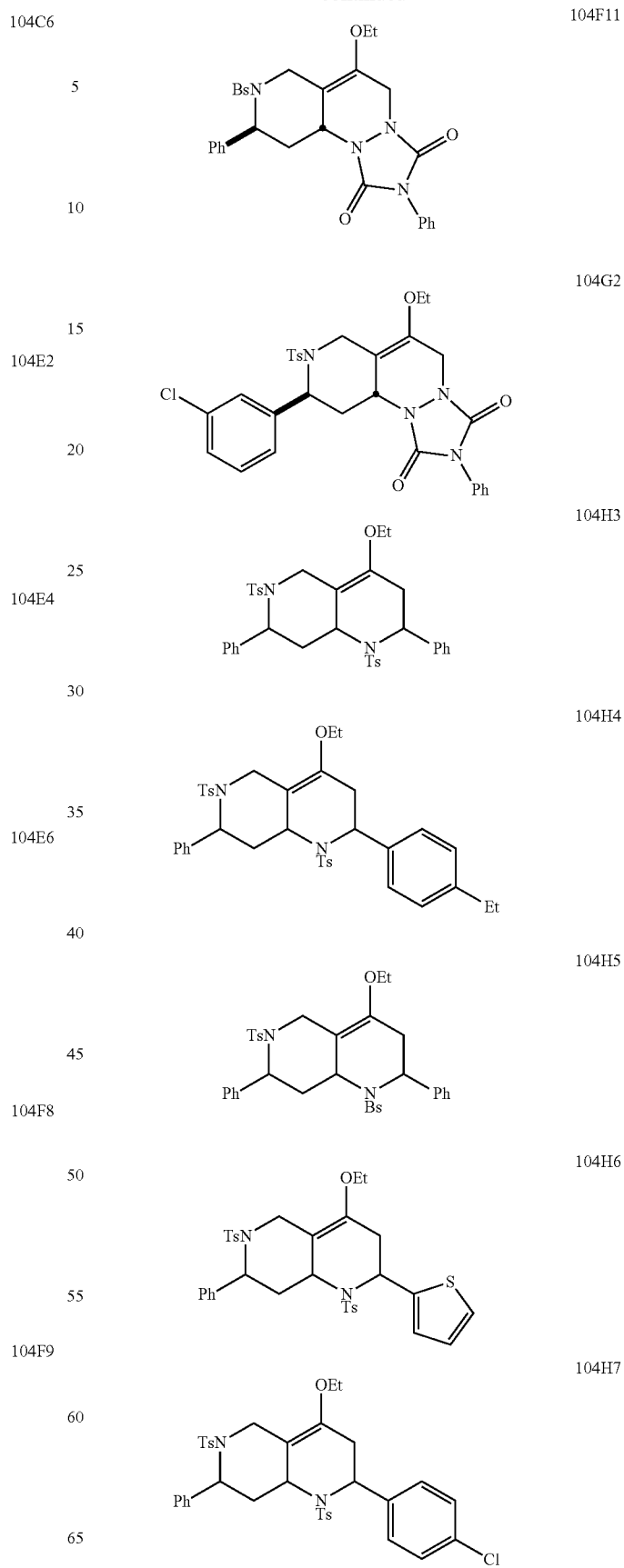

104H8
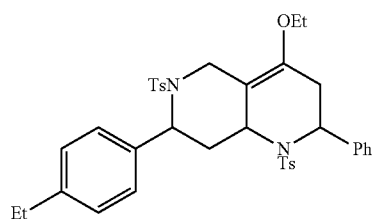
104H9
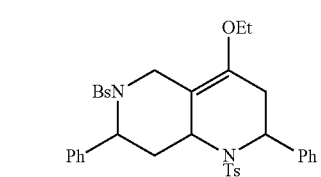
104H10
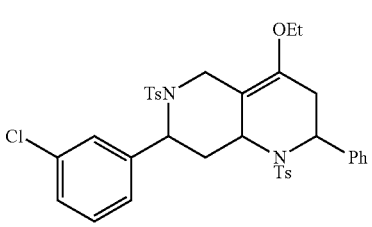
104H11
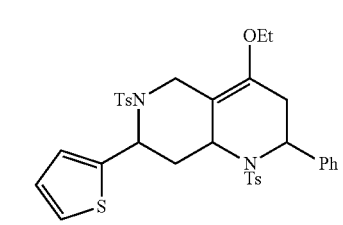
105A3
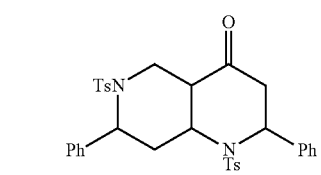
105A6
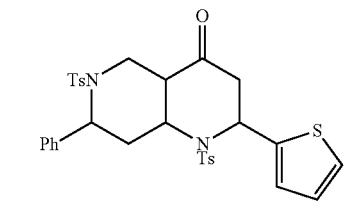
105A7
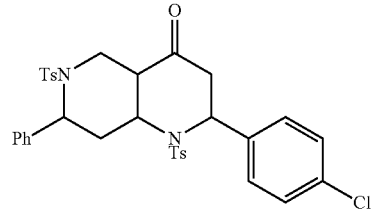
105A8
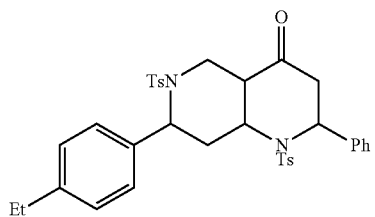
105A9
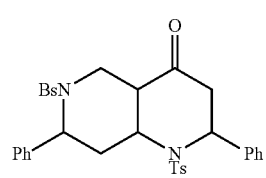
105A10
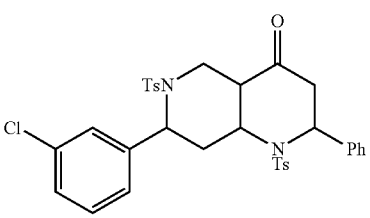
105A11
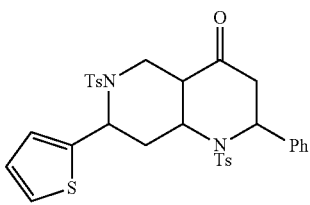
105B2
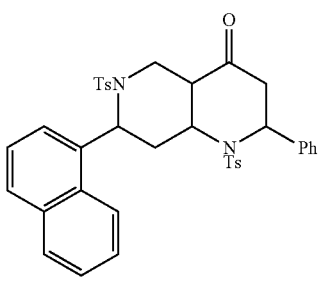
105B3
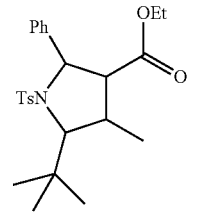
301C3
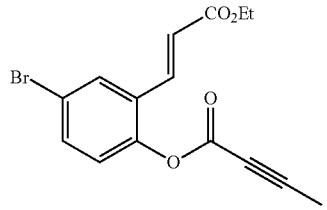

In some other embodiments, the analog is
104A2-A10
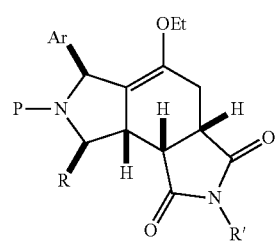
104B9-C8
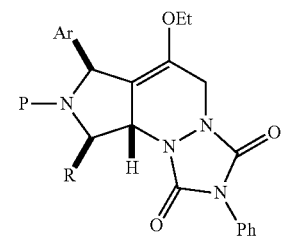
104D11-F2
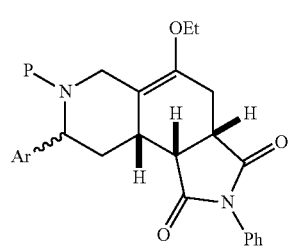
104F8-G2
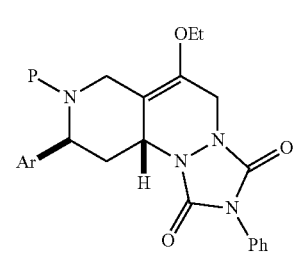
104H3-105A2
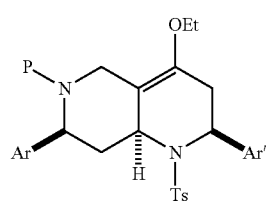
105A3-B2
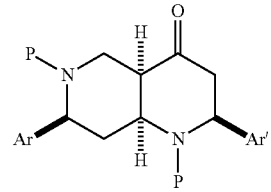
Ar = phenyl, 4-MeC$_6$H$_4$, 4-EtC$_6$H$_4$, 4-ClC$_6$H$_4$, 3-ClC$_6$H$_4$, 2-thiophenyl, 1-naphthyl
P = tosyl, benzenesulfonyl
R = H, isopropyl, n-pentyl, t-butyl, phenyl
R' = phenyl, ethyl, benzyl
Ar' = phenyl, 4-EtC$_6$H$_4$, 4-ClC$_6$H$_4$, 2-thiophenyl
In some further embodiments, the analog is
A2
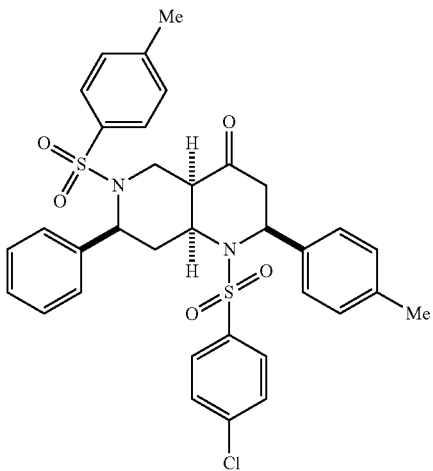
A3
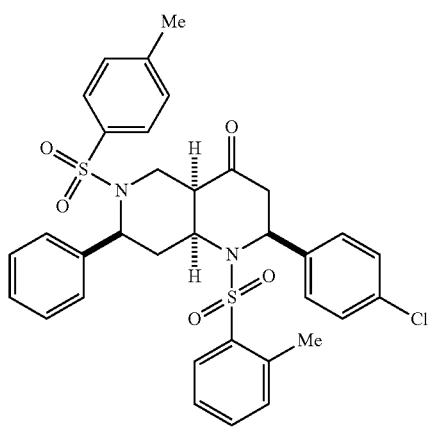
A4
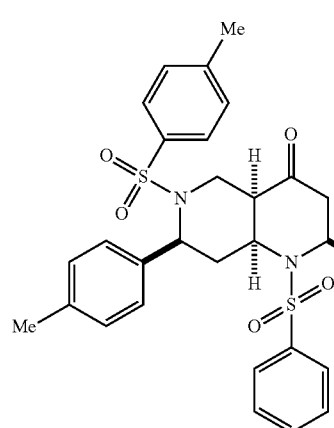

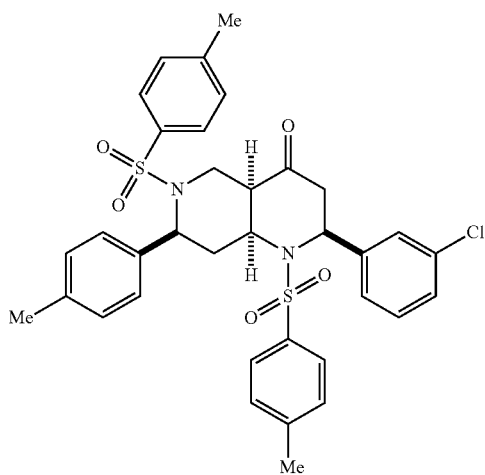
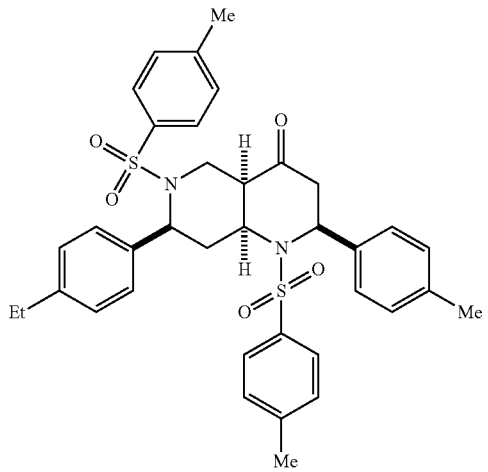

A11
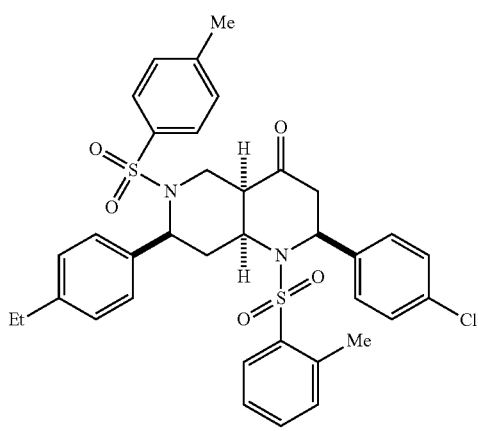
B2
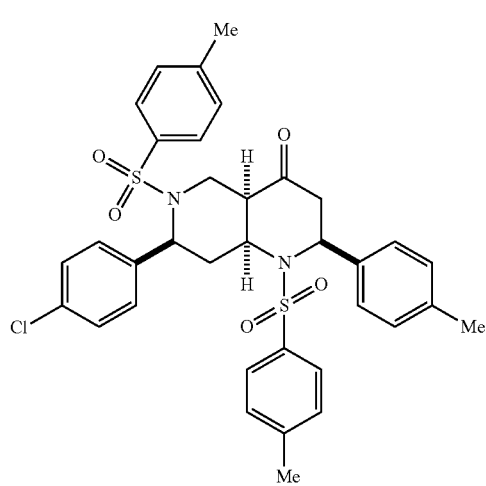
B3
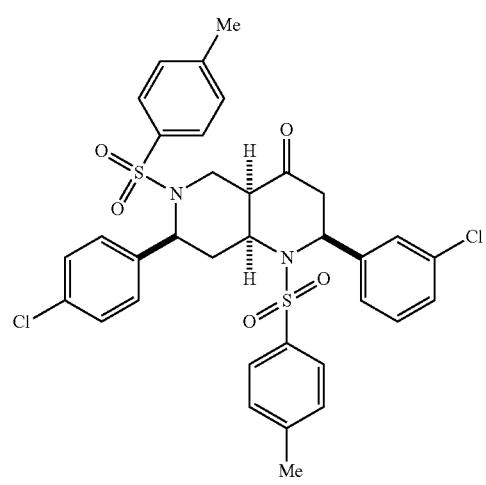
B4
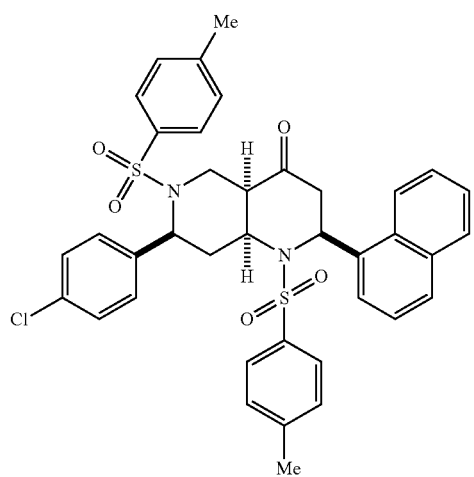
B5
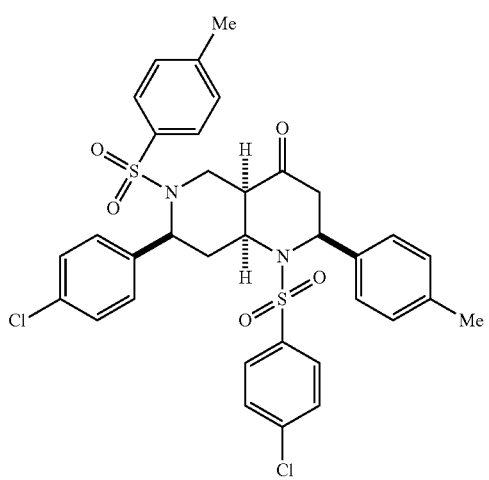
B6
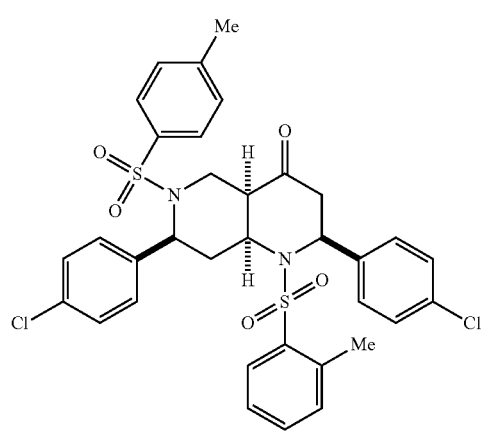

-continued
B7
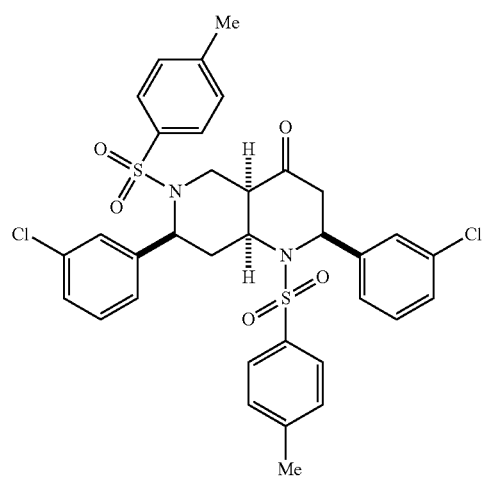
B8
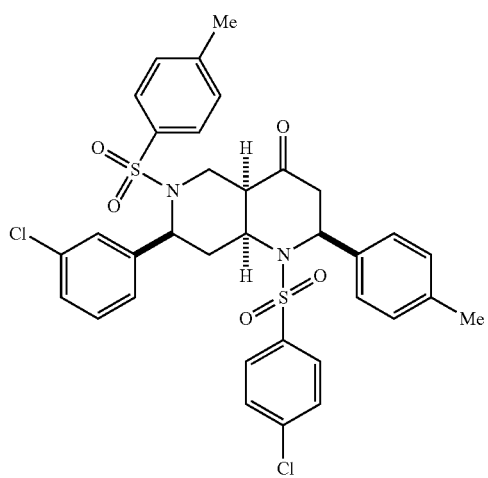
B9
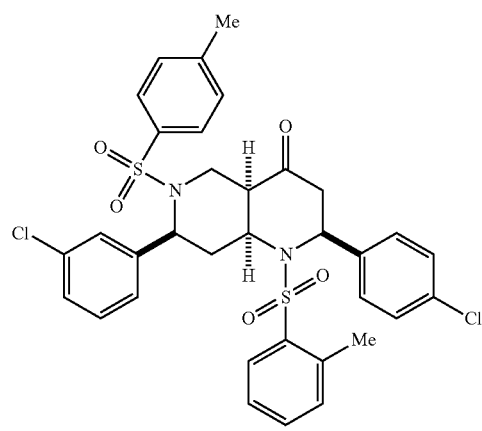
-continued
B10
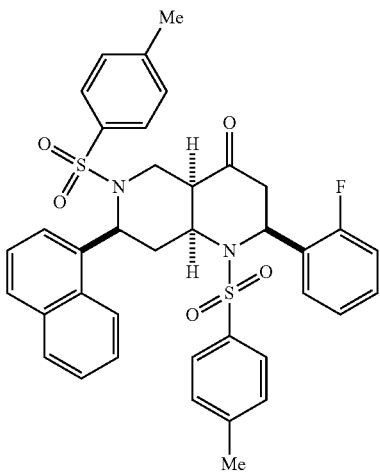
B11
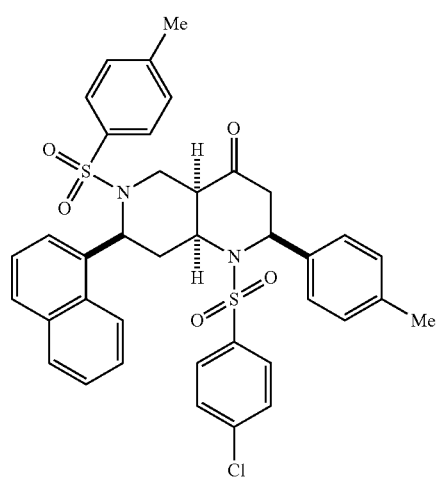
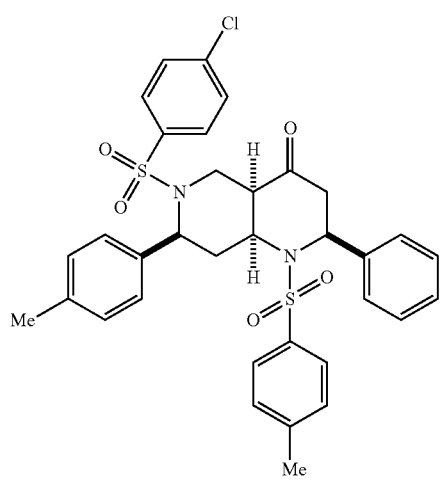

21
-continued
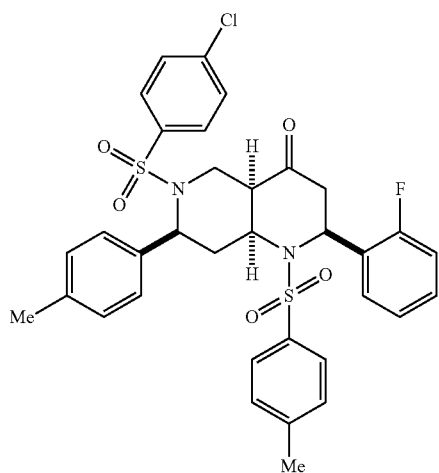
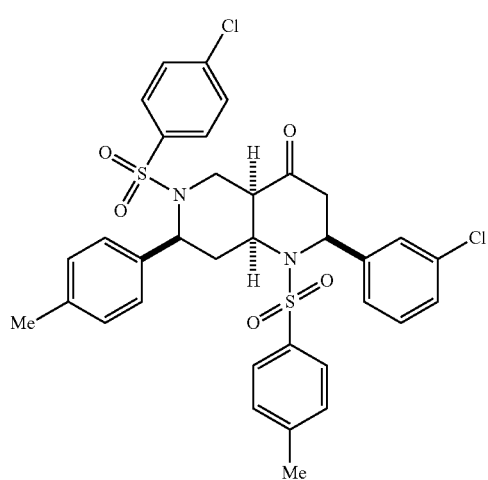
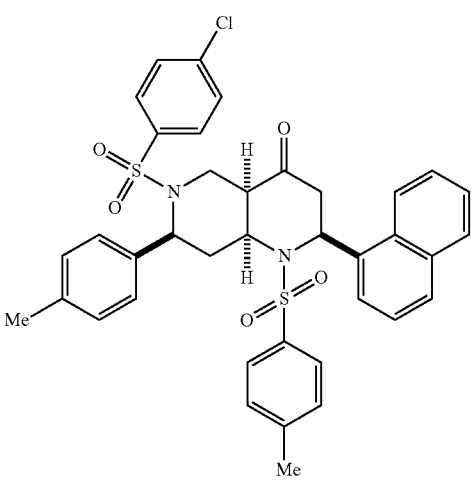
22
-continued
C6
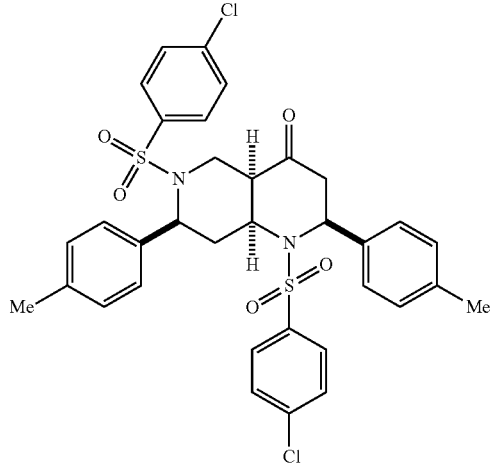
C7
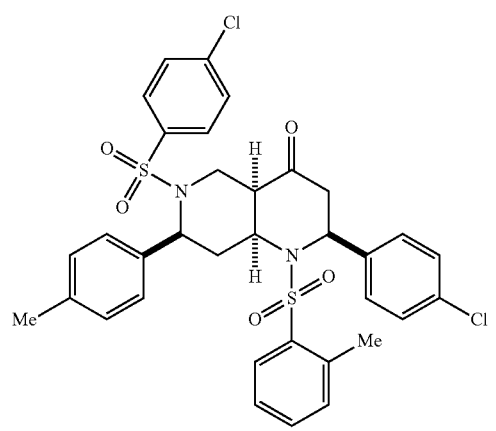
C8
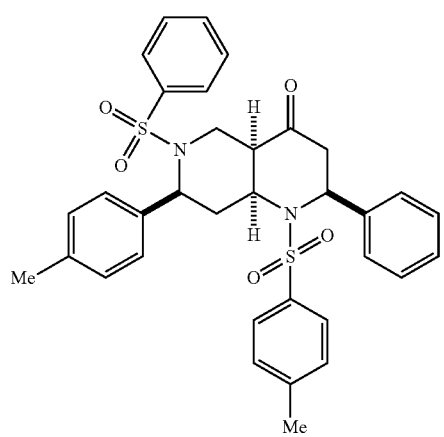

C9
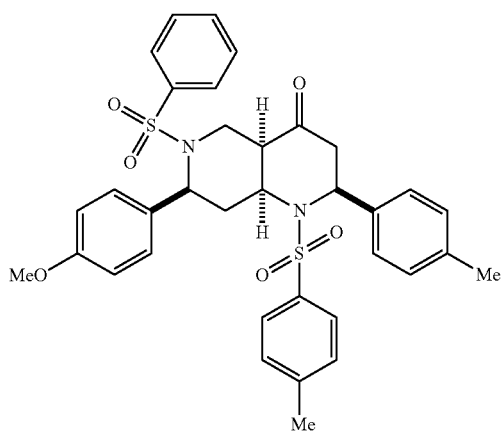
C10
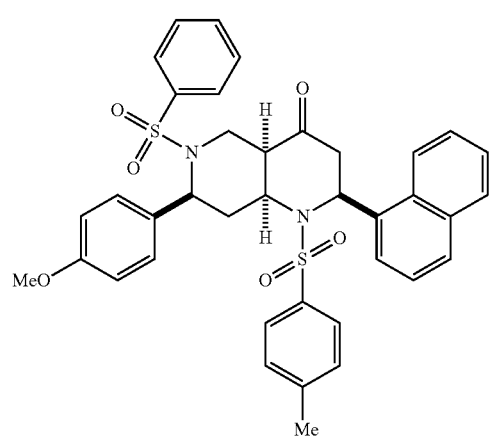
C11
D2
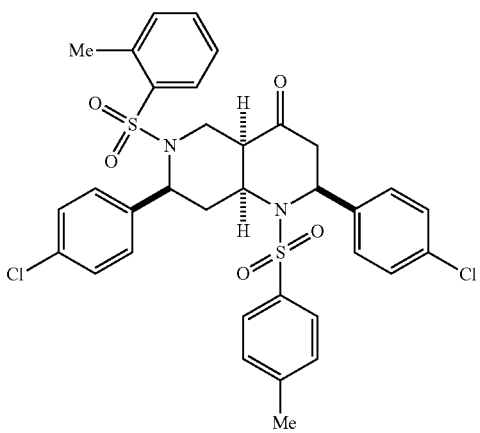
D3
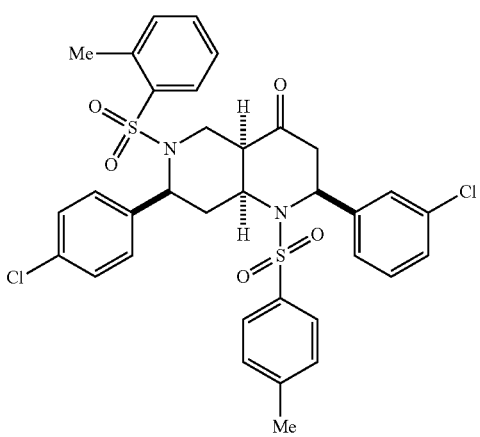
D4
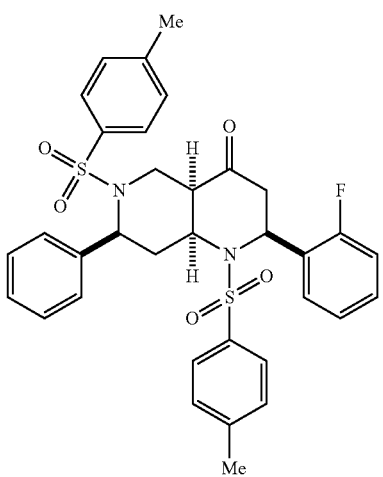

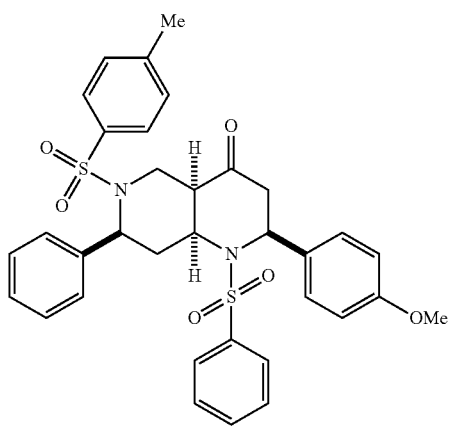
D5
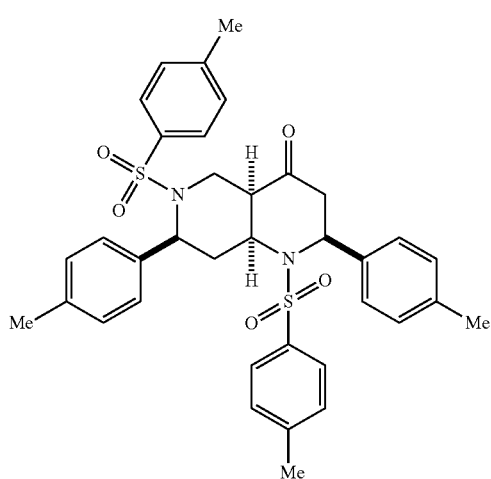
D6
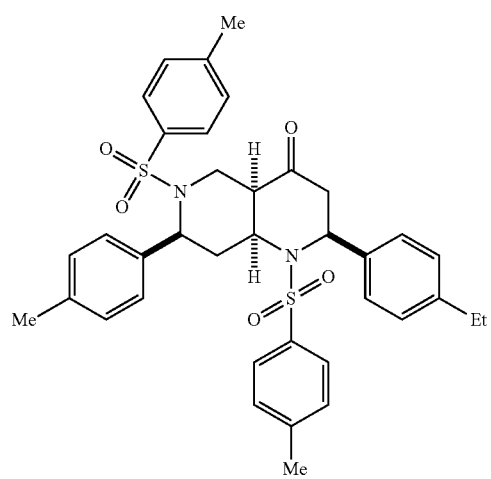
D7
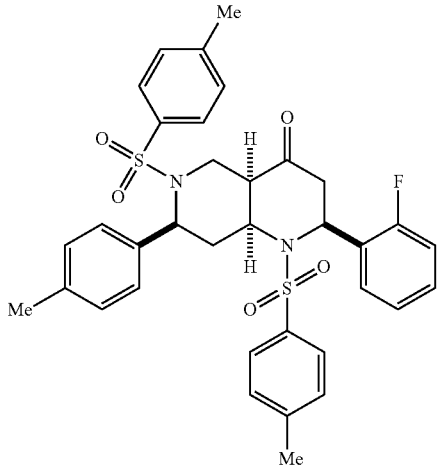
D8
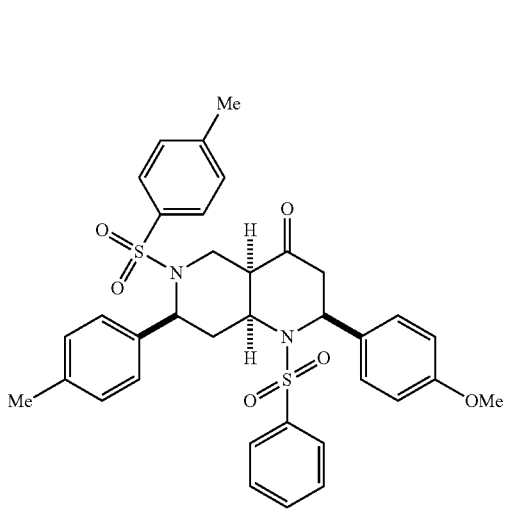
D9
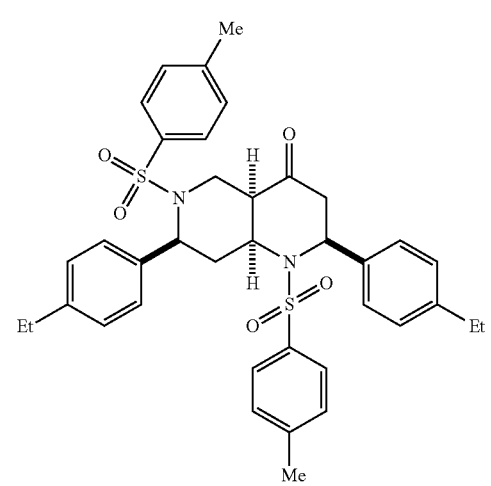
D10

D11
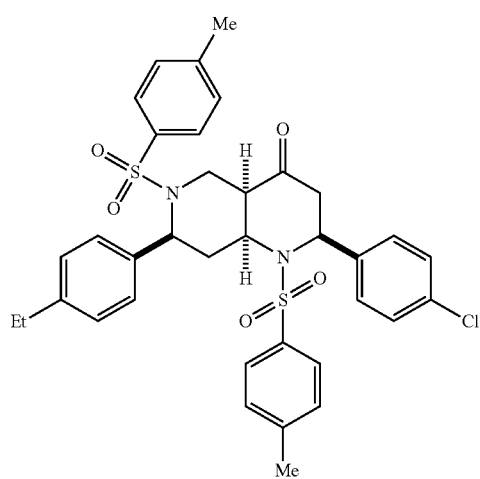
E2
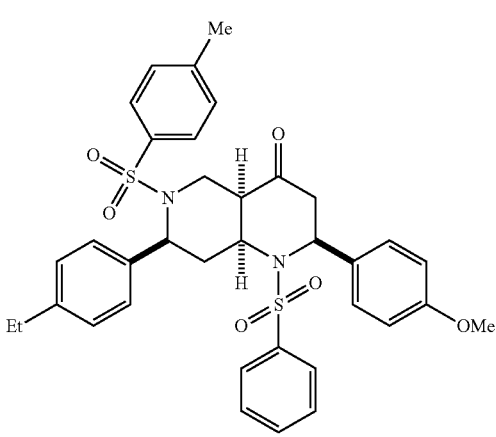
E3
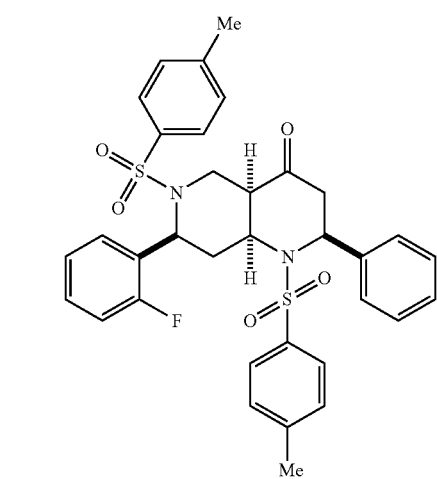
E4
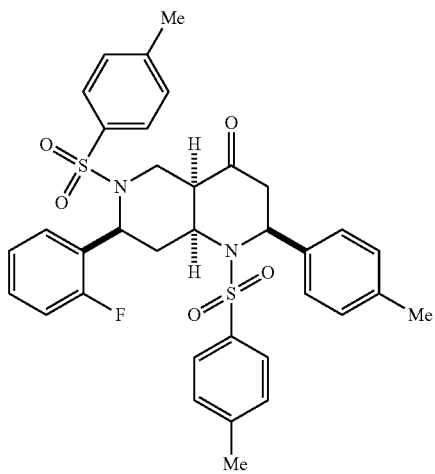
E5
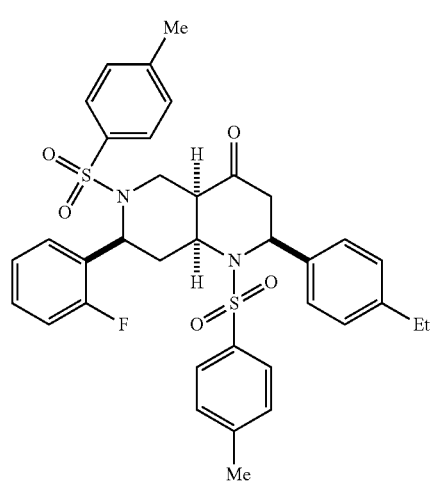
E6
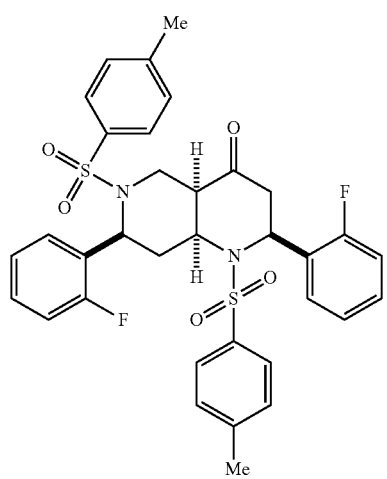

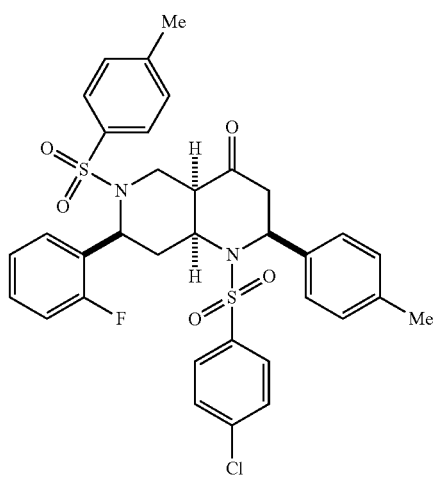
E7
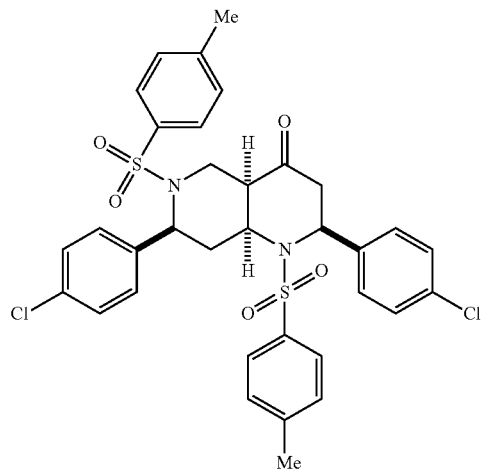
E10
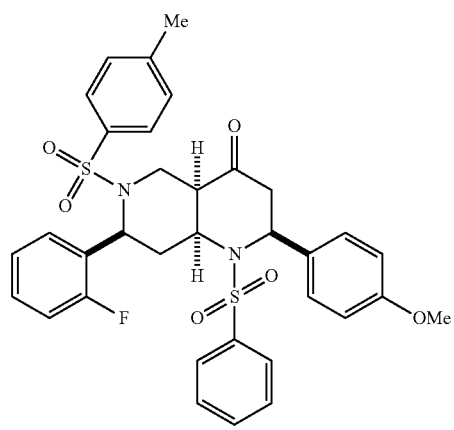
E8
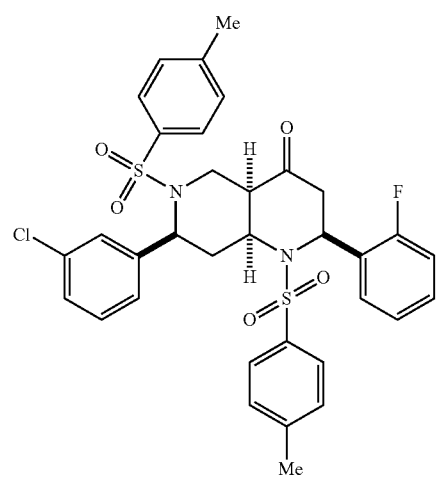
E11
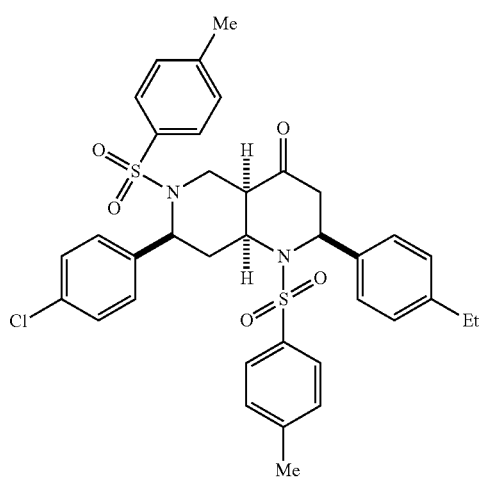
E9
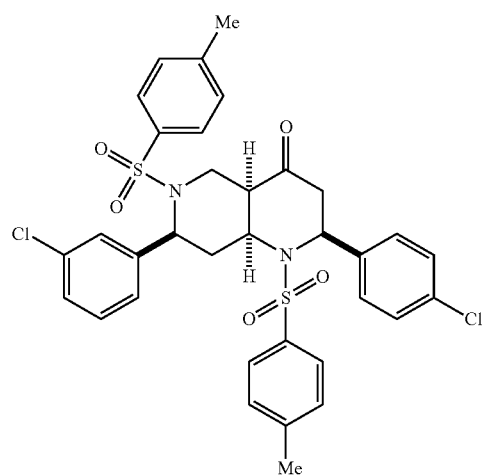
F2

-continued
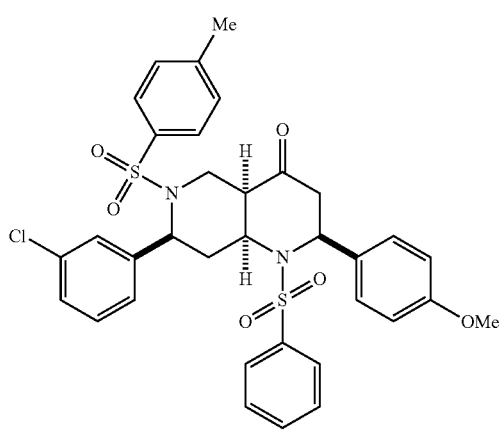
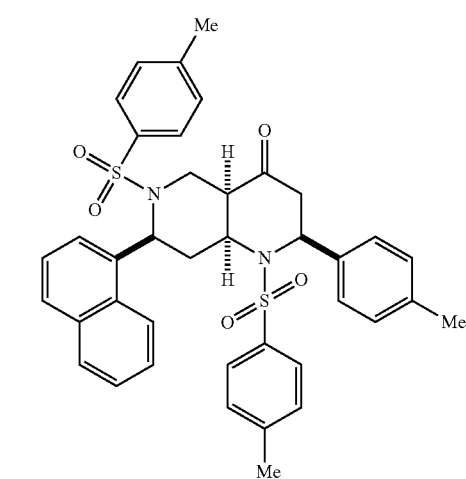
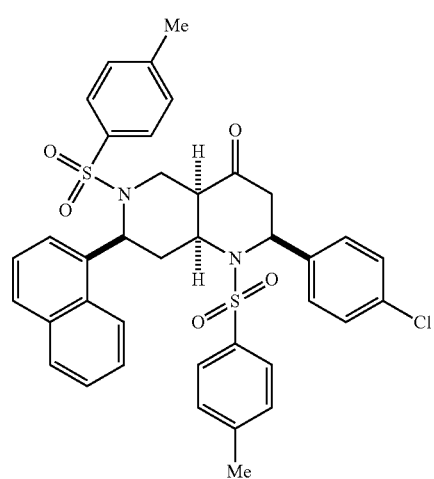
-continued
F3
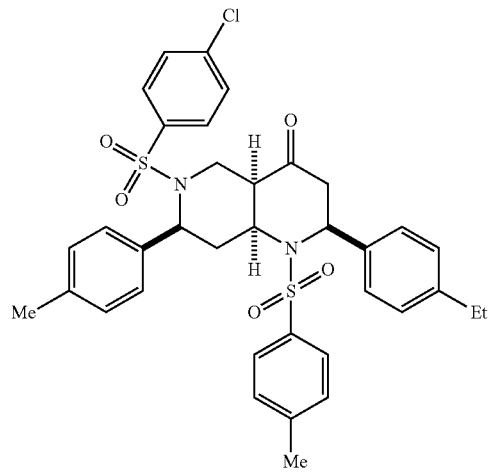
F4
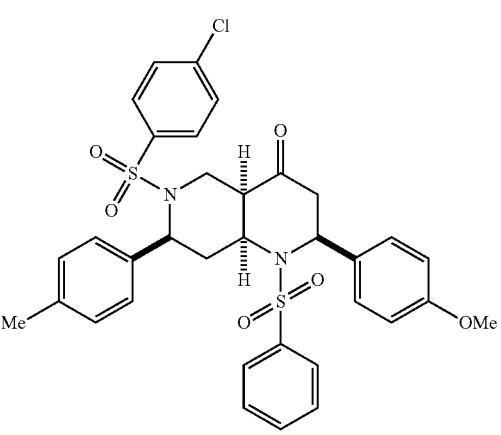
F5
F6
F7
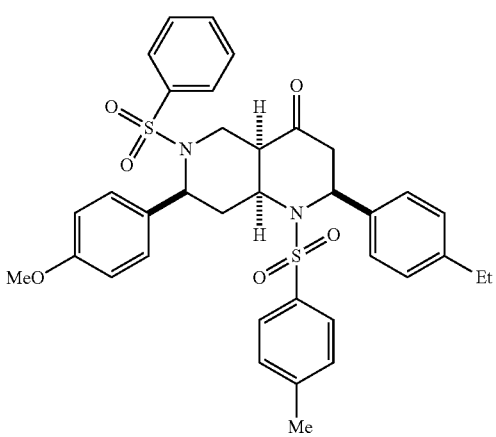
F8

F9 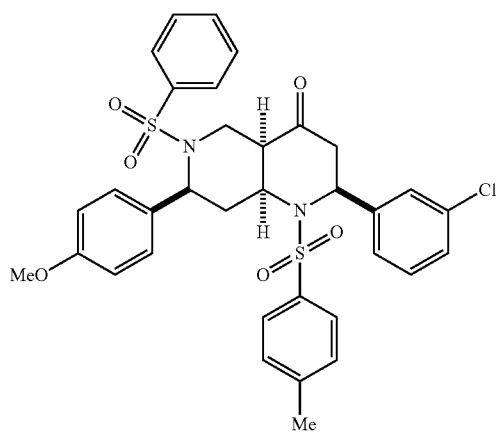
F10 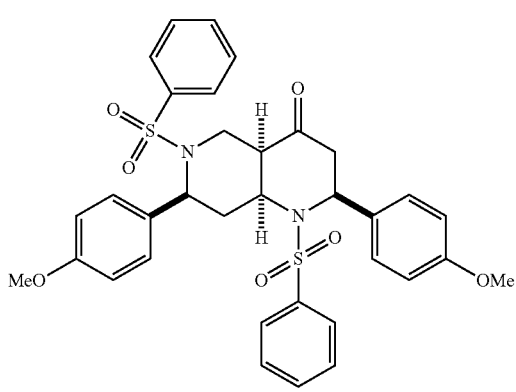
F11 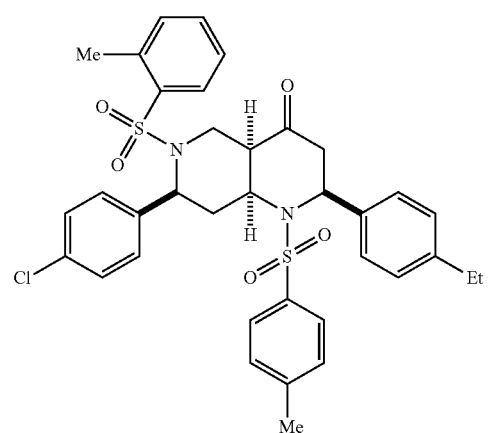
G2 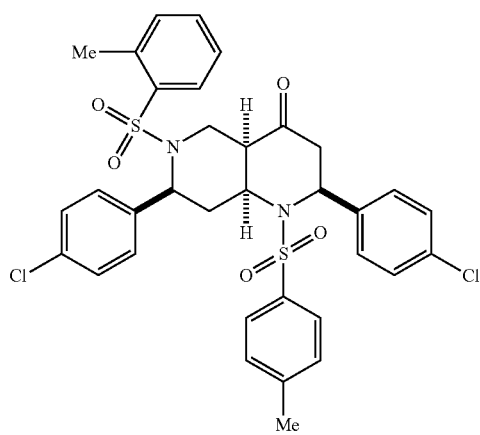
G3 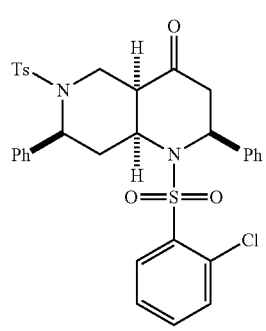
G4 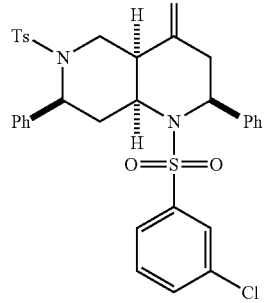
G5 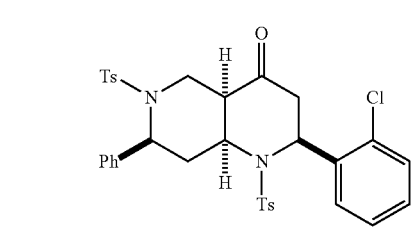
G6 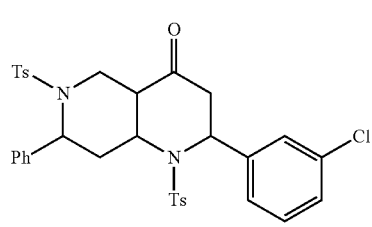

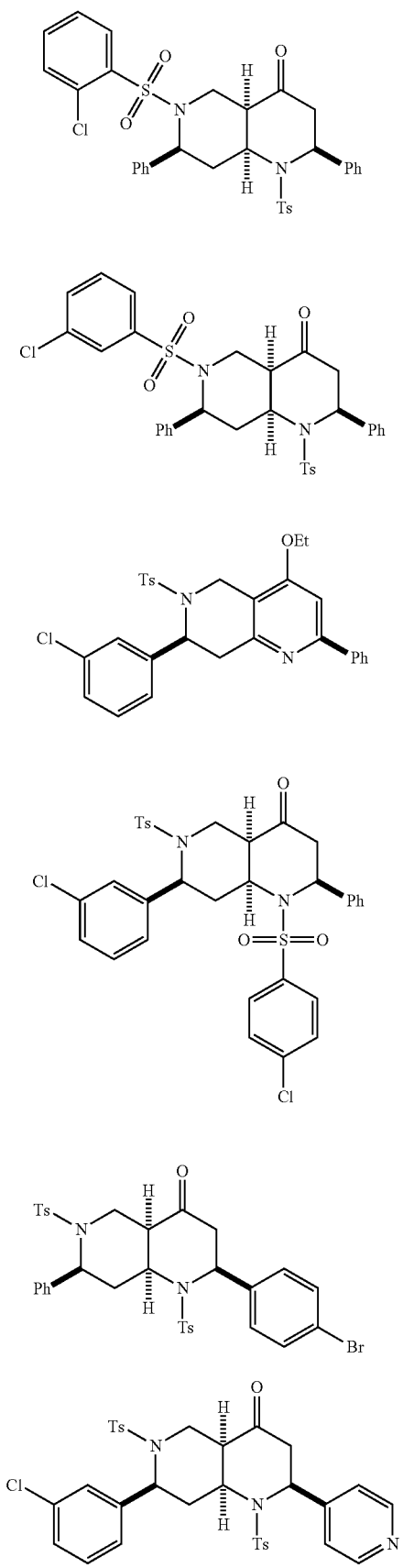

H9
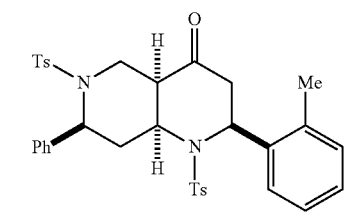
H10
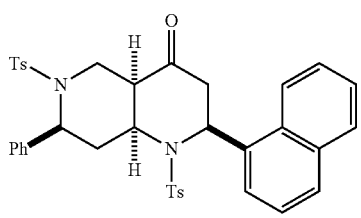
H11
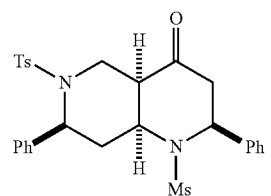
2A2
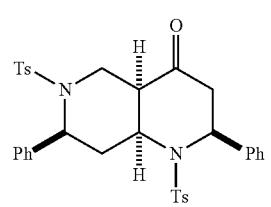
2A3
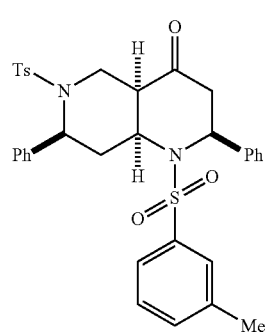
2A4
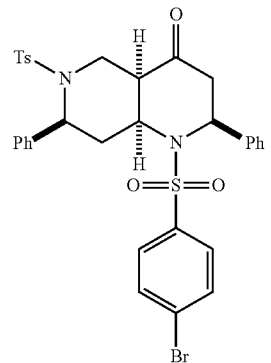
2A5
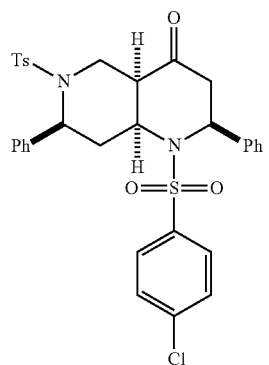
2A6
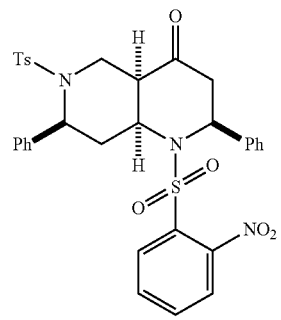
2A7
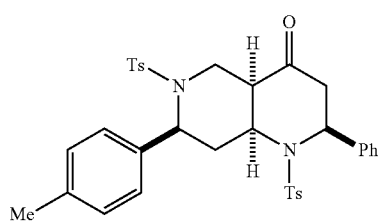
2A8
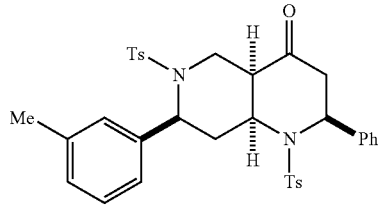
2A9
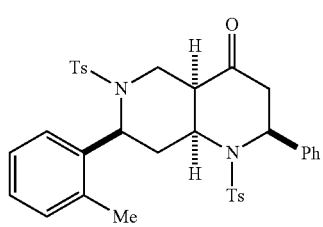
2A10
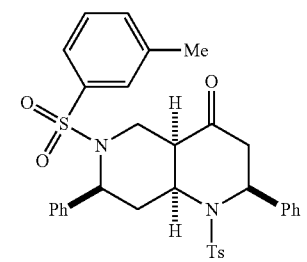

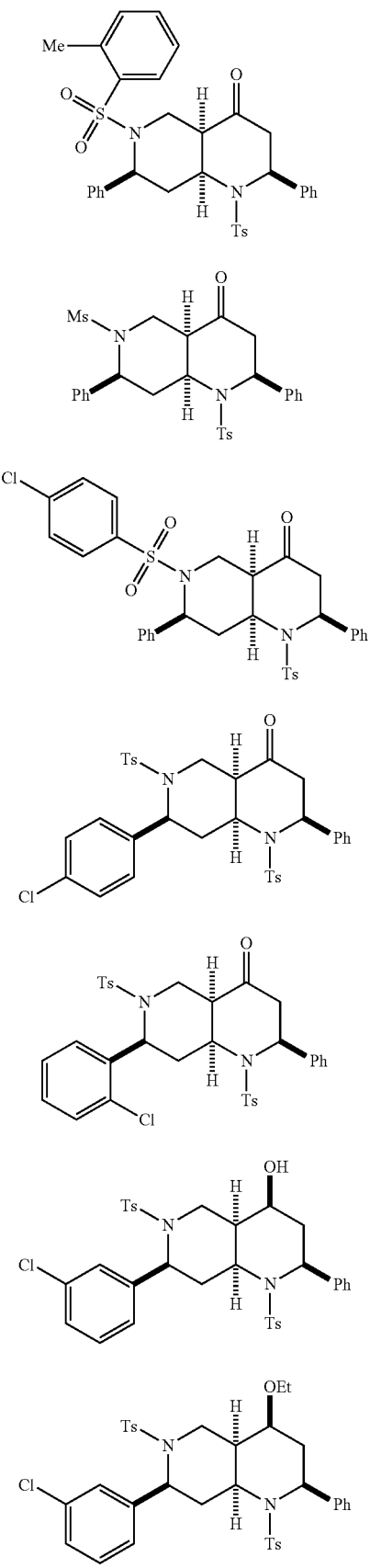

2A11

2B2

2B3

2B4

2B5

2B6

2B7

As used herein, a prodrug is generally pharmaceutically inactive and can be converted into a pharmaceutically active ingredient or species upon administering into a patient.

The term chemokine is generally known in the art and as used herein, refers to chemokines in immunity. In some embodiments, the term chemokine refers to MIP1β or MIP1α. As used herein, in some embodiments, increased production of chemokines refers to production of a particular immunity chemokine or overall immunity chemokine level increased by at least 1%, 5%, 10% or 20% relative to noise or control. Conversely, in some embodiments, decreased production of chemokines refers to production of a particular immunity chemokine or overall immunity chemokine level decreased by at least 1%, 5%, 10% or 20% relative to noise or control.

As used herein, the term significant production of MIP1β or MIP1α is generally known to a person of ordinary skill in the art, and in some embodiments, can mean production of MIP1β or MIP1α increased by at least 1%, 5%, 10% or 20% relative to noise or control.

Embodiments the Biological Platform

Figure 9:
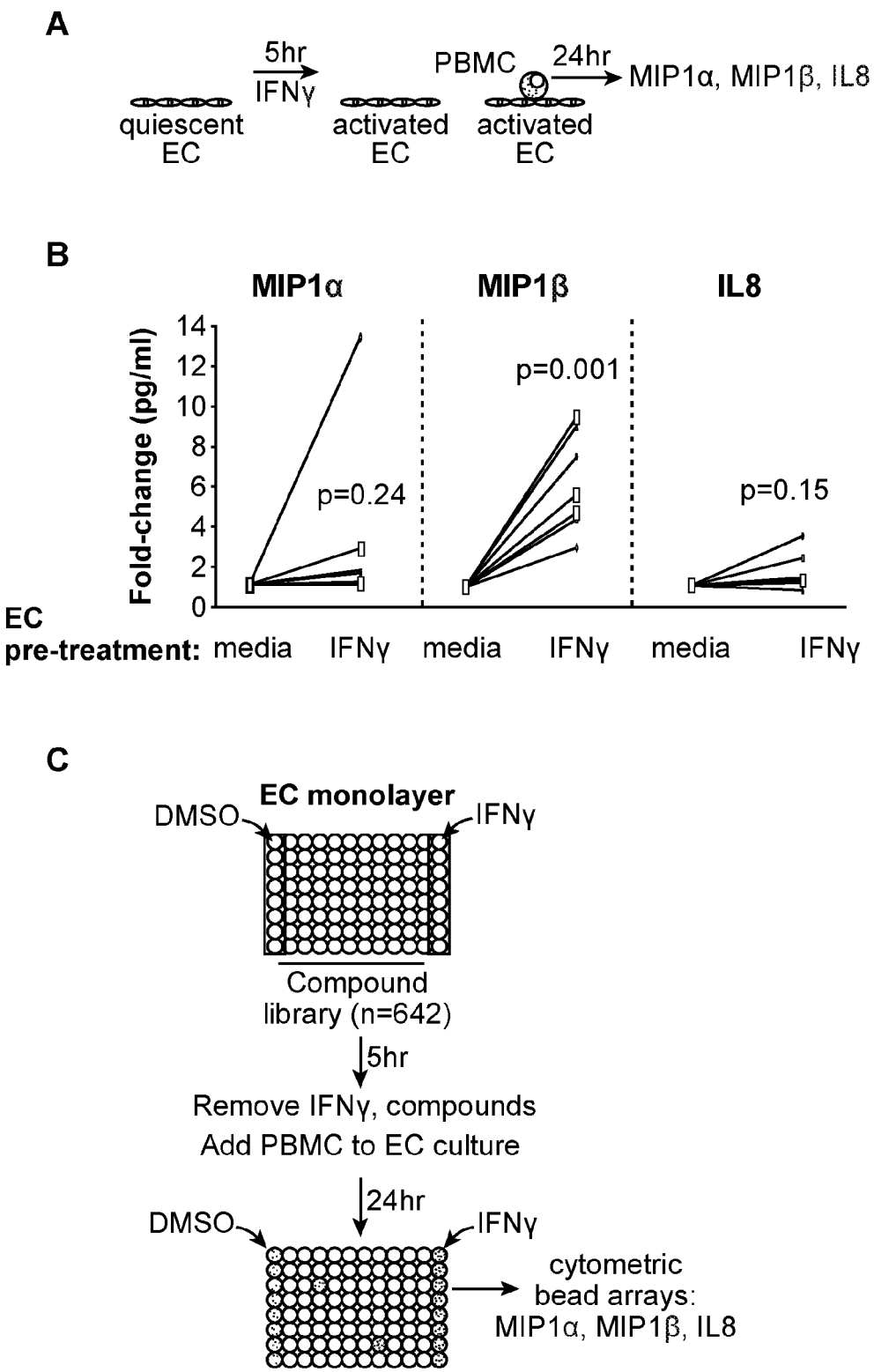
FIGS. 9A-9C show a further embodiment of the invention biological platform for the detection of activated endothelium. (A) Primary endothelial cells were seeded to confluence in a 96 well format and activated by IFNγ (10 ng/ml). After 5 hours, IFNγ was removed, wells were washed, and then primary human peripheral blood mononuclear cells (PBMC) were added at a ratio of 3:1 (PBMC:EC). 20-24 hours later, supernatants were removed and chemokines were quantified by cytometric bead arrays. (B) MIP1β production, but not MIP1α or IL8 levels, reliably detects endothelium activated by IFNγ. Chemokines produced in co-culture conditions with quiescent vs. activated EC; data represent the results from n=7 (MIP1α and MIP1β) and n=6 (IL8) independent experiments. (C) Chemical library screen for compounds that activate human endothelium. A 642 compound library was added following the same method as in A and B. Controls included DMSO and IFNγ on each plate. Supernatants were measured for chemokines by cytometric bead arrays.

The biological platform or assay described herein can be embodied in different ways (see, e.g., FIGS. 1 and 9). An embodiment of the biological platform of invention is provided below:
1. Primary human umbilical endothelial cells (EC) are adhered in 96 or 384-well plates at confluency for 2 hours.
2. Control stimuli (or compounds of interest) are added to EC for 5 hours.
3. Compounds are removed, EC washed, and primary human peripheral blood monocytes are added.
4. After 24 hours, 25 μl of supernatant is removed for MIP1α and MIP1β analysis.
5. After 42-48 total hours of co-culture, cells are harvested for flow cytometry.
6. Cells are labeled with: CD40, CD209, and CD163.
    a. Parameter 1: Gate on EC/monocytes by using FSC vs SSC on whole co-culture population
    b. Parameter 2: Use SSC vs. CD40 to separate monocytes from EC. Note: loss of EC population reflects compound toxicity.
    c. Parameter 3: Gate on CD40+ monocytes
    d. Parameter 4: Determine CD40 MFI on CD40+ macrophages
    e. Parameter 5: Determine CD209 MFI on CD40+ macrophages
    f. Parameter 6: Determine CD163 MFI on CD40+ macrophages
    g. Parameter 7: Subtract vehicle control MFIs from each sample of interest. In the example below (FIGS. 2A and 2B), EC stimulation with IFNγ may promote EC-triggered MΦ with CD40 MFI=40, CD209 MFI=60, CD163=10. DMSO treated EC promote MΦ with CD40=20, CD209 MFI=30, and CD163=100. This would result in Δs of: CD40: 40−20=+20; CD209: 60−30=+30; CD163: 10−100=−90.
    h. Parameter 8: Scatter plot of CD40 vs CD209 (FIG. 2A, top).
    i. Parameter 9: To separate populations further, plot CD209 (or) CD40 vs. CD163. (FIG. 2B, bottom).
    j. Parameter 10: Use MIP1α and MIP1β expression at 24 hours to corroborate pro- or anti-inflammatory effects, as described in attached manuscript. This serves as a simultaneous internal control and counter screen. Pro-inflammatory compounds promote EC-triggered innate immune activation, while anti-inflammatory compounds inhibit EC-triggered innate immune activation.

Further details of the platform are described in the examples below.

Note, variations of the platform can be readily made by a person of ordinary skill in the art. For example, in addition to human umbilical endothelial cells, endothelial cells of other type (human or animal) can be used. In some embodiments, animal umbilical endothelial cells can be used in the platform. In some embodiments, the platform can have plates of various designs, which are either commercially available or readily made by a person of ordinary skill in the art.

Exemplary screens were performed. FIGS. 1-4 show some exemplary results using the biological platform described herein.

FIGS. 1A and 1B show results of screens of invention on small molecule libraries. A. A library with no FDA approved compounds. B. Prestwick library of FDA approved compounds. In the first screen (FIG. 1A) a small molecule library (no FDA-approved compounds) was tested. Profiling across 10 parameters resulted in the identification of novel compounds that were predicted to result in enhancing or dampening immune effects. We have confirmed that compounds that fall in the enhanced pole heighten inflammatory responses, while those in the dampening pole inhibit inflammation. Microarray analysis of 4 enhanced compounds revealed that between 26-32% of the induced genes overlapped with the "inflammatory" positive control (p-values range: $1.2 \times 10^{-205}$ to $9.1 \times 10^{-70}$). Microarray analysis of 4 dampening compounds revealed that they induced 21-41% of the genes induced by the "anti-inflammatory" control (p-values range: $5.9 \times 10^{-82}$ to $8.7 \times 10^{-25}$). Therefore, our screen identified novel compounds that (a) promoted or dampened biological immune responses and (b) induced gene expression changes remarkably similar to positive controls.

In the second screen (FIG. 1B), the Prestwick library of FDA approved compounds was tested. Profiling revealed that compounds that were expected to dampen inflammation fell within the dampening pole; within the top 5% of anti-inflammatory compounds, 26.4% were glucocorticoids, with dexamethasone being the most potent. Conversely, six COX 1/2 inhibitors were among the top 5% pro-inflammatory enhanced compounds. This would have been surprising, except for the now well-recognized pro-inflammatory effects of this class of agents. As another intriguing example, among oral hypoglycemics, only metformin fell within the "anti-inflammatory" dampening subset of molecules, consistent with its unique cardioprotective role in diabetic patients.

FIGS. 2A and 2B show data from 384-well plate of EC treated with IFNγ (n=44), DMSO (n=44) or TGFβ (n=44). A: differences in CD209 and CD40 MFI are plotted as described in Parameter "h". TGFβ (anti-inflammatory control), DMSO control, IFNγ (pro-inflammatory control). B: Same data as in the top (FIG. 2A), except the populations are further stratified by comparing CD163 vs. CD209 expression on EC-triggered CD40+MF.

We demonstrate in the studies shown in FIG. 1A that compounds that segregate with IFNγ are pro-inflammatory, while compounds that segregate with TGFβ are anti-inflammatory.

FIG. 3A shows small molecule screen (n=642) was performed to identify compounds that mimicked IFNγ, as determined by their capacity to polarize the endothelium to trigger monocytes to become inflammatory (CD209+ CD163−) MF. * represents the naphthyridine family of compounds (9 of 10 were "hits"). Dashed line represents 3 s.d. from DMSO mean. FIGS. 3B, 3C, and 3D shows results of tests by which selected compounds from two structurally distinct families were validated; like IFNγ, EC polarized by such compounds also drive monocytes to differentiate into MF that are less phagocytic, as determined by diI-oxLDL uptake, but more responsive to TLR stimulation, as determined by CBA (*, p value <0.01).

FIGS. 4A-F shows results tests of defining key regulatory gene networks by which naphthyridines and IFNγ regulate innate immunity. (A) Transcriptome profiling of active and inactive biological/chemical stimuli were compared, in search of transcription factors (TF) induced (>1.25 fold over DMSO) by active, but not inactive perturbations. IFNγ and IFNα are structurally similar members of the IFN family, with differing capacity to polarize the EC. 105A9, A10 are naphthyridines, and D10 and E2 are active and inactive analogues, respectively, of 105A10. 104 B11, C2 belong to another EC-activating family of compounds. (B-D) Of the 4 candidate TF, only ATF3 polarizes the EC to trigger inflammatory MF. (E) siRNA against ATF3 prevents IFNγ-mediated EC polarization. (F) Gene expression analysis in EC with forced expression of ATF3 vs. empty control vector (triplicate wells, fold change >1.4 or <0.6, p-value <0.05) was performed, and induced genes were analyzed by Ingenuity Pathway analysis; ATF3 overexpression leads to an enrichment of "IFN signaling" network, indicating that it is one mechanism by which compounds engage IFN pathways.

Formulations

The composition disclosed herein can be formulated into various formulations. The composition can be formulated for systemic or local delivery of the radiation protective compound. For example, such formulations include, e.g., liquid, solid, or semi-solid formulations for various mode of administration, e.g., oral administration, subcutaneous injection, intravenous injection, topical administration, or implant.

The compositions can be formed into a formulation suitable for a desired mode administration. In some embodiments, the composition can include a pharmaceutically acceptable carrier. The content of the compound disclosed herein in the composition according to the present invention may range, but is not limited to, preferably from 0.001 to 20 wt. %, more preferably from 0.01 to 15 wt. %, most preferably from 0.05 to 10 wt. %.

Formulations can be made suitable for different routes of administration, for example, liquids for intravenous administration, topical administration via application to the surface of the diseased site, or mucosal application to cavities of the nose, mouth, eye, rectum, vagina or bronchopulmonary; solid dosage forms that may dissolve in the mouth or be inhaled through the broncopulmonary; and semisolids that may be applied to cavity surfaces of the nose, mouth, eye, rectum, or vagina.

Examples of the carrier employed in the composition disclosed herein can include any desired carriers generally contained in drugs, fibers, polymeric materials and the like. Concerning pharmaceutical compositions, illustrative of such desired carriers are excipients, coloring matters, taste or smell corrigents, binders, disintegrators, coating materials, stabilizers, pH regulators, sugar-coating materials, emulsifiers, dispersants, and solubilizers. Especially for external dermal preparations, illustrative examples can include hydrocarbons such as liquid paraffin and vaseline, esters such as spermaceti and bees wax, triglycerides such as olive oil and beef tallow, higher alcohols such as cetanol and oleyl alcohol, fatty acids such as stearic acid and oleic acid, polyhydric alcohols such as propylene glycol and glycerin, nonionic surfactants, anionic surfactants, cationic surfactants, and thickeners. For clothing and plastics, illustrative examples can include plasticizers, crosslinking agents, coloring matters, antioxidants, and ultraviolet absorbers.

In some embodiments, an aqueous preparation or formulation of the composition disclosed herein may contain buffers, surfactants, humectants, preservatives, flavorings, stabilizers (including antioxidants) colorants, and other additives used in preparations administered into the oral cavity.

In some embodiments, liquid compositions preferably should have a pH value ranging from 2 to 10, preferably 3.5 to 9, most preferably 4 to 8. A preparation having a pH of less than 4 would be likely to cause a stinging sensation. Furthermore, the preparations having a higher pH are often unpleasant to use. The active agents need not be in solution to be effective. The active agents may be present wholly or in part as suspensions in aqueous solutions used as carriers to provide liquid compositions. The preparations are buffered as necessary to provide the appropriate pH.

Appropriate buffer systems include citric acid-citrate salts, acetic acid-acetate salts, and benzoic acid-benzoic salt systems. However, any buffer system commonly used for preparing medicinal compositions would be appropriate. While the vehicle used generally is primarily water, other vehicles may be present such as alcohols, glycols (polyethylene glycol or polypropylene glycol are examples), glycerin, and the like may be used to solubilize the active agents. Surfactants may include anionic, nonionic, amphoteric and cationic surfactants which are known in the art as appropriate ingredients for mouthwashes.

Liquid formulations may contain additional components to improve the effectiveness of the product. For example, component(s) may be added to increase viscosity to provide improved retention on the surfaces of the oral cavity. Suitable viscosity increasing agents include carboxyalkyl, hydroxyalkyl, and hydroxyalkyl alkyl celluloses, xanthan gum, carageenan, alginates, pectins, guar gum, polyvinylpyrolidone, and gellan gums. Gellan gums are preferred since aqueous solutions containing certain gellan gums may be prepared so that they will experience an increase in viscosity upon contact with electrolytes.

Some examples of the formulations of the composition disclosed herein include, for example, solid formulations such as tablets, capsules, granules, pills, troches, powders or suppositories, or liquid formulations such as syrups, elixirs, suspensions or injections, as well as aerosols, eye drops, ointments, ophthalmic ointments, emulsions, creams, liniments or lotions. These formulations may be prepared in accordance with conventional methods commonly used in the field of drug formulations.

In some embodiments, various additives which are commonly used in the drug formulation field, can be used. Such additives include, for example, saccharides such as lactose or glucose, a starch such as corn, wheat or rice, a vegetable oil such as soybean oil, peanuts oil or sesame oil, a fatty acid such as stearic acid, an inorganic salt such as magnesium metasilicate aluminate or anhydrous calcium phosphate, a synthetic polymer such as polyvinylpyrrolidone or polyalkylene glycol, a fatty acid salt such as calcium stearate or magnesium stearate, an alcohol such as stearyl alcohol or benzyl alcohol, a synthetic cellulose derivative such as methyl cellulose, carboxymethyl cellulose, ethyl cellulose or hydroxy-propylmethyl cellulose, or others such as water, gelatin, talc and gum arabic.

Further, in the case of a liquid formulation, it may be in such a form that at the time of use, it is dissolved or suspended in water or in other suitable medium. Especially when administration is carried out by e.g. intramuscular injection, intravenous injection or subcutaneous injection, a suitable medium for such an injection may, for example, be distilled water for injection, a hydrochloric acid lidocaine aqueous solution (for intramuscular injection), physiological saline, an aqueous glucose solution, ethanol, liquid for intravenous injection (such as an aqueous solution of citric acid and sodium citrate) or an electrolyte solution (for intravenous drip and intravenous injection), or a mixed solution thereof. Further, a buffer or a preservative may be added.

In some embodiments, for delivery into a cell, the composition disclosed herein can be formulated into liposomal preparations (e.g., liposomal suspensions or particles). Liposomal suspensions (including liposomes targeted to infected cells with monoclonal antibodies to viral antigens) are also preferred as pharmaceutically acceptable carriers. Methods for encapsulation or incorporation of compounds into liposomes are described by Cozzani, I.; Jori, G.; Bertoloni, G.; Milanesi, C.; Sicuro, T. Chem. Biol. Interact. 53, 131-143 (1985) and by Jori, G.; Tomio, L.; Reddi, E.; Rossi, E. Br. J. Cancer 48, 307-309 (1983). These may also be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Other methods for encapsulating compounds within liposomes and targeting areas of the body are described by Sicuro, T.; Scarcelli, V.; Vigna, M. F.; Cozzani, I. Med. Biol. Environ. 15 (1), 67-70 (1987) and Jori, G.; Reddi, E.; Cozzani, I.; Tomio, L. Br. J. Cancer, 53 (5), 615-21 (1986).

These formulations may contain usually from 0.001 to 100 wt %, preferably from 0.005 to 100 wt %, of the active ingredient in the case of the above-mentioned solid formulations, and may contain from 0.05 to 10 wt %, preferably from 1 to 5 wt %, in the case of other formulations.

A practically preferred dose of the compositions disclosed herein varies depending upon the type of the compound used, the type of the composition blended, the sex, age, weight, diseased degree and the particular section to be treated of the patient, but it is usually from 0.1 to 150 mg/kg in the case of oral administration and from 0.01 to 150 mg/kg in the case of parenteral administration, per adult per day. The number of times of administration varies depending upon the administration method and the symptom, but it is preferred to carry out the administration from one to five times per day.

As used herein, the terms "formulation" and "preparation" are used interchangeably.

Method of Use

Small molecules of invention and composition including the same can be used to treat or ameliorate any medical condition in a mammalian subject (e.g., a human patient) that can be treated or ameliorated by augmenting innate responses in the patient. Generally, such medical conditions can be treated or ameliorated by administering to the patient in need of treatment a small molecule of invention or a composition including the small molecule. In some embodiments, the small molecule can be a pharmaceutically acceptable salt or a prodrug thereof.

Medical conditions that can be treated or ameliorated by augmenting innate responses include, e.g., cancer or diseases caused by microbial pathogens, e.g., viral pathogens, bacterial pathogens, fungal pathogens, or disorders exacerbated by a pro-fibrotic or alternatively activated macrophages.

EXAMPLES

The embodiments of the present invention are illustrated by the following set forth examples. All parameters and data shall not be construed to limit the scope of the embodiments of the invention.

Example 1. Identification of Octahydro-1,6-naphthyridin-4-ones as Activators of Endothelium-Driven Immunity Via Diversity Through Phosphine Catalysis Introduction The synthesis and use of bioactive small molecules to gain insight into biological systems is a major facet of modern chemical biology (1) and several hypotheses regarding the most effective ways to increase the probability of discovering chemical probes of desired activity have been put forth (2-4). In this context, combinatorial chemistry emerged as the fastest way to generate a large number of candidate compounds (5, 6). However, early practices of large library synthesis and screening unveiled that the large number alone is not sufficient for increased hit rates and the structural diversity within the library may be important. The idea of generating a structurally diverse collection of compounds within a streamlined sequence of reactions has been elegantly formulated in the algorithms of diversity-oriented synthesis (DOS) (7-10). In this vein, a series of nucleophilic phosphine catalysis reactions has been developed, resulting in the production of twenty distinctive carbo- and heterocyclic scaffolds (Scheme 1; s1-s20). Scheme 1 illustrates diversity-oriented synthesis based on nucleophilic phosphine catalysis. For clarity, detailed designation of stereochemistry and substituents are removed. For the detailed structural information, see the following references: For scaffold s1, (11, 12); s2, (13, 14); s4, (15); s5, (16); s6, (17, 18); s7, (19); s8, (20); s9-s12, (21); s13-s20, (22); s21-s23, (23); s24-s39, (24).

The goal in developing new reactions was to provide new heterocyclic frameworks that deviate from the relatively limited pool of molecular motifs used by pharmaceutical companies. For allenes, one-step ring forming reactions were carried out using either commercially available or otherwise readily available imines, maleimides, aldehydes, aziridines, and electron-deficient

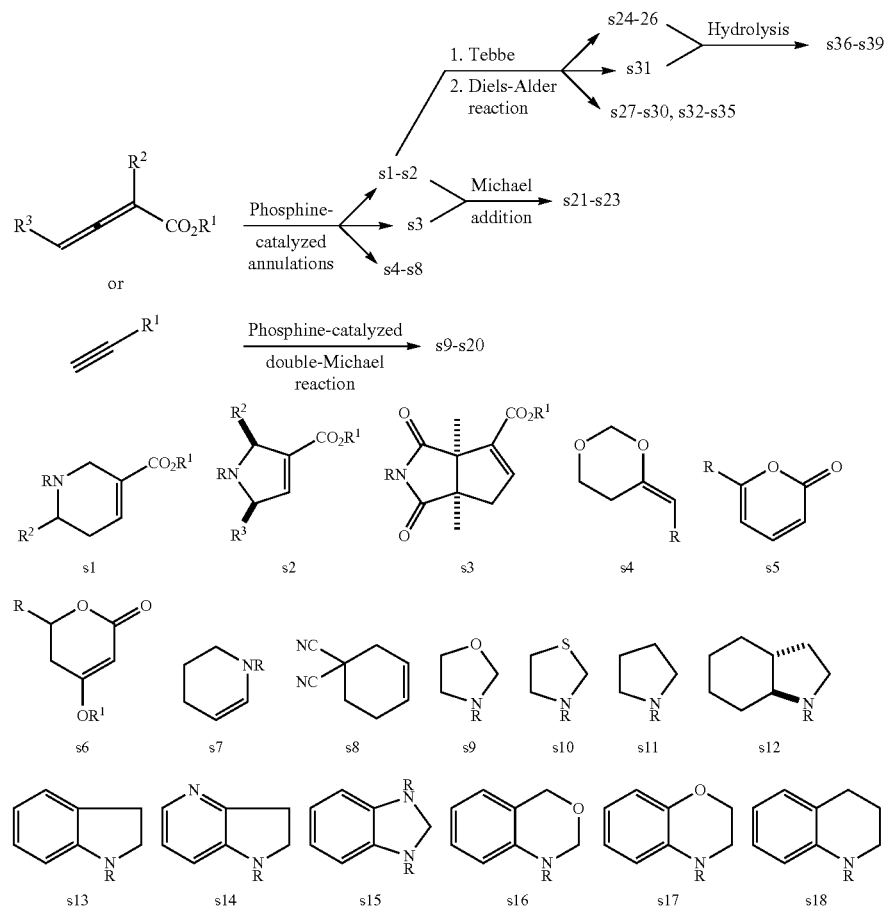

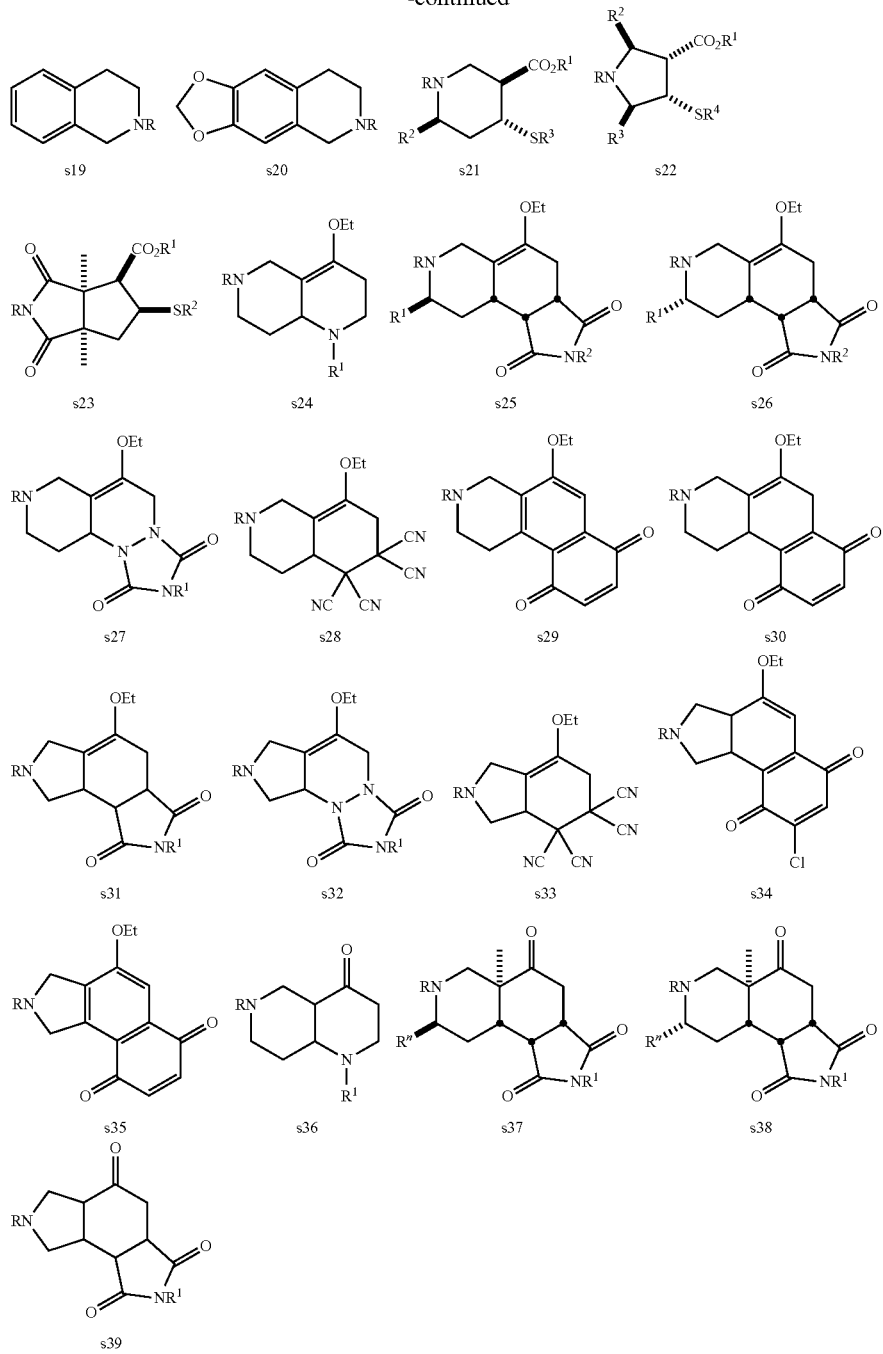

olefins, resulting in scaffolds s1-s8 (11-20). For electron-deficient acetylenes, a one-step double-Michael reaction with readily available dinucleophiles was effected by a diphenylphosphinopropane (DPPP) catalyst, providing heterocyclic frameworks s9-s20 (21, 22). The α,β-unsaturated ester functionality in tetrahydropyridine s1, dihydropyrrole s2, and bicyclic succinimide s3 was further utilized in a highly diastereoselective Michael addition of thiols to produce piperidine s21, pyrrolidine s22, and bicyclic succinimide s23 (23). The carbonyl group of the α,β-unsaturated ester was also methylenated using Tebbe reagent to provide alkoxy dienes, which upon exposure to dienophiles (imines, maleimides, triazolinediones, tetracyano ethylene, and benzoquinones) underwent diastereoselective Diels-Alder reaction and produced multicyclic compounds s24-s35 (24). A stereoselective hydrolysis of the enol ether group in the Diels-Alder adducts further produced multicyclic ketones s36-s39. The library of 642 compounds of thirty-nine distinctive scaffolds was tested in several bioassays and resulted in the identification of geranylgeranyltransferase type I (GGTase I) inhibitors (25, 26), RabGGTase inhibitors (23), and antimigratory compounds (24). These outcomes powerfully demonstrate the premise behind DOS—the more structural diversity in the screening collection, the higher the probability of discovering small molecule biomodulators. Therefore, the nucleophilic phosphine catalysis-based synthesis resulted in a compound library with rich structural diversity, well-poised to probe critical biological questions.

In order to most efficiently interrogate compound libraries, high-throughput screening systems to detect compounds with pre-specified molecular targets have been developed. However, with few exceptions, a limitation of current screens is that they do not integrate the interactions that occur between heterogeneous cell types involved in disease pathogenesis (27,28). We aimed to establish a biological platform amenable to high-throughput screening, but with sufficient complexity to identify molecular probes that resulted in (a) endothelial cell activation and (b) subsequent EC-triggered induction of innate immune responses. Activation of the endothelium occurs when pro-inflammatory cytokines such as interferon gamma (IFNγ) induce the production of chemokines and expression of cell adhesion molecules on the endothelial surface. Consequently, leukocytes home to activated endothelium and transmigration ensues. Such activation of the endothelium is a physiologic and necessary process, desirable for eradicating infections and some cancers (29-31).

Despite the homeostatic benefits of endothelial cell activation in host defense, such activation also plays a central role in the pathogenesis of many chronic inflammatory disorders (32); this has resulted in chemical screens predominantly focused on the identification of compounds that decrease endothelial cell inflammation (33-37). In stark contrast, far less effort has been put forth to understand the underlying networks by which compounds may activate or inflame the endothelium. Yet, such insights may have important implications for understanding salutary and maladaptive aspects of inflammation at the vessel wall. Furthermore, given that an increasing number of drugs have been removed from the market as a result of cardiovascular complications (38-41), understanding how small molecules may promote inflammation in the vasculature is an important question.

Results

Identification of Small Molecules that Activate Endothelium

Figure 3:
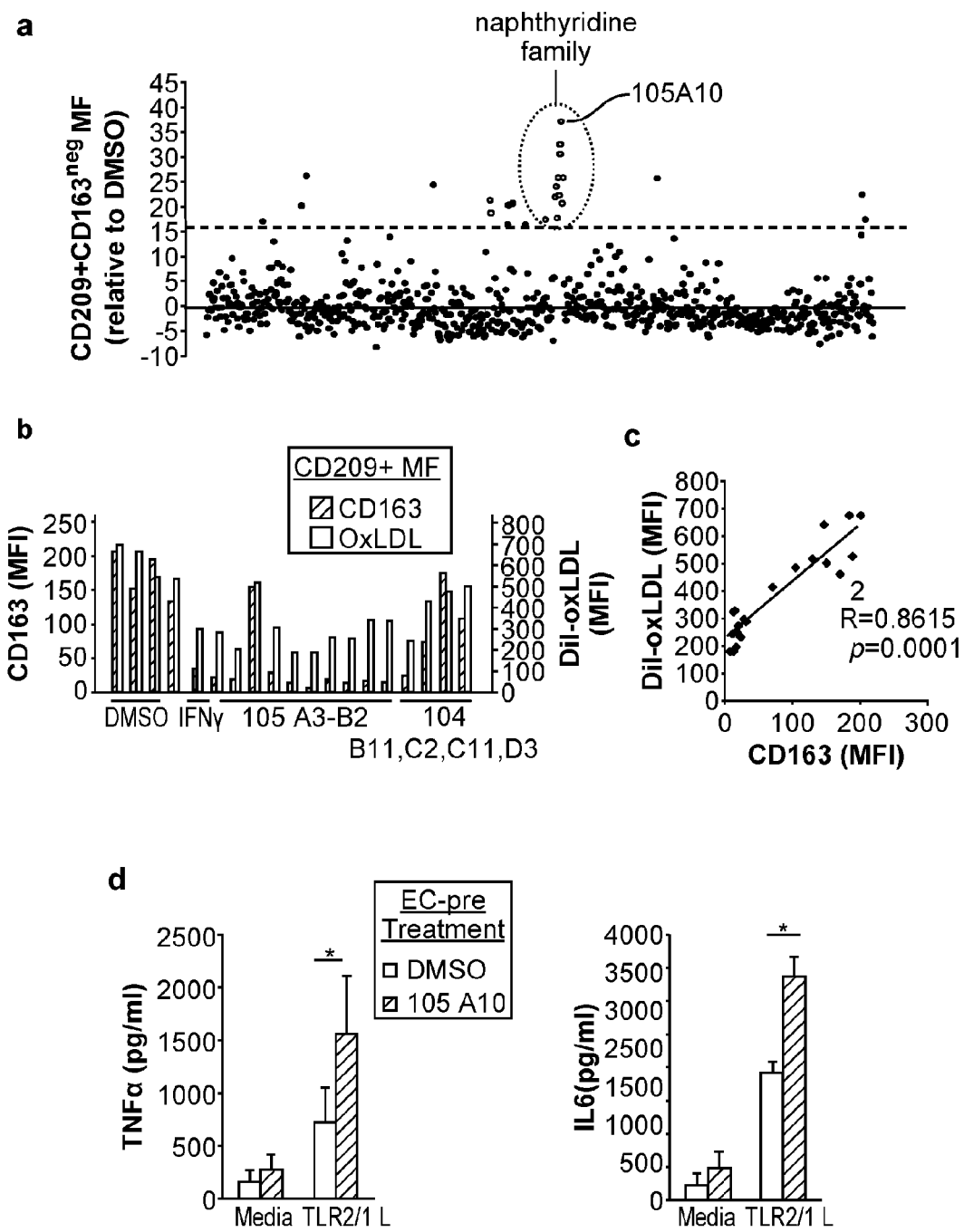
FIG. 3A shows small molecule screen (n=642) was performed to identify compounds that mimicked IFNγ, as determined by their capacity to polarize the endothelium to trigger monocytes to become inflammatory (CD209+ CD163−) MF. * represents the naphthyridine family of compounds (9 of 10 were "hits"). Dashed line represents 3 s.d. from DMSO mean.
FIGS. 3B, 3C, and 3D shows results of tests by which selected compounds from two structurally distinct families were validated; like IFNγ, EC polarized by such compounds also drive monocytes to differentiate into MF that are less phagocytic, as determined by diI-oxLDL uptake, but more responsive to TLR stimulation, as determined by CBA (*, p value <0.01).
Figure 4:
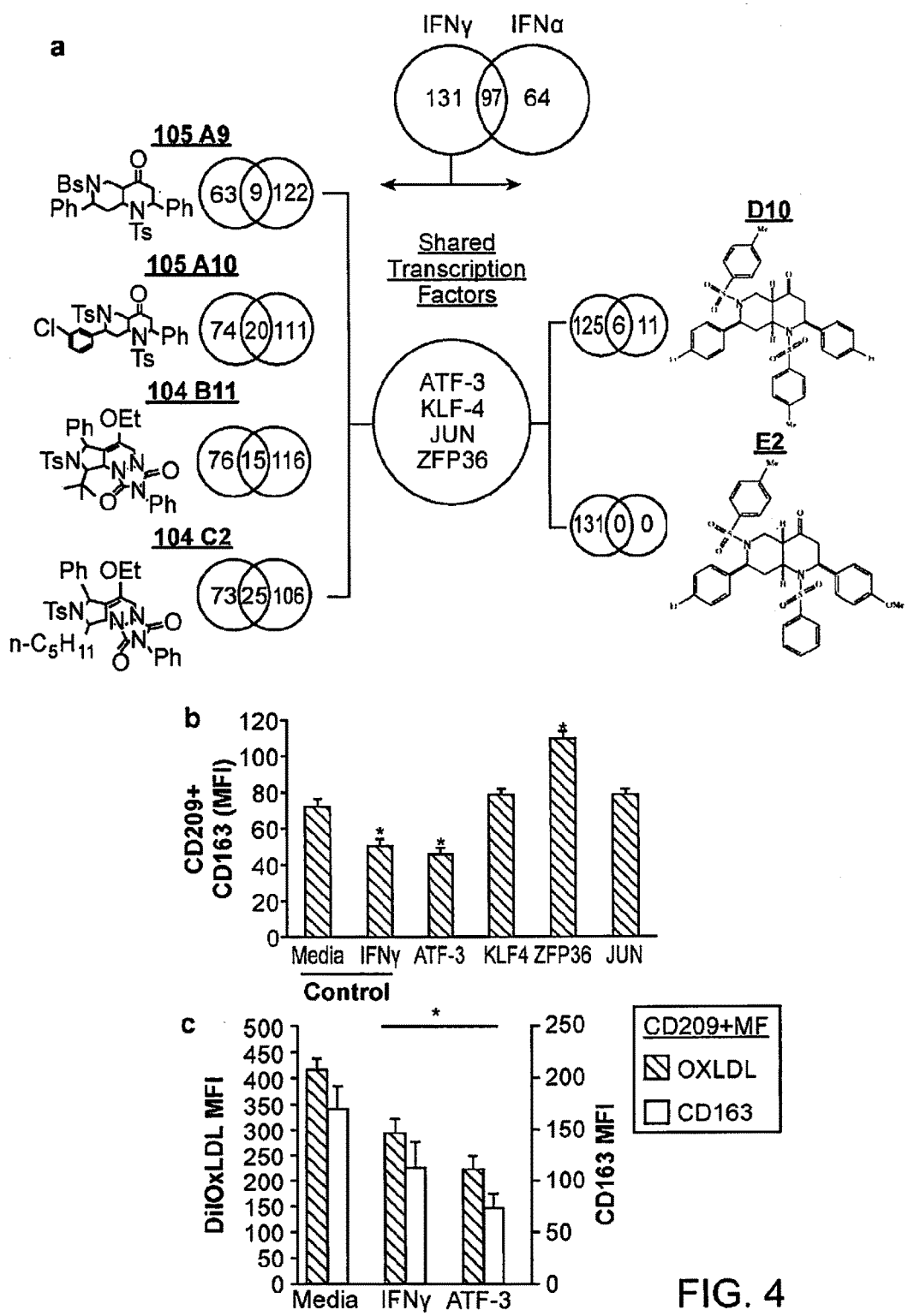
FIGS. 4A-F shows results tests of defining key regulatory gene networks by which naphthyridines and IFNγ regulate innate immunity. (A) Transcriptome profiling of active and inactive biological/chemical stimuli were compared, in search of transcription factors (TF) induced (>1.25 fold over DMSO) by active, but not inactive perturbations. IFNγ and IFNα are structurally similar members of the IFN family, with differing capacity to polarize the EC. 105A9, A10 are naphthyridines, and D10 and E2 are active and inactive analogues, respectively, of 105A10. 104 B11, C2 belong to another EC-activating family of compounds. (B-D) Of the 4 candidate TF, only ATF3 polarizes the EC to trigger inflammatory MF. (E) siRNA against ATF3 prevents IFNγ-mediated EC polarization. (F) Gene expression analysis in EC with forced expression of ATF3 vs. empty control vector (triplicate wells, fold change >1.4 or <0.6, p-value <0.05) was performed, and induced genes were analyzed by Ingenuity Pathway analysis; ATF3 overexpression leads to an enrichment of "IFN signaling" network, indicating that it is one mechanism by which compounds engage IFN pathways.
Figure 4:
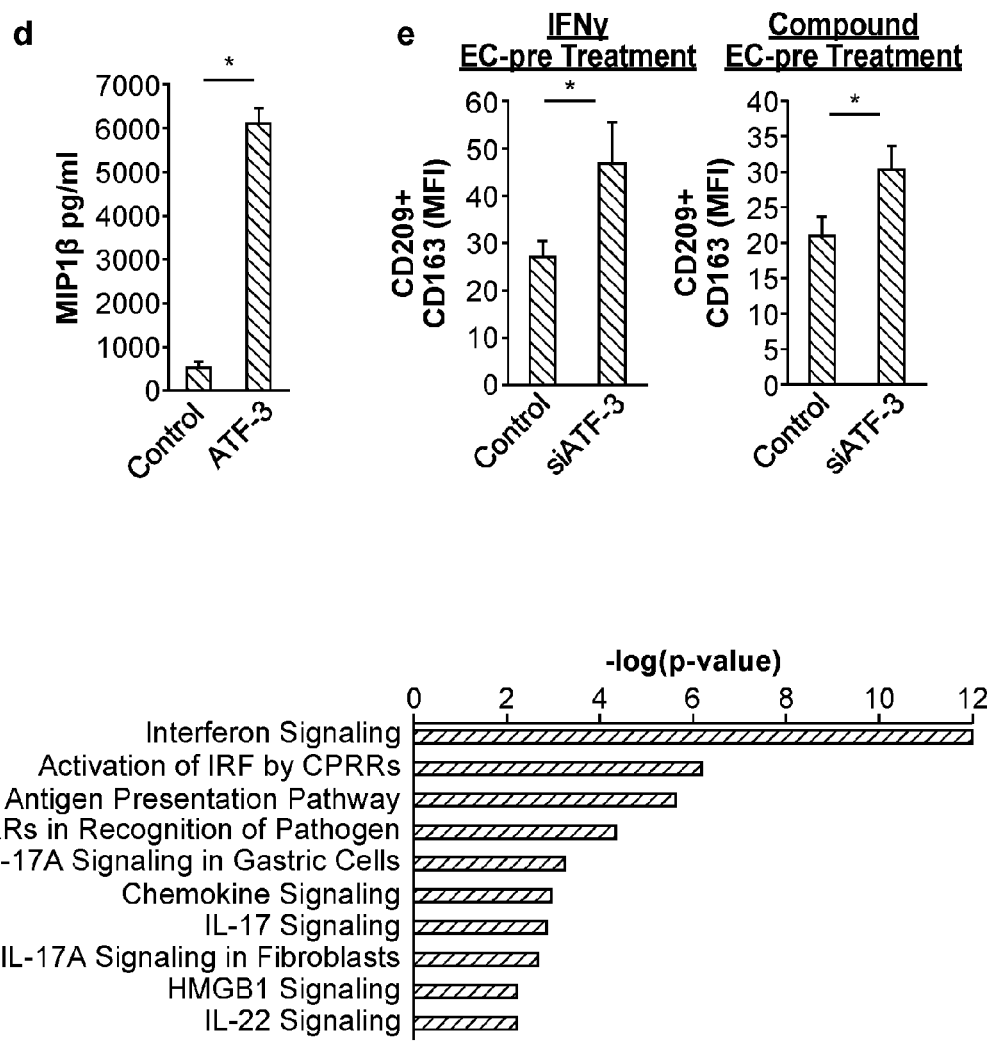
Figure 5:
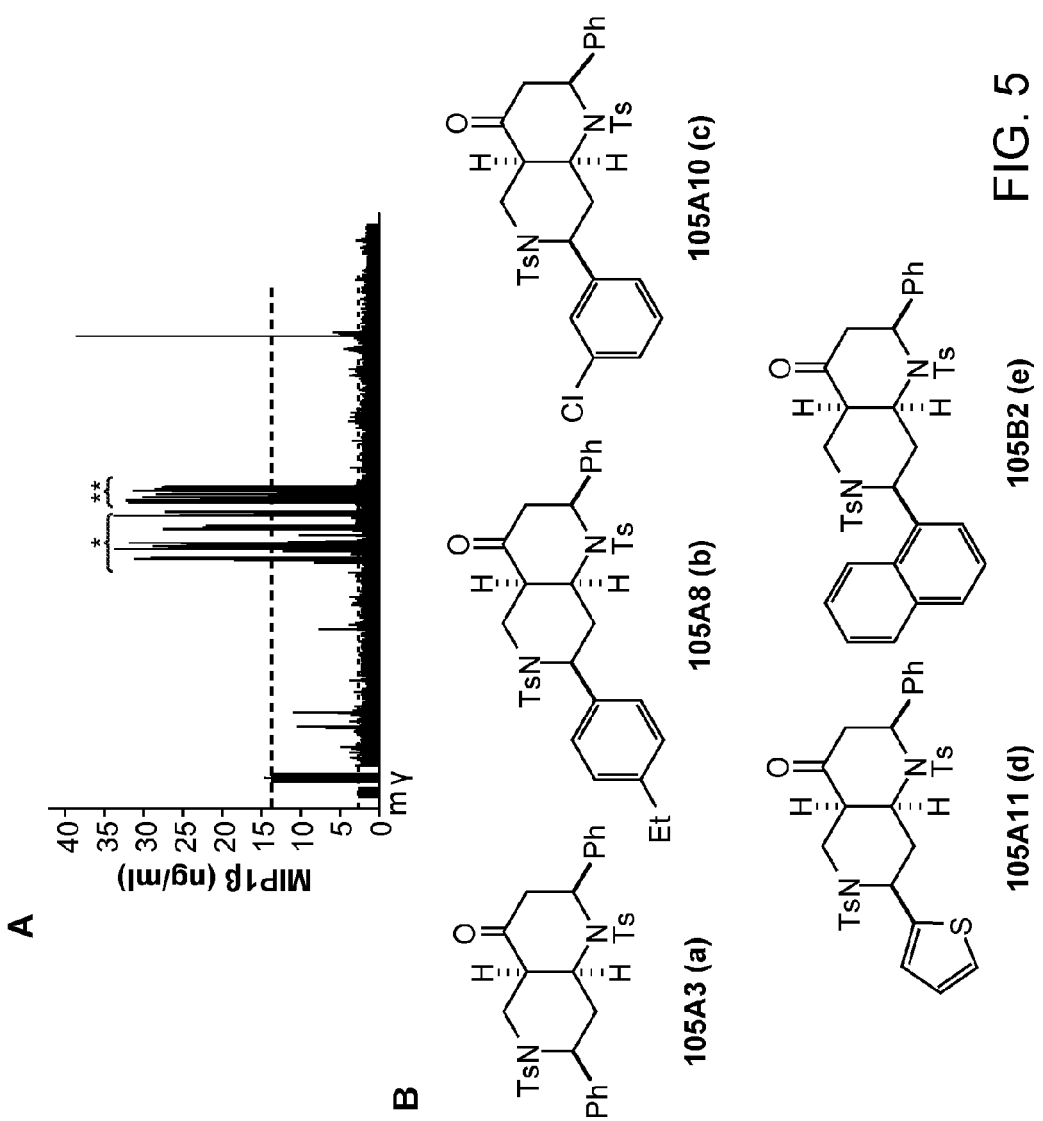
FIGS. 5A-5D show identification of small molecules that activate human endothelial cells. (A) IFNγ (10 ng/ml), DMSO controls (n=60 total replicates) and 642 compounds (10 μM) were tested for their ability to promote MIP1β production. The library contained 37 compounds capable of inducing MIP1β at least to the level of IFNγ (dashed line). * represents five distinct scaffolds with activity, while ** represents the two naphtyridine families. (B) Structures of five octahydronaphtyridinones selected for further study. (C) Confirmation of a subset of active compounds: co-culture is required for MIP1β production. Data represents mean+−s.e.m. of triplicate wells from one of two comparable experiments. # p-values for MIP1β: (a) 105A3=0.008, (b) A8=0.003, (c) A10=0.026, (d) A11=0.007, (e) B2=0.046. ## p-values for MIP1α: (a) 105A3=0.042, (b) A8=0.016, (c) A10=0.009, (d) A11=0.041, (e) B2=0.13. (D) Activated endothelium triggers MIP1β production from CD14+ monocytes. Percent positive MIP1β cells and mean fluorescence intensity (MFI) of MIP1β+ cells are shown.
Figure 5:
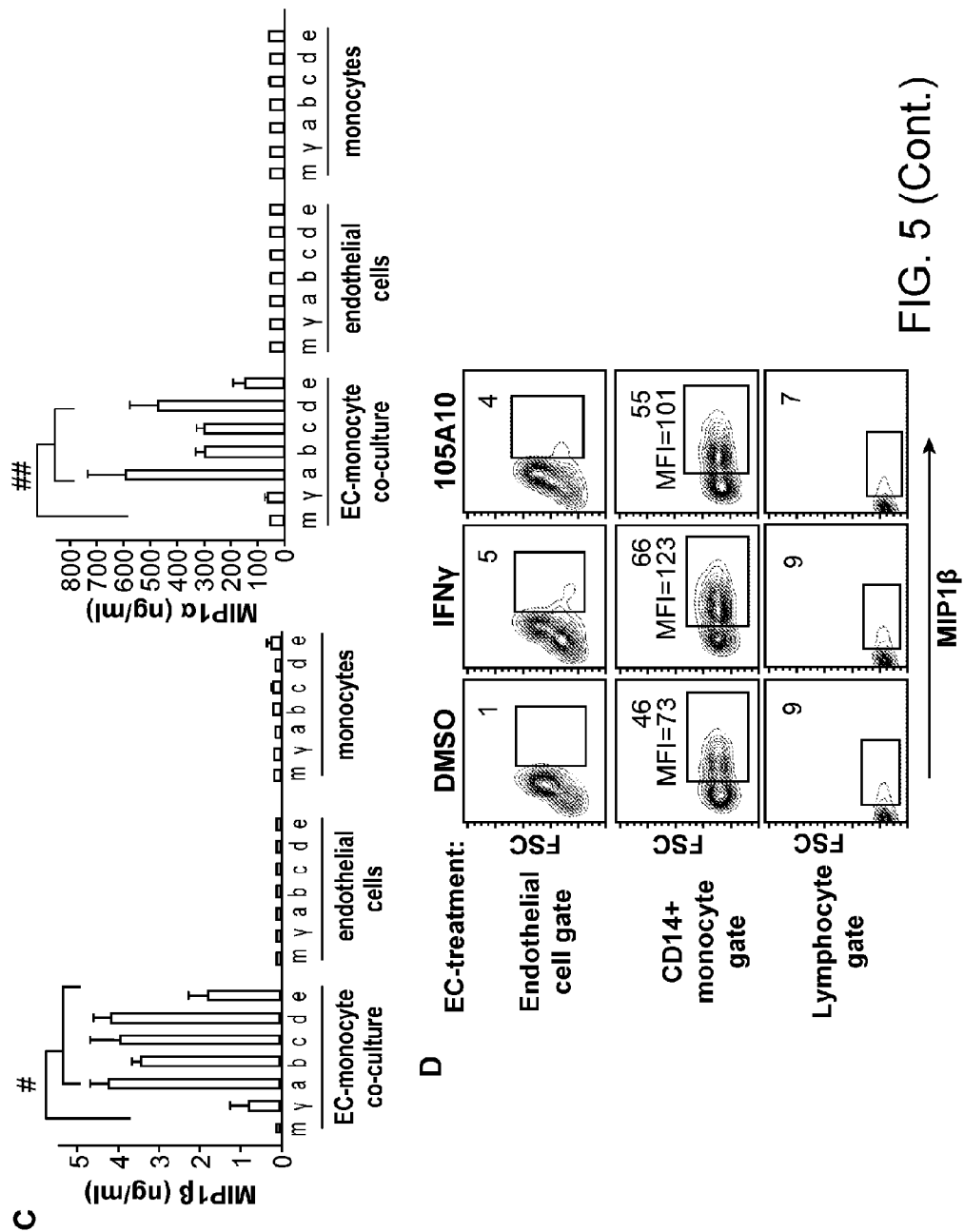

Activation of the endothelium is intricately linked to innate immunity. For example, EC activated by IFNγ were shown to trigger the production of macrophage inflammatory protein 1 alpha (MIP1α) from primary human monocytes (42). Interestingly, neither EC nor monocytes treated with IFNγ produced this chemokine; co-culture between the activated EC and monocytes was required. Therefore we hypothesized that compounds that "activate" the endothelium could be identified indirectly—endothelium encountering activating compounds would gain the capacity to trigger chemokine production by monocytes. To test this hypothesis, we designed an EC-monocyte co-culture system amenable to high-throughput compound screening (FIG. 9A). In this platform, MIP1β production, rather than MIP1α or IL8, proved to be the most reliable marker of EC activation by IFNγ (FIG. 9B). Subsequently, EC were treated with DMSO (vehicle control), IFNγ (EC-activation control), and a collection of 642 compounds (final concentration, 10 M) (FIG. 9C). Of the 642 compounds, 37 (5.8%) promoted MIP1β production (FIG. 5A). By contrast, IFNγ-treated EC inhibited IL-8 production from monocytes; likewise, every EC-activating compound also decreased IL8 production (FIG. 10A). MIP1α was not induced by IFN-treated EC; however, most compounds that induced MIP1β also induced MIP1α production (FIG. 10B).

Intriguingly, most EC-activating compounds (35 out of 37; see compounds 104A5 to 301C3 described above) possess the scaffolds derived from the sequence of phosphine-catalyzed annulation, Tebbe methylenation, Diels-Alder reaction, and sometimes hydrolysis (scaffolds s24-s27, s31, s32, and s36 in Scheme 1). As reported earlier (24), tetrahydropyridine s1 and pyrrolidine s2 were formed through the phopshine-catalyzed [4+2] and [3+2] annulation reaction between allenoates and imines (11-14) and converted into the corresponding ethoxy dienes via Tebbe reaction. The subsequent Diels-Alder reaction of the dienes with maleimides, N-phenyl triazolinedione, and N-sulfonamido arylimines provided multicyclic enol ethers s24, s25/s26, s27, s31, s32, each of which provided 9, 5, 5, 3, and 8 hits out of 10, 12, 5, 9, and 10 compounds, respectively, in confirmatory experiments (FIG. 11). The enol ether adducts s24, s25/s26, and s31 were stereoselectively hydrolyzed into the corresponding ketones s36, s37/s38, and s39. While ketones s37/s38, and s39 did not provide any EC-activating compounds, all 10 of the octahydro-1,6-naphthyridin-4-ones were active. The octahydro-1,6-naphthyridine framework was particularly interesting in that it exhibited the highest hit rate and the solid-phase split-and-pool synthesis of the octahydro-1,6-naphthyridin-4-one analogs should be possible by using resin-bound allenoates (vide infra).

With the anticipation of the analog synthesis, five octahydro-1,6-naphthyridin-4-ones were selected for further validation (FIG. 5B). Direct treatment of independent EC or PBMC with these activating compounds did not result in significant production of MIP1β or MIP1α; as with IFNγ, co-culture of activated EC and PBMC was required for chemokine induction (FIG. 5C). Intracellular flow cytometry of co-cultures revealed that when PBMC are added to EC activated either by IFNγ or an octahydro-1,6-naphthyridin-4-one 105A10, the CD14+ monocytes, rather than EC or lymphocytes, are the dominant producers of MIP1β (FIG. 5D). This underscores the finding that a screen testing isolated endothelial cells or monocytes would have missed this novel class of EC-activators. Therefore, like IFNγ, this novel family of compounds mediates EC-triggered induction of innate immune activation.

Synthesis of Naphthyridinone Analogs

The discovery of promising chemical probes capable of promoting a robust innate immune response through the activation of the endothelium warranted the development of efficient and rapid synthesis of analogs, allowing for determination of structure-activity relationship (SAR). We envisioned a short, modular synthetic route using SynPhase lanterns as the solid support (Scheme 2). Establishment of the solid phase synthesis began with the coupling of the Wang resin 3 with 2-methyl-2,3-butadienoic acid (2) and the subsequent phosphine-catalyzed [4+2] annulation of resin-bound allenoate 4 with N-tosylbenzaldimine (25). The resin-bound tetrahydropyridine 5 was treated with Tebbe reagent and anhydrous pyridine in THF and converted into the dienol ether 6. To test the efficiency of the Tebbe reaction, the enol ether 6 was cleaved off the resin using trifluoroacetic acid (TFA, 2.5%) in dichloromethane (DCM). Because there are very few successful examples of Tebbe reaction in the solid phase (43, 44), we were pleased to find the methylenation of the polymer-supported α,β-unsaturated enoate 5 proceeded smoothly in good yield; enone 6' was obtained in 53% overall yield over 4 steps and excellent purity (>95%, $^1$H NMR). The subsequent endo-selective Diels-Alder reaction with N-tosylbenzaldimine in toluene at 80° C. gave octahydro-1,6-naphthyridine 7, which was hydrolyzed off the resin using 2.5% TFA in DCM to provide octahydro-1,6-naphthyridin-4-ones 1a and 1a' in 38% overall yield with high diastereoselectivity (dr=97:3) after chromatographic purification. The structures of both compounds 1a and 1a' were unequivocally established through x-ray crystallography. X-ray crystallography revealed that the tetrahydropyridine (11) and the octahydronaphthyridine (24) featured anti relationships between their C7-phenyl and N6-tosyl groups. Interestingly, the imine dienophile approached the diene 6 from the opposite face of the N6-tosyl group. It is also noteworthy that the hydrolysis of the enol ether produced octahydronaphthyridinone 1a and 1a' featuring a cis-fused [4.4.0] bicyclic framework.

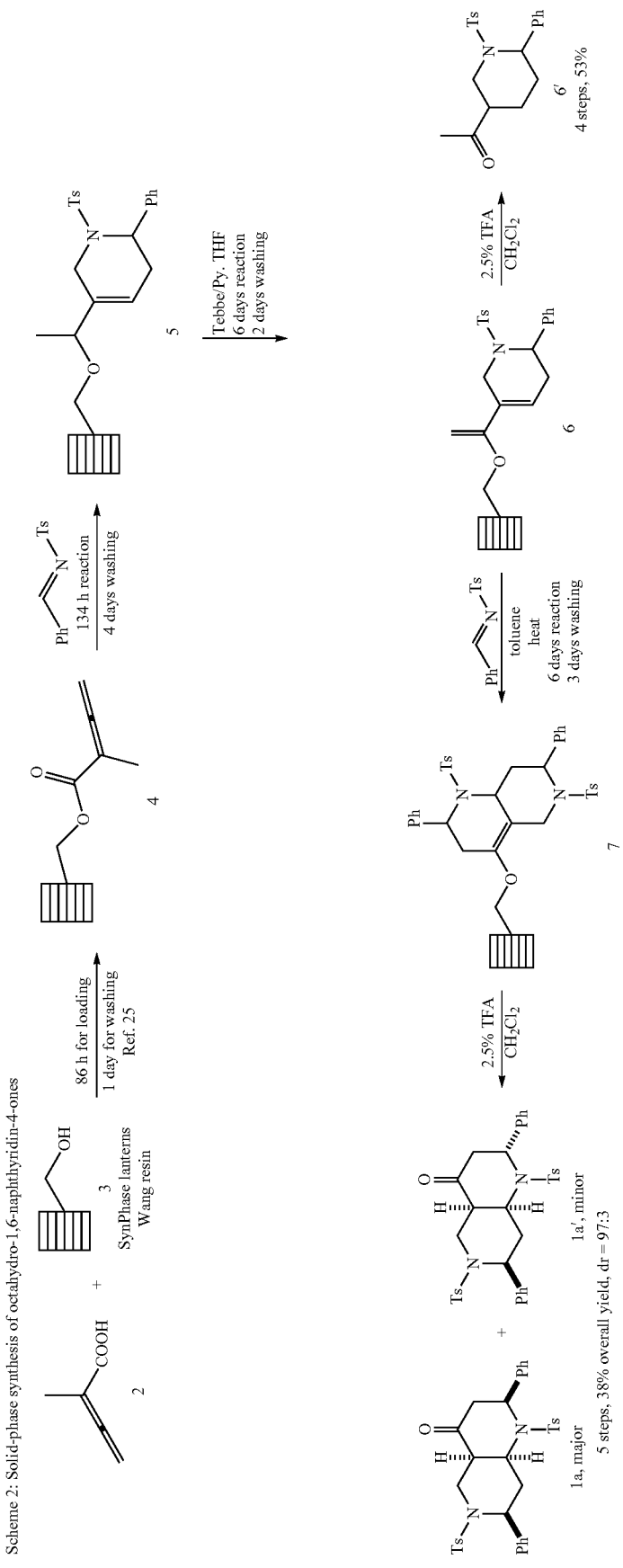

Having successfully established the solid-phase reaction conditions, next we prepared the N-sulfonylimine building blocks. According to the result of phosphine-catalyzed [4+2] annulation of resin-bound allenoates from our previous work (25), we chose ten N-sulfonylimines, which provided excellent reaction yields (87-108%) and purities (80-99%) (FIG. 12). It is noteworthy that the strategy of our combinatorial library construction is very efficient in terms of building blocks because the N-sulfonylimines were used in both phosphine-catalyzed [4+2] annulation and the Diels-Alder reaction. With the building blocks in hand, the library synthesis commenced. The individual lanterns were tagged with colored spindles and cogs to encode the imine building blocks of the [4+2] annulation used for each lantern. Since the Diels-Alder reaction was the last split step of the synthesis, tagging for the imine building blocks of the Diels-Alder reaction was not necessary. By using the tagging and split-and-pool combinatorial techniques, 2-methyl-2,3-butadienoic acid and ten N-sulfonylimine building blocks resulted in the preparation of one hundred (1×10×10) octahydro-1,6-naphthyridin-4-one analogs. The overall yields are up to 39% in 5 steps and the purities of the final products are up to 99% after the prep HPLC purification.

At the same time, additional octahydro-1,6-naphthyridine analogs with different functional groups were synthesized in the solution phase (Scheme 3) for the further SAR analysis. The octahydro-1,6-naphthyridin-4-one analogs 11a-11ab with different substituents, Ar, R, Ar' and R', were synthesized according to procedures reported previously (Scheme 3A) (24). For the preparation of an octahydronaphthyridinone without the C7-substituent, a new sequence of reactions was designed (Scheme 3B). The commercially available ethyl 4-piperidone-3-carboxylate hydrochloride (12) was protected with p-toluenesulfonyl (tosyl, TS) group and the ketone was chemoselectively reduced with sodium borohydride ($NaBH_4$). Methanesulfonyl(mesyl)ation of the resulting alcohol and β-elimination of the mesylate provided tetrahydropyridine 14. The Tebbe methylenation, Diels-Alder reaction with N-sulfonyl benzaldimine, and acid hydrolysis gave the desired product H6. To probe the importance of the C4-carbonyl group, the corresponding alcohol and its ethyl ether were also prepared (Scheme 3C). The DIBAL reduction of compound 105A10 gave the alcohol 2B6, which in turn was O-alkylated to the ethyl ether 2B7. Naphthyridinone without the N1-substituent was also prepared (Scheme 3D). To prepare tetrahydronaphthyridine G9, octahydronaphthyridine 15 was subjected to the Fukuyama's denosylation condition (45) followed by morpholinesulfonyl chloride and triethylamine for aromatization (46).

Scheme 3: Solution-phase synthesis of octahydro-1,6-naphthyridin-4-ones.

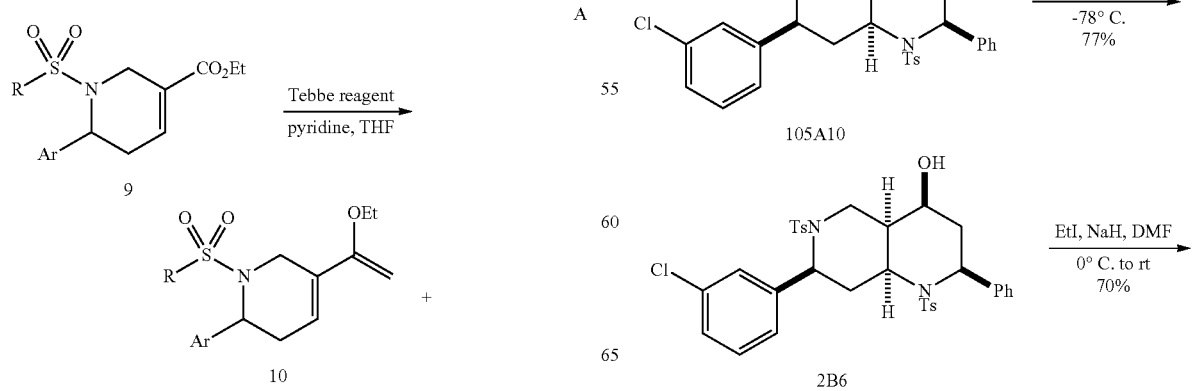

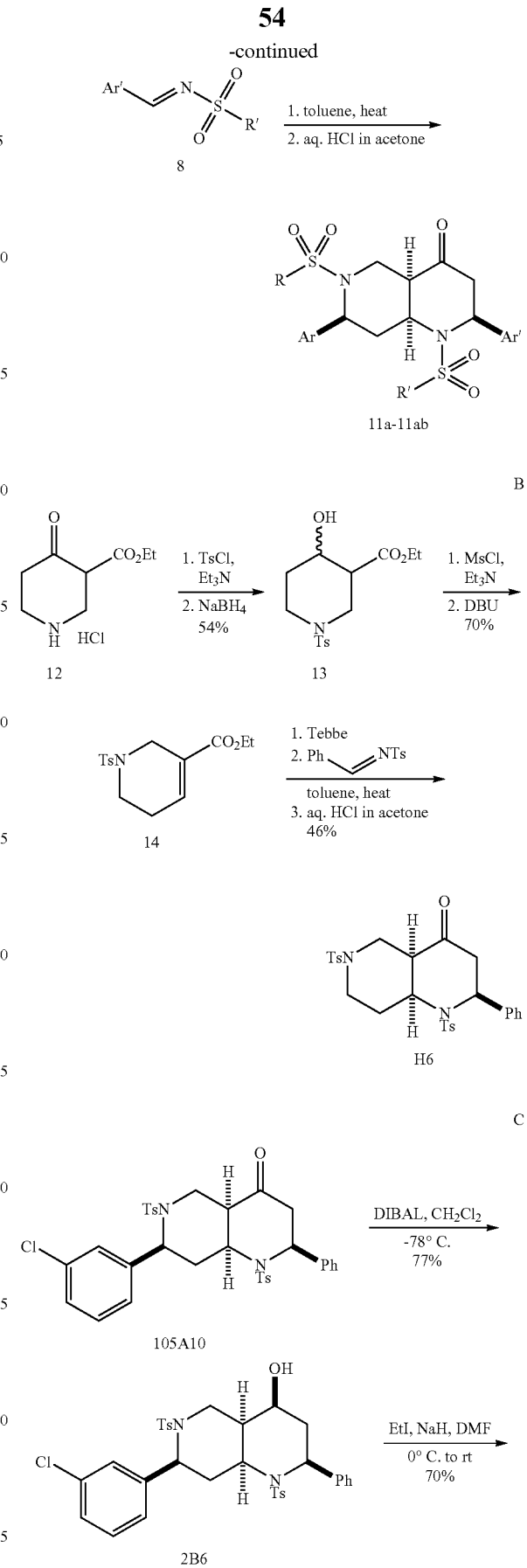

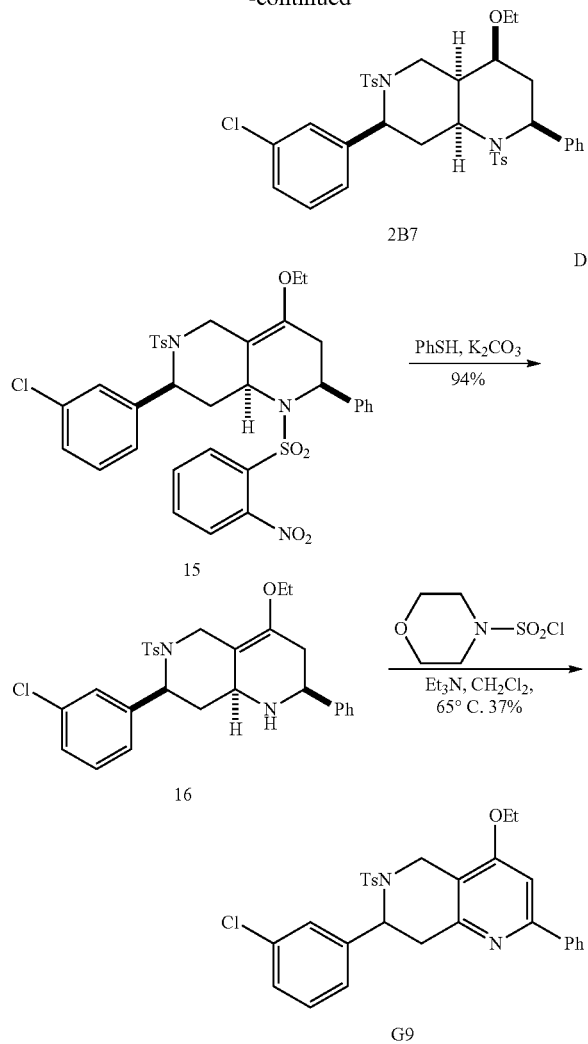

Structure Activity Relationship (SAR)

Figure 6:
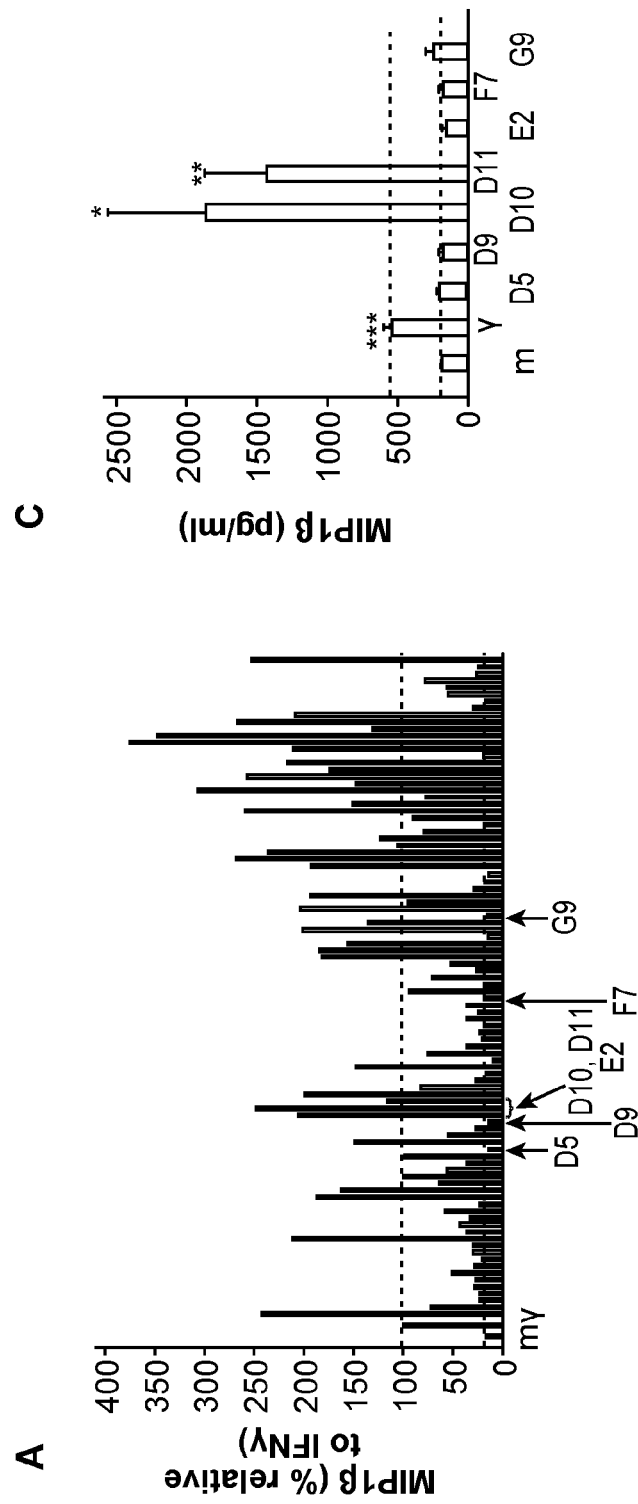
FIGS. 6A-6C show EC-activating effects of 96 naphthyridinones. (A) Data represents percent induction relative to IFNγ for each of the 96 analogs analyzed over two experiments. (B) Structures of selected active (H6, 2B6, 2B7, 105A3, D6, A10, D10, D11, E3, C2, C8 and C9) and inactive octahydro-1,6-naphthyridin-4-one analogs (H11, 2B2, D5, D9, E2, E8, F7, F10 and G9). (C) Validation of 7 (active and inactive) analogs. Data represents the mean±s.e.m. from two independent experiments performed in triplicate wells (n=6 wells per condition), * p-value<0.05,  p-value<0.03, * p-value<0.003.
Figure 6B:
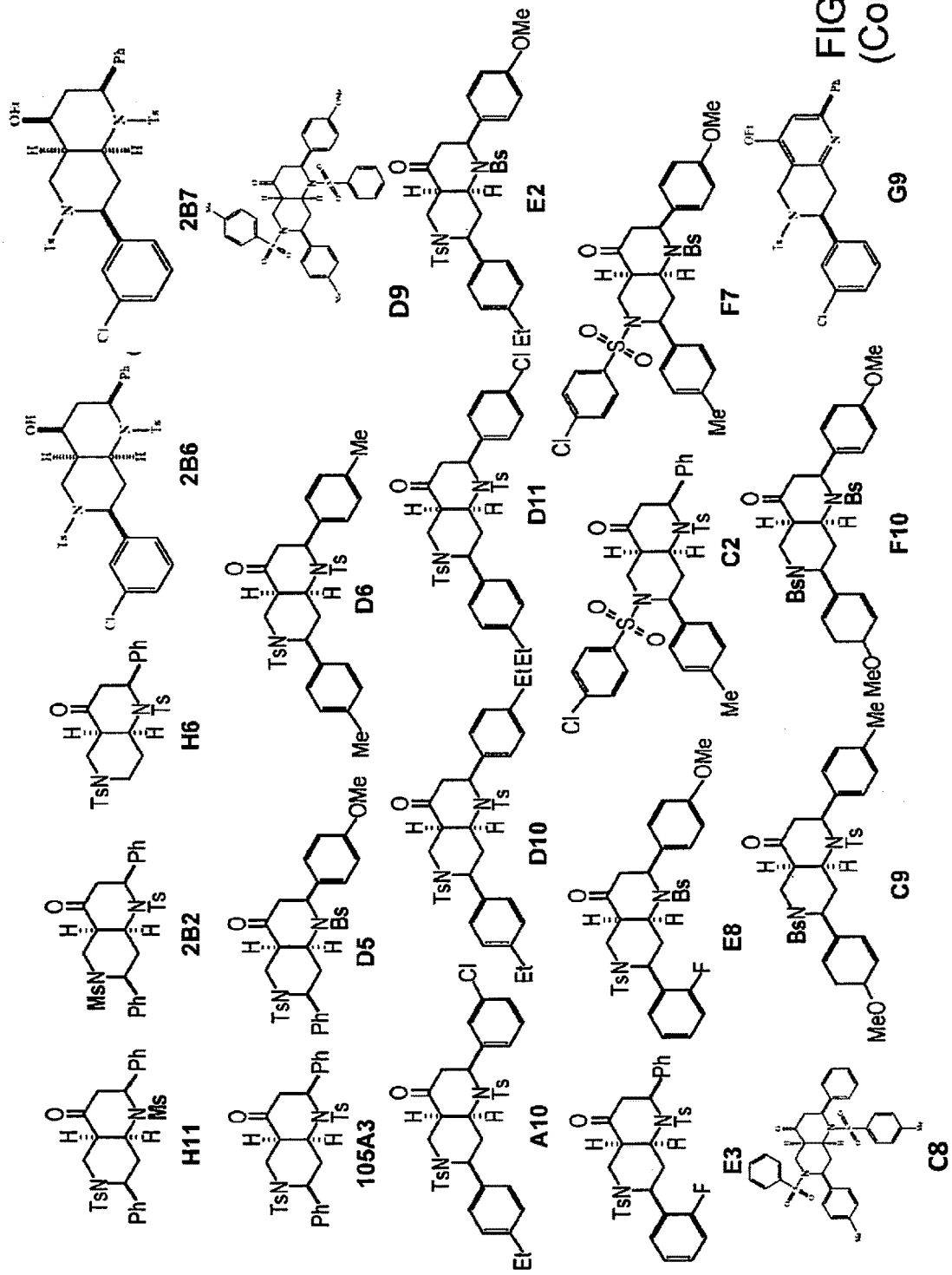

With the synthesis of analogs from the solid phase and the solution phase completed (see compounds A2 to 2B7 described above), the products were dissolved in DMSO and analyzed for EC activation. Since the original ten naphthyridinones were all EC-activating, the hope was that the SAR studies would reveal structural elements that obliterate EC-activating effects and thereby pinpoint the crucial motifs for the biological activity. Indeed, the focused library of 96 analogs produced compounds with distinct capacities for EC activation (FIG. 6A), indicating some essential structural features for the biological activity of the octahydro-1,6-naphthyridin-4-ones. In particular, the aryl groups on the N1- and N6-arylsulfonly groups were indispensable; both N1-mesyl (Ms) and N6-mesyl naphthyridinone compounds (H11 and 2B2, FIG. 6B) lost their activity. Based on the fact that the N1-mesylated naphthyridinone was inactive, it was not surprising to find that the derivative G9 with the pyridine ring was inactive as well. On the other hand, removal of the C7-aryl group (analog H6) did not affect the naphthyridinone's EC-activation. As we discovered in the initial screening, both enol ether (s24 in Scheme 1) and ketone octahydronaphthyridines (s36 in Scheme 1) were active, indicating that ketone group is not essential for the activity. Although we speculated that the tetrasubstituted enol ether functionality is intact under physiological conditions based on the fact that ketones (s37-s39) of EC-activating cool ethers (s25, s26, and s31) were not active, we wanted to confirm that the naphthyridinones are by no means acting as covalent modifiers through Schiff base formation. Indeed, alcohol 2B6 and its ethyl ether 2B7 were active, confirming that the ketone group was less essential for naphthyridinone's EC-activating effect. The solid-phase split-and-pool Synthesis provided a large number of active and inactive analogs that contain various substituents, around the benzene rings of N1- and N6-arylsulfonyl as well as C2- and C7-aryl groups. One subtle yet powerful observation was that naphthyridinones D5, D9, E8, F7, and F10 (except analog E2) bearing N1-benzenesulfonyl and C2-p-methoxyphenyl group did not exhibit EC-activation, while various naphthyridinones with the same N6- and C7-substituents retained their activity (FIG. 6B). Based on its structure, analog E2, which appeared to have some activity in the initial test (FIG. 6A), was predicted to behave more like the inactive analogs; indeed, confirmatory studies revealed it was relatively inactive (FIG. 6C). Although some synergistic substituent effects obscured a clear cut SAR. useful patterns emerged (FIG. 7). The predictive power of the SAR data illustrates the advantage of having a diverse and significant number of analogs, which was only possible because of the short and efficient synthetic route based on the solid phase nucleophilic phosphine catalysis.

Figure 8:
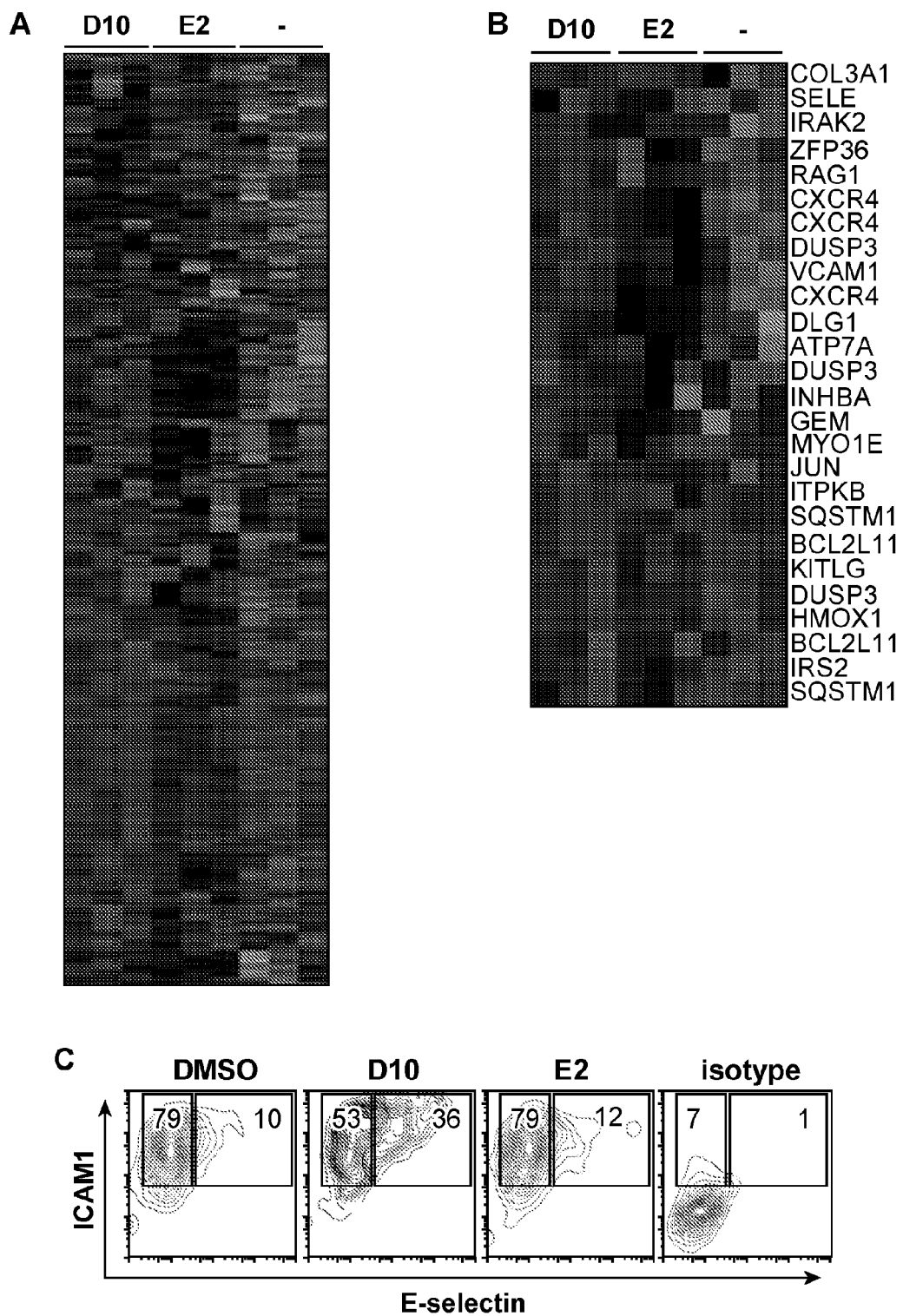
FIGS. 8A-8C show gene expression profiling of endothelial cells treated with active and inactive analogs. (A) Microarray analysis comparing gene expression induction in EC treated with active analog (D10, 10 μM) and inactive analog (E2, 10 μM). (B) Subset of genes from A with known involvement in inflammation: relative expression by active and inactive analogs. (C) E-selectin induction by naphthyridinone analogs. Percentages for ICAM and ICAM/E-selectin expressing cells are displayed.

Based on the disparate biological activities of D10 and E2, we predicted that these two structurally similar molecules would induce distinct gene networks involved in EC activation. To test this idea, we performed transcriptome profiling in EC treated with active (D10) and inactive (E2) analogs. In comparison to vehicle control, the EC-activating analog D10 induced 201 gene probes (fold change >1.25, p-value <0.05), while the inactive analog E2 activated only 49 gene probes (FIG. 8A). Remarkably, despite their structural similarity, the two analogs induced distinct sets of genes: only 2 genes were shared in common between the two analogs. More specifically, genes involved in the regulation of immune processes were more frequently induced by D10 than E2 (FIG. 8B). The induced genes were additionally analyzed by Ingenuity Pathway Analysis; in total, 32 canonical pathways were engaged by the active analog, and 10 of the top 20 canonical pathways are implicated in inflammation, including: atherosclerosis signaling (p<0.03), IL8 signaling (p<0.006) and high mobility group-box1 (HMGB1) signaling (p<0.004). By contrast, E2 did not activate any networks related to immune regulation. Of particular interest, E-selectin was found to be uniquely induced by the active, but not by the inactive analog. This adhesion molecule plays a critical role in leukocyte rolling and firm adhesion to activated endothelium, and is implicated in chronic inflammatory diseases (47, 48). To confirm this finding at the protein level, EC were treated with active or inactive analogs and E-selectin expression was measured by flow cytometric analysis. In comparison to vehicle control, only the active analog D10 markedly enhanced E-selectin expression levels (FIG. 8C). Therefore, despite subtle structural changes, these two naphthyridinones display distinct effects on EC activation and disparate gene expression profiles. Together, this work demonstrates how a DOS approach can be combined with screening platforms of adequate complexity, along with transcriptome profiling, to provide a framework for understanding complex biological processes, such as EC-triggered innate immunity.

Discussion

The endothelium is perpetually exposed to systemic chemical and mechanical stressors, such as infection, hypertension, smoking, and diabetes-cardiovascular risk factors known to cause endothelial inflammation (49, 50). This is intricately linked with the induction of chemokines and adhesion molecules by the endothelium, which culminates in transmigration of circulating monocytes, a process that may be protective in infection and some cancers, but detrimental in chronic inflammatory diseases, such as atherosclerosis. We screened a library of 642 carbo- and heterocycles of 39 distinctive scaffolds assembled through DOS based on the nucleophilic phosphine catalysis for their ability to activate human endothelial cells. Seven distinctive scaffolds of 35 compounds were identified by their capacity to bestow upon the endothelium the ability to trigger MIP1α and MIP1β production from previously quiescent monocytes. Taking advantage of the exceedingly simple assembly strategy for one specific scaffold, octahydro-1,6-naphthyridin-4-one, 96 analogs were prepared through solid-phase split-and-pool synthesis and solution phase medicinal chemistry. The diverse library revealed structural features indispensible for activation of the endothelium, simultaneously serving as tools to dissect molecular networks necessary to mediate EC-triggered activation of innate immune responses.

MIP-1 chemokines are known to play a key role in the chemotaxis of lymphocytes and monocytes, as well as protective roles in HIV pathogenesis (51) and cancer immunotherapy (52). Therefore, the identification of small molecules with potent capacity to activate the innate immune response through the endothelium raises the possibility of developing compounds for clinical scenarios in which augmented immunity may be desirable. Nevertheless, inflammation in the vessel wall can lead to endothelial dysfunction and myocardial infarction (49, 50). We demonstrate that structurally similar compounds can have disparate effects on triggering EC-mediated induction of innate immune responses. Therefore, among otherwise equal drug candidates, it may be preferable to select agents that do not have "off target" EC-activation, which may then mediate undesirable innate immune activation in the vascular wall. Indeed, the increasing number of drugs withdrawn from the market or failed in clinical trials due to cardiovascular complications (38-41) indicate the need for biological platforms that identify endothelial cell activation.

This work demonstrates that the integration of extremely efficient DOS strategy and a biological screening platform of adequate complexity can lead to deep insights into structure-function relationships during small-molecule testing and development. We identified a novel group of small molecules, octahydro-1,6-naphthyridin-4-ones, that activate the endothelium, which in turn trigger monocyte activation. Together, the work provides a novel conceptual framework for dissecting critical regulatory networks involved in EC activation by small molecules, as well as the possibility of augmenting innate immunity through endothelium-triggered immune responses.

Materials and Methods

Materials and Methods for Biology

Cells and Reagents:

Human umbilical endothelial cells (HUVEC) were purchased from (Lonza) and were used between passage 5 and 8. Peripheral blood mononuclear cells were isolated from healthy donors (UCLA Institutional Review Board #92-10-591-31) using Hypaque Ficoll (GE Healthcare). IFNγ (Peprotech) was used at 10 ng/ml in all experiments. Antibodies used: ICAM1 (Abd Serotec), E-selectin (R&D systems), CD14 (Becton Dickinson) and MIP1β (Becton Dickinson). Cytokine bead arrays for IL8, MIP1α, and MIP1β were obtained from (Becton Dickinson).

Co-Culture Assays:

HUVEC were grown to 80-90% confluency in T150 flasks (Corning). On the day of experiments, HUVEC were harvested and plated at a confluent density in 96 well plates; these were either half or full volume plates, requiring $2.5$-$5 \times 10^4$ EC per well, respectively, in complete EBM-2 media (Lonza). After adherence for 2-3 hours, IFNγ (10 ng/ml), DMSO, or compound library (final concentration, 10 mM) was added in incomplete EBM-2 media (Lonza). After 5 hours, stimuli were removed and cells were gently washed twice with RPMI (Invitrogen), followed by addition of $7.5$-$10 \times 10^4$ human PBMC in 10% FCS. For cytokine analysis, 50 ml was removed at 24 hours for CBA analysis. The biological effects observed were not attributable to either LPS contamination, nor to cellular toxicity, as determined by flow cytometric analysis and 3-(4,5-dimethylhiazol-2-yl)-2,5-diphenyl tetrazolium bromide (MTT) assay.

Cytometric Bead Arrays (CBA):

50 ml of supernatant from EC alone, PBMC alone, or co-culture conditions was collected for CBA analysis for IL8, MIP1α, and MIP1β. CBA was performed as per the manufacturer's recommendations (Becton Dickinson). Standard curves and all samples were acquired on a FacsCalibur flow cytometer and data was analyzed using FloJo software.

Flow Cytometry:

HUVEC were stimulated with IFNγ, DMSO, or compounds of interest (10 μM) for 5 hours. Stimuli were removed and cells were gently washed and media was replaced with 10% FCS for 24 hours. Cells were stained with anti-ICAM1 and anti-E-selectin, or appropriate isotype antibodies. For intracellular chemokine staining, stimulations of HUVEC were carried out as mentioned above with IFNγ, DMSO and compound of interest. After 8 hours of PBMC and HUVEC co-culture incubation, Golgi Plug (Becton Dickinson) was added to the culture and incubation carried out for an additional 16 hours. After the incubation cells were fixed, permeabilized and stained with anti-CD14 and anti-MIP1b or appropriate isotype controls. Samples were then analyzed with a FacsCalibur flow cytometer and subsequent data analysis was performed using FloJo software.

Microarrays:

HUVEC were grown as described above, and then plated at $1 \times 10^6$ in 6 well plates in complete EBM-2. Triplicate wells were treated with DMSO, active analogue (D10) and inactive analogue (E2)-all at equal volumes and concentration a final concentration of 10 μM in incomplete EBM-2. After 5 hours, media was removed and RNA was extracted using Trizol (Invitrogen), followed by RNeasy Minelut Cleanup Kit (Qiagen). RNA was taken to the UCLA Microarray Core Center where it was processed using the Human Genome Affymetrix U133 Plus 2.0 Array. Microarray data was analyzed using dChip software (version Nov. 18, 2007) from the Cheng Li Lab at http://biosun1.harvard.edu/complab/dchip. For statistical analysis using dChip software, only gene probes that were minimally present in two of the three replicates were used, and parameters for significance were set at fold change >1.25, p-value <0.05. Total number of probes present for active analogue (D10): 30,228. Total number of probes present for inactive analogue (E2): 30,000. Unsupervised dendrograms were created using dChip software. Genes with known function in immune regulation were selected based on published databases and gene functions identified by Gene Ontology or OMIM; dendrogram was created using dChip software.

Statistical Analysis:

Experimental results were compared using student t-tests; results were considered significant if p-value was <0.05. Canonical network analysis for all expressed probes in D10 and E2 datasets was performed by using Ingenuity Pathway Analysis software (version 6.0; Ingenuity Systems).

General Information for Chemical Synthesis and Compound Characterization

All reactions were performed under Ar atmospheres in oven-dried glassware with dry solvents and anhydrous conditions. Unless otherwise stated, all reagents were purchased from commercial suppliers and used without further purification. Toluene, dichloromethane (DCM), and methanol were freshly distilled from $CaH_2$. THF was distilled from sodium benzophenone ketyl prior to use. Organic solutions were concentrated under reduced pressure on a rotary evaporator or an oil pump. Synphase lanterns (A-series lantern; capacity: 75 µmol/lantern), spindles, and cogs were purchased from Mimotopes Pty. Ltd., Clayton, Australia. Prior to their first use, the lanterns were washed (3×) with the reaction solvent. Each washing was left to settle for at least 5 min, unless otherwise stated. The solid phase washings were performed using PA-grade solvents. Tebbe reagent (ca. 1.0 M in toluene) was synthesized according to the procedure reported by Grubbs (L. F. Cannizzo, R. H. Grubbs, J. Org. Chem. 1985, 50, 2386). Reactions were monitored using thin layer chromatography (TLC) on silica gel-pre-coated glass plates (0.25 mm thickness, SiliCycle silica gel). Chromatograms were visualized through fluorescence quenching with UV light at 254 nm. Flash column chromatography was performed using SiliCycle Silica-P Flash silica gel (60 Å pore size, 40-63 µm). Infrared spectra were recorded using a Perkin-Elmer Spectrum One FT-IR spectrometer. $^1H$ and $^{13}C$ NMR spectra were recorded in $CDCl_3$ on Bruker Avance 500, ARX-500, or ARX-400 spectrometers, as indicated. Chemical shifts (δ ppm) are provided relative to tetramethylsilane (TMS), with the resonance of the undeuterated solvent or TMS as the internal standard. $^1H$ NMR spectral data are reported as follows: chemical shift, multiplicity (s=singlet; d=doublet; t=triplet; q=quartet; m=multiplet), coupling constant(s) (Hz), integration. $^{13}C$ NMR spectral data are reported in terms of chemical shift. MALDI mass spectra were obtained using an AB/PerSpective DE-STR TOF instrument, with samples dissolved in $CH_3CN$ and using 2,5-dihydroxybenzoic acid or 1,8,9-anthracenetriol as the matrix. X-ray crystallographic data were collected using a Bruker SMART CCD-based diffractometer equipped with a low-temperature apparatus operated at 100 K. LCMS data were obtained on an Agilent 1200 HPLC using a Acquity BEH C-18, Acquity BEH Phenyl, Acquity BEH Shield C-18, or Acquity BEH HILIC 2.1×50 mm column, an Agilent 6224 TOF mass spectrometer in Waters ZQ Quadrupole/ESCI mode, and water/acetonitrile, water/methanol, methanol/THF as the eluent.

Synthetic Procedures and Characterization of Compounds for Solid-Phase Chemistry Synthesis of building blocks 2-methyl-2,3-butadienoic acid (2) and N-sulfonylimines (8)

2-methyl-2,3-butadienoic acid (2) was synthesized following a literature procedure (Harvey, G. R.; Ratts, K. W. *J. Org. Chem.* 1966, 31, 3907). All N-sulfonylimines (8) were synthesized through the condensation of the corresponding aldehydes with the sulfonamides catalyzed by $BF_3/OEt_2$ with azeotropic water removal (Dean-Stark), according to the literature procedure (McKay, W. R.; Proctor, G. R. *J. Chem. Soc., Perkin Trans.* 1 1981, 2435).

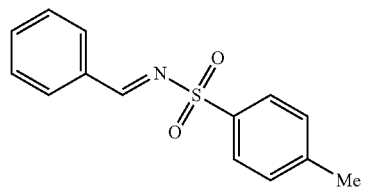

8a

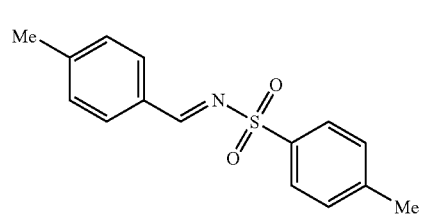

8b

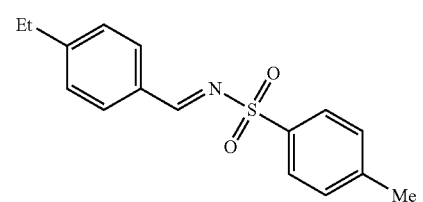

8c

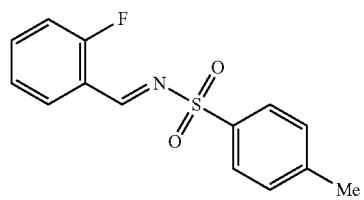

8d

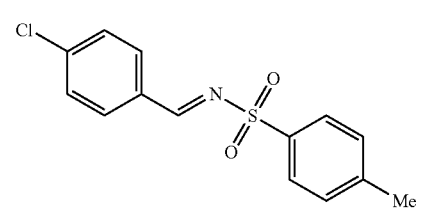

8e

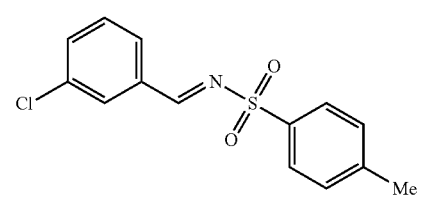

8f

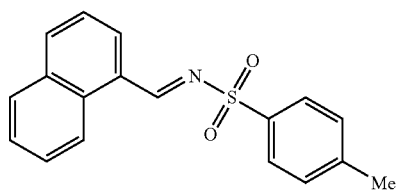

8g

-continued

8h

8i

8j

Tagging of the Building Blocks

The individual lanterns were tagged with colored spindles and cogs to encode the building blocks used for each lantern. The colors of the spindles and cogs used to encode the imine building blocks of [4+2] annulation or Tebbe reaction were summarized and showed below. Because the Diels-Alder reaction was the last step of the synthesis, tagging for the imine building blocks of Diels-Alder reaction was not necessary.

| entry | N-sulfonylimine | spindle | cog |
|-------|-----------------|---------|--------|
| 1 | 8a | none | none |
| 2 | 8b | white | none |
| 3 | 8c | yellow | none |
| 4 | 8d | red | none |
| 5 | 8e | blue | none |
| 6 | 8f | white | green |
| 7 | 8g | yellow | natural |
| 8 | 8h | yellow | black |
| 9 | 8i | red | black |
| 10 | 8j | blue | brown |

Resin Loading with 2-Methyl-2,3-butadienoic acid (2) and Solid Phase [4+2] Annulations with N-sulfonylimines (8)

The resin loading with 2-methyl-2,3-butadienoic acid (2) and solid phase [4+2] annulations with N-sulfonylimines (8) were finished following the procedures reported previously from our group (Fiji, H. D. G. et al., O. *J. Am. Chem. Soc.* 2007, 129, 5843).

Longer reaction times were needed because A-series lantern (capacity: 75 µmol/lantern) was used instead of L-series lantern (capacity: 15 µmol/lantern).

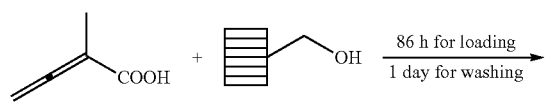

-continued

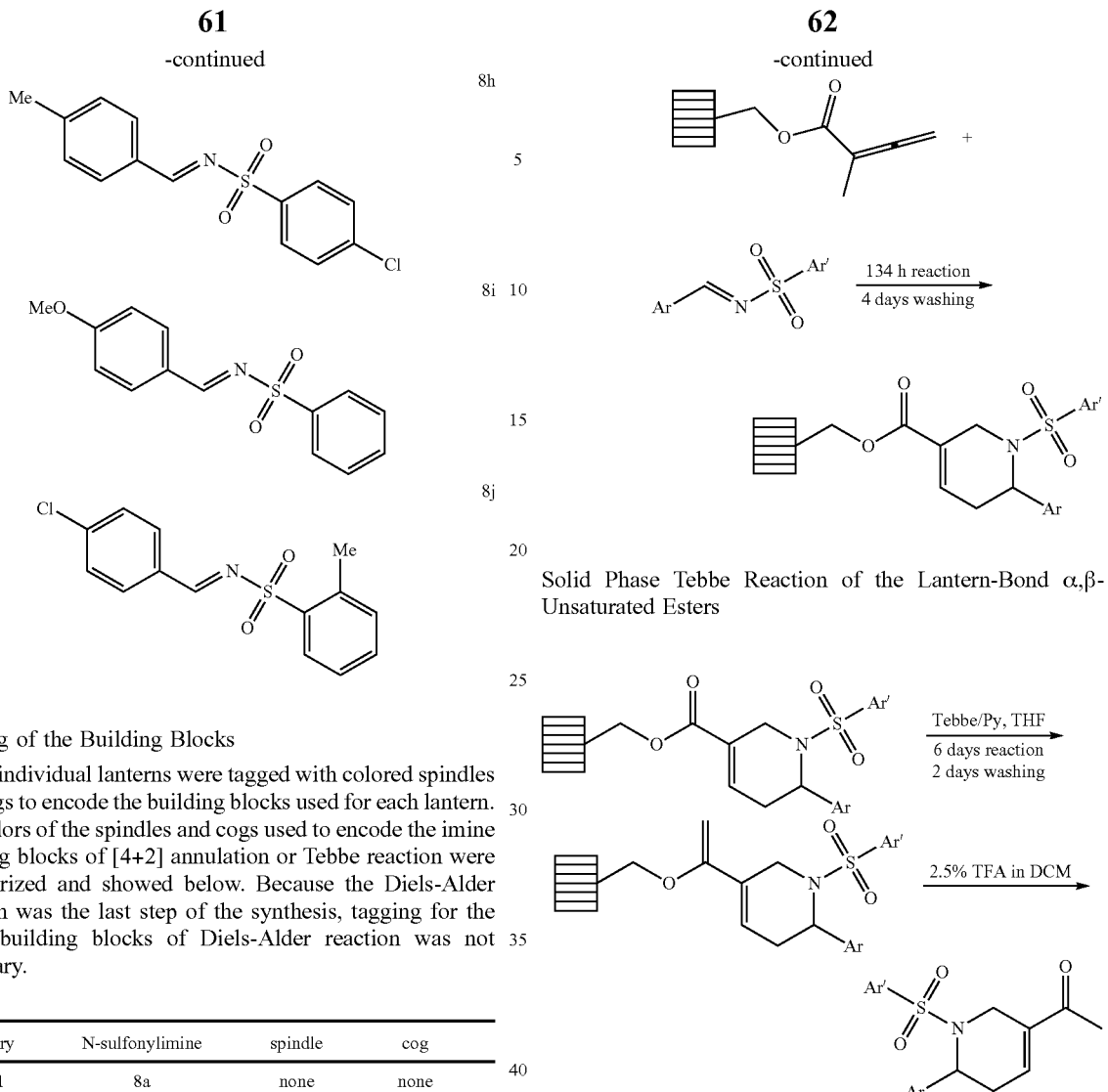

Solid Phase Tebbe Reaction of the Lantern-Bond α,β-Unsaturated Esters

The lantern-bound α,β-unsaturated esters were placed in oven-dried 250 mL flasks and charged with Ar. The lanterns were washed two times with freshly distilled DCM, five times with freshly distilled THF, and then soaked in freshly distilled THF (3 mL/lantern). The anhydrous pyridine (1.3 eq.) and 1.0 M Tebbe reagent in toluene (13.3 eq.) were added at room temperature. After 2 days, another 13.3 eq. Tebbe reagent was added. After another 4 days, the reaction was complete. The lanterns were washed as follows: THF (5×40 mL), 40 mL THF+2 mL 15% NaOH for 15 h, 50% $H_2O$ in THF (3×40 mL), THF (3×40 mL), 50 mL THF overnight, THF (2×40 mL), DCM (3×40 mL). (Note: Lanterns were soaked for at least 15 min before changing the solvents. Before the reaction setting, two times with freshly distilled DCM (at least 50 mL DCM for 22 lanterns is required) and five times with freshly distill THF (at least 50 mL DCM for 22 lanterns is required) are very important for the reaction yield. Otherwise the reaction yield will be very low.) The Tebbe products were cleaved by treatment with TFA/DCM 2.5% (7 mL/lantern) to yield the crude α,β-unsaturated ketone products.

The spectroscopic data of the representative α,β-unsaturated ketone products are listed below.

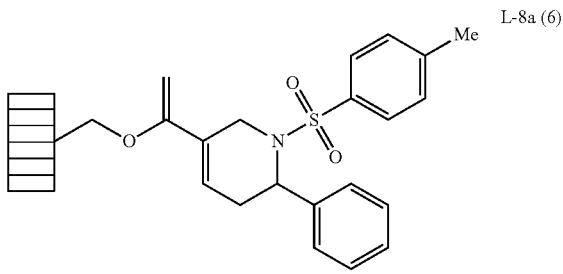

L-8a (6)

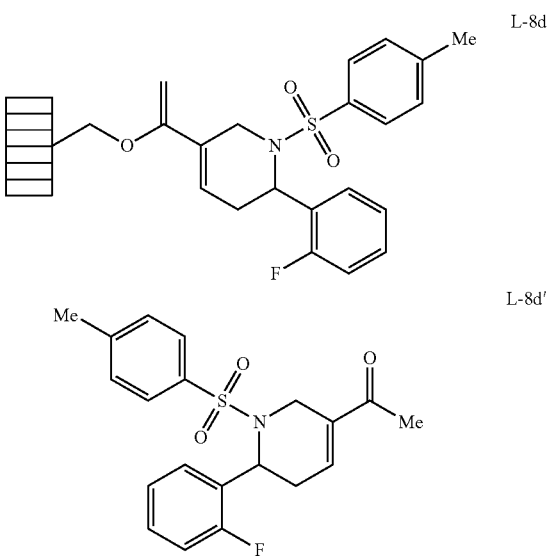

The lantern L-8a (6) was treated with 2.5% TFA in DCM (7 mL) to yield a crude product, which was purified by flash column chromatography on the silica gel using 20% ethyl acetate in hexanes to afford compound L-8a' (6') as yellow solid in 53% yield, over 4 steps; IR (film) $v_{max}$ 3062, 2920, 1666, 1160 cm$^{-1}$; $^1$H NMR (500 MHz, CDCl$_3$): δ 7.64 (d, J=8.2 Hz, 2H), 7.27-7.19 (m, 7H), 6.92 (br, 1H), 5.38 (d, J=5.4 Hz, 1H), 4.46 (d, J=18.4 Hz, 1H), 3.38 (ddd, J=18.4, 5.6, 3.3 Hz, 1H), 2.70-2.67 (m, 2H), 2.38 (s, 3H), 2.22 (s, 3H); $^{13}$C NMR (125 MHz, CDCl$_3$): δ 196.4, 143.3, 138.2, 137.1, 136.9, 136.2, 129.5, 128.5, 127.7, 127.0, 126.9, 52.1, 38.9, 27.6, 24.9, 21.4; HRMS (m/z): [M+H]$^+$ calcd. for C$_{20}$H$_{21}$NO$_3$SH, 356.1315. found, 356.1299.

The lantern L-8d was treated with 2.5% TFA in DCM (7 mL) to yield a crude product, which was purified by flash column chromatography on the silica gel using 20% ethyl acetate in hexanes to afford compound L-8d' as yellow solid in 39% yield, over 4 steps; IR (film) $v_{max}$ 3064, 2917, 1667, 1162 cm$^{-1}$; $^1$H NMR (400 MHz, CDCl$_3$): δ 7.64 (d, J=8.3 Hz, 2H), 7.24-7.17 (m, 3H), 7.02-6.92 (m, 4H), 5.72 (d, J=7.2 Hz, 1H), 4.42 (d, J=18.3 Hz, 1H), 3.59-3.52 (m, 1H), 2.93-2.84 (m, 1H), 2.64-2.57 (m, 1H), 2.37 (s, 3H), 2.26 (s, 3H); $^{13}$C NMR (100 MHz, CDCl$_3$): δ 196.5, 161.4, 158.9, 143.4, 137.2, 136.5, 136.3, 129.4, 127.8, 127.3, 126.7, 126.6, 124.0, 116.0, 115.8, 46.7, 39.4, 29.3, 25.0, 21.5; HRMS (m/z): [M+Na]$^+$ calcd. for C$_{20}$H$_{20}$FNO$_3$SNa, 396.1040. found, 396.1031.

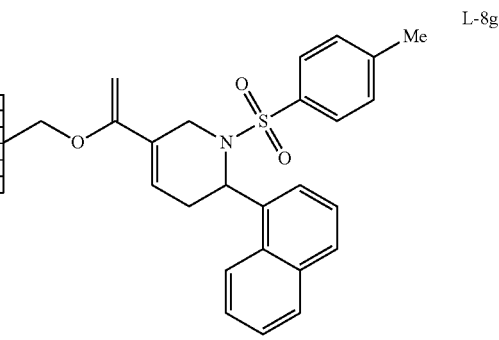

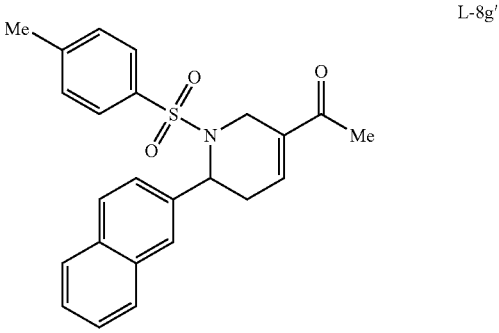

The lantern L-8g was treated with 2.5% TFA in DCM (7 mL) to yield a crude product, which was purified by flash column chromatography on the silica gel using 20% ethyl acetate in hexanes to afford compound L-8g' as yellow solid in 43% yield, over 4 steps; IR (film) $v_{max}$ 2979, 2917, 1709, 1166 cm$^{-1}$; $^1$H NMR (500 MHz, CDCl$_3$): δ 8.59 (d, J=8.5 Hz, 1H), 7.85 (d, J=8.1 Hz, 1H), 7.78 (d, J=8.1 Hz, 1H), 7.68 (d, J=8.2 Hz, 2H), 7.62 (t, J=7.3 Hz, 1H), 7.52 (t, J=7.5 Hz, 1H), 7.28 (t, J=7.7 Hz, 1H), 7.18-7.16 (m, 3H), 6.96 (t, J=2.3 Hz, 1H), 6.22 (d, J=7.2 Hz, 1H), 4.34 (d, J=18.8 Hz, 1H), 3.22 (dd, J=18.8, 2.6 Hz, 1H), 2.96 (dd, J=20.0, 3.0 Hz, 1H), 2.75 (ddd, J=20.0, 4.8, 2.3 Hz, 1H), 2.36 (s, 3H), 2.23 (s, 3H);
$^{13}$C NMR (125 MHz, CDCl$_3$): δ 196.9, 143.6, 137.8, 136.4, 136.1, 134.0, 133.4, 133.3, 129.4, 129.2, 128.7, 127.5, 126.8, 125.9, 124.5, 124.0, 123.9, 49.0, 38.8, 27.9, 24.9, 21.4; HRMS (m/z): [M+H]$^+$ calcd. for C$_{24}$H$_{23}$NO$_3$SH, 406.1471. found, 406.1458.

Solid Phase Diels-Alder Reaction of the Lantern-Bound Tebbe Dienes

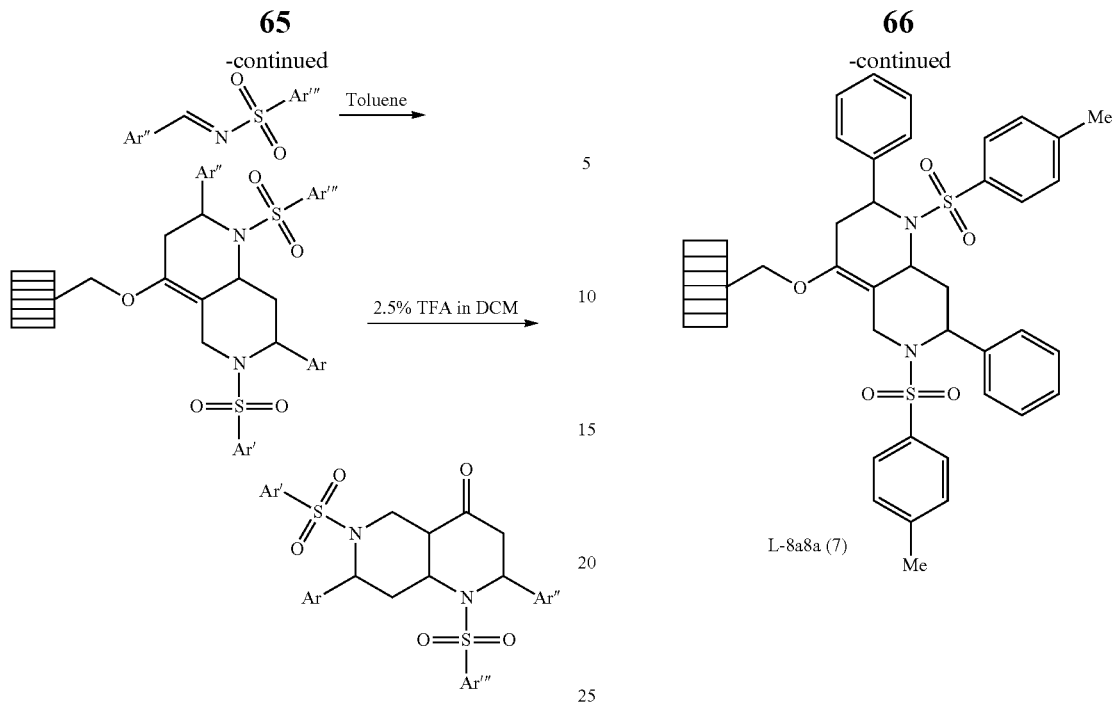

The lanterns from Tebbe reaction was place in an oven-dried 250 mL flasks and charged with Ar. The lanterns were washed three times with freshly distilled toluene (2.5 mL/lantern). The imine (26.0 eq.) was added, charged with Ar, and then the freshly distilled toluene (3 mL/lantern) was added at room temperature. The flask was removed from the Ar line, capped, and then placed aside for 6 days at 80° C. After the reaction was complete, the lanterns were washed as follows: Toluene (×5), THF (×3), DMF (×3), DMF overnight, DMF (×3), THF (×3), Toluene (×3), THF (×3), DMF overnight, DMF (×3), THF (×3), THF/2.5 M NH$_4$Cl (1:1) for 1 h, THF/H$_2$O (1:1) (×2), THF (×3), DCM (×5). After washing, the product was cleaved from the lantern by adding a solution of 2.5% TFA in DCM (7 mL). (Note: Lanterns were soaked for at least 15 min before changing the solvents.)

The spectroscopic data of the representative α,β-unsaturated ketone products are listed below.

Crystallographic data for 1a and 1a' have been deposited with the Cambridge Crystallographic Data Centre as supplementary numbers CCDC 767112 and CCDC 802608 (FIG. 13). These data can be obtained online free of charge [or from the Cambridge Crystallographic Data Center, 12, Union Road, Cambridge CB2 1EZ, UK; fax: (+44) 1223-336-033; or deposit@ccdc.cam.a

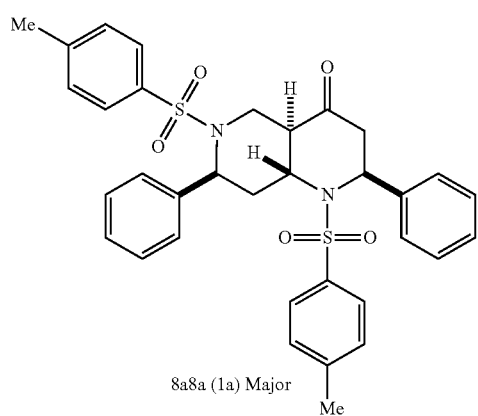

8a8a (1a) Major

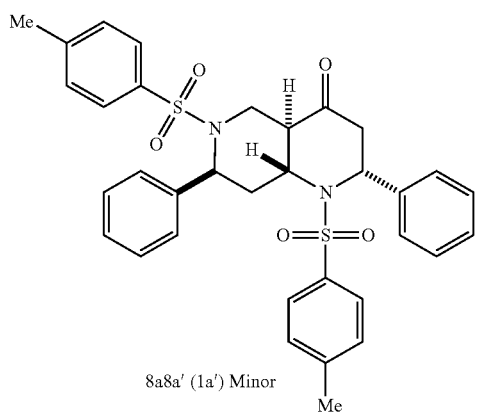

8a8a' (1a') Minor

The lantern L-8a8a (7) was treated with 2.5% TFA in DCM (7 mL) to yield a crude product, which was purified by flash column chromatography on the silica gel using 20% ethyl acetate in hexanes to afford compounds 8a8a (1a) and 8a8a' (1a') as white solid in 38% yield (dr=97:3), over 5 steps; 8a8a (1a): IR (film) ν$_{max}$ 3062, 2921, 1714, 1347, 1161, 659 cm$^{-1}$; $^1$H NMR (500 MHz, CDCl$_3$) δ 7.78 (d, J=8.3 Hz, 2H), 7.44 (d, J=8.3 Hz, 2H), 7.40-7.37 (m, 4H), 7.23 (t, J=7.5 Hz, 2H), 7.18-7.16 (m, 3H), 7.12-7.07 (m, 3H), 6.84-6.83 (m, 2H), 5.72 (d, J=6.7 Hz, 1H), 4.92 (dd, J=11.2, 7.1 Hz, 1H), 4.63-4.58 (m, 1H), 3.81 (dd, J=15.3, 8.0 Hz, 1H), 3.43 (dd, J=15.3, 9.2 Hz, 1H), 2.95 (dd, J=14.8, 2.0 Hz, 1H), 2.68 (dd, J=17.5, 8.9 Hz, 1H), 2.49 (s, 3H), 2.38 (s, 3H), 2.23 (dd, J=14.1, 7.2 Hz, 1H), 1.76 (ddd, J=13.6, 7.0, 2.0 Hz, 1H), 0.95 (td, J=13.5, 11.4 Hz, 1H); $^{13}$C NMR (125 MHz, CDCl$_3$) δ 206.6, 144.2, 143.2, 140.2, 139.4, 137.4, 137.0, 130.3, 129.4, 128.5, 128.2, 128.0, 127.3, 127.0, 126.7, 125.8, 58.5, 55.1, 53.3, 45.4, 41.4, 40.5, 36.3, 21.6, 21.4; HRMS (m/z): calculated for C$_{34}$H$_{35}$N$_2$O$_5$S$_2$N [M+H]$^+$ 615.1902. found 615.1975. 8a8a' (1a'): IR (film) $v_{max}$ cm$^{-1}$; $^1$H NMR (500 MHz, CDCl$_3$) δ 7.71 (d, J=8.5 Hz, 2H), 7.64 (d, J=8.5 Hz, 2H), 7.35-7.32 (m, 2H), 7.30-7.25 (m, 10H), 7.21 (d, J=8.0 Hz, 2H), 5.72 (dd, J=7.3, 3.4 Hz, 1H), 5.00 (s, 1H), 4.46 (d, J=14.5 Hz, 1H), 4.42-4.38 (m, 1H), 2.92 (dd, J=14.5, 4.6 Hz, 1H), 2.85 (dd, J=15.2, 3.4 Hz, 1H), 2.50-2.49 (m, 4H), 2.44 (s, 3H), 2.15 (t, J=5.4 Hz, 1H), 1.97-1.93 (m, 1H), 1.27-1.23 (m, 1H); $^{13}$C NMR (125 MHz, CDCl$_3$) δ 203.8, 144.1, 142.8, 141.1, 137.5, 136.6, 135.3, 130.1, 129.2, 128.9, 128.8, 128.5, 127.6, 127.5, 127.3, 127.0, 126.6, 55.5, 55.2, 51.5, 46.3, 42.1, 37.5, 32.9, 21.6, 21.5; MS (MALDI) calcd. for [M+Na]$^+$ 637.18. found 637.08.

1716, 1347, 1162, 660 cm$^{-1}$; $^1$H NMR (500 MHz, CDCl$_3$) δ 7.77 (d, J=8.1 Hz, 2H), 7.42-7.36 (m, 6H), 7.23 (d, J=7.5 Hz, 2H), 7.18-7.14 (m, 3H), 6.90 (d, J=8.0 Hz, 2H), 6.75 (d, J=8.0 Hz, 2H), 5.71 (d, J=6.4 Hz, 1H), 4.87 (dd, J=11.1, 7.0 Hz, 1H), 4.60 (t, J=10.5 Hz, 1H), 3.78 (dd, J=15.3, 8.0 Hz, 1H), 3.47 (dd, J=15.3, 9.1 Hz, 1H), 2.95 (dd, J=15.0, 1.5 Hz, 1H), 2.68 (dd, J=17.3, 8.7 Hz, 1H), 2.52 (q, J=7.6 Hz, 2H), 2.47 (s, 3H), 2.36 (s, 3H), 2.24 (dd, J=14.7, 7.1 Hz, 1H), 1.76-1.73 (m, 1H), 1.16 (t, J=7.6 Hz, 3H), 1.01 (td, J=12.5, 11.7 Hz, 1H); $^{13}$C NMR (125 MHz, CDCl$_3$) δ 206.6, 144.2, 143.4, 143.0, 139.5, 137.4, 137.22, 137.21, 130.3, 129.4, 128.5, 128.0, 127.6, 127.3, 127.0, 126.6, 126.0, 58.4, 55.2, 53.4, 45.6, 41.1, 40.4, 36.3, 28.3, 21.5, 21.4, 15.4; HRMS (m/z): calculated for C$_{36}$H$_{39}$N$_2$O$_5$S$_2$N [M+H]$^+$ 643.2215. found 643.2286.

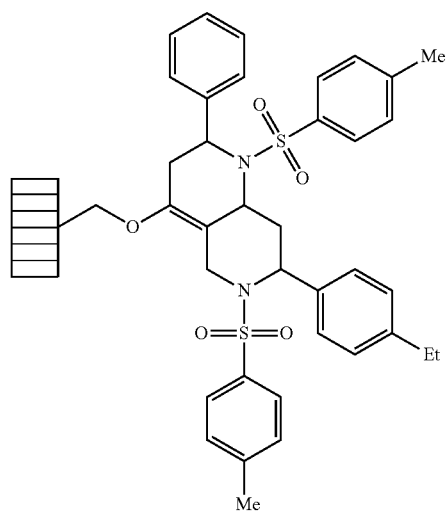

L-8c8a

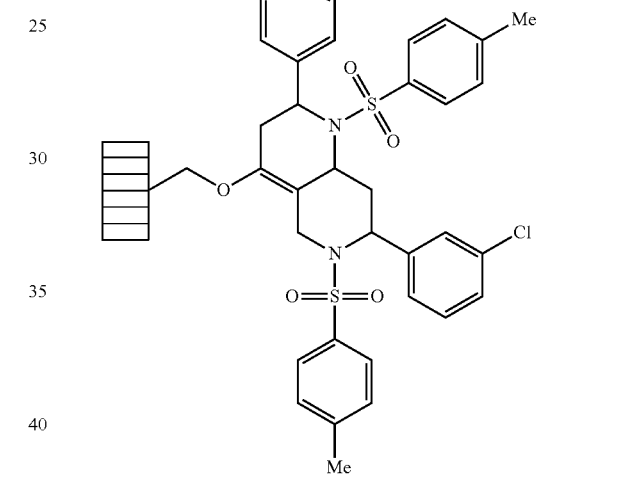

L-18f8a

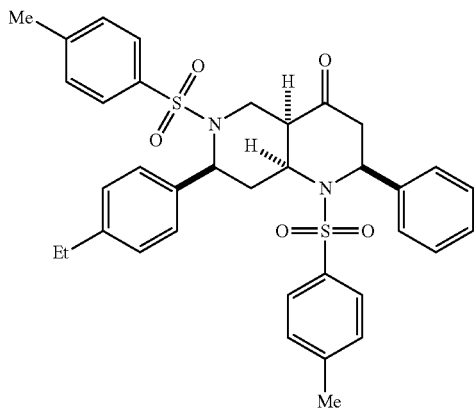

8c8a

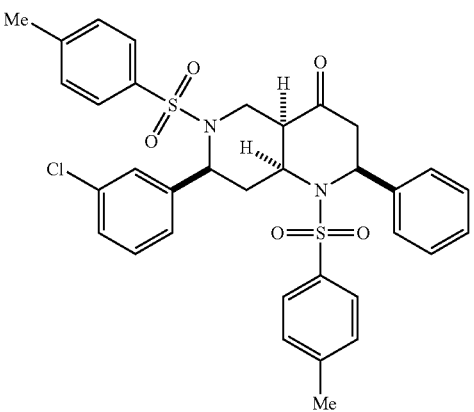

8f8a

The lantern L-8c8a was treated with 2.5% TFA in DCM (7 mL) to yield a crude product, which was purified by flash column chromatography on the silica gel using 20% ethyl acetate in hexanes to afford compound 8c8a as white solid in 38% yield, over 5 steps; IR (film) $v_{max}$ 3057, 2964, 2921, The lantern L-8f8a was treated with 2.5% TFA in DCM (7 mL) to yield a crude product, which was purified by flash column chromatography on the silica gel using 20% ethyl acetate in hexanes to afford compound 8f8a as white solid in 25% yield, over 5 steps; IR (film) $\nu_{max}$ 3063, 2920, 1714, 1348, 1162, 660 cm$^{-1}$; $^1$H NMR (500 MHz, CDCl$_3$) δ 7.76 (d, J=8.2 Hz, 2H), 7.46 (d, J=8.3 Hz, 2H), 7.39-7.37 (m, 4H), 7.25-7.16 (m, 5H), 7.07-7.01 (m, 2H), 6.75 (d, J=7.4 Hz, 1H), 6.63 (s, 1H), 5.72 (d, J=6.7 Hz, 1H), 4.80 (dd, J=11.3, 6.8 Hz, 1H), 4.59-4.54 (m, 1H), 3.79 (dd, J=15.2, 7.8 Hz, 1H), 3.46 (dd, J=15.3, 8.9 Hz, 1H), 2.96 (dd, J=14.8, 1.9 Hz, 1H), 2.66 (dd, J=17.1, 8.6 Hz, 1H), 2.47 (s, 3H), 2.38 (s, 3H), 2.24 (dd, J=14.7, 7.1 Hz, 1H), 1.71 (ddd, J=13.6, 6.8, 2.3 Hz, 1H), 0.87 (td, J=13.4, 11.5 Hz, 1H); $^{13}$C NMR (125 MHz, CDCl$_3$) δ 206.3, 144.2, 143.6, 142.0, 139.4, 137.3, 136.9, 134.0, 130.3, 129.6, 129.5, 128.6, 128.1, 127.5, 127.3, 127.0, 126.6, 126.0, 124.3, 58.0, 55.1, 53.2, 45.4, 41.4, 40.7, 36.4, 21.6, 21.4; HRMS (m/z): calculated for C$_{34}$H$_{34}$ClN$_2$O$_5$S$_2$ [M+H]$^+$ 649.1516. found 649.1590.

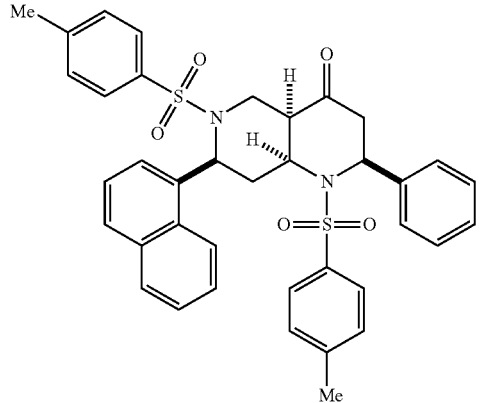

8g8a

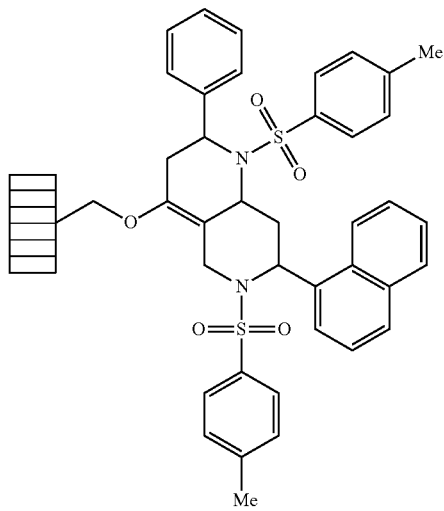

L-8g8a

The lantern L-8g8a was treated with 2.5% TFA in DCM (7 mL) to yield a crude product, which was purified by flash column chromatography on the silica gel using 20% ethyl acetate in hexanes to afford compound 8g8a as white solid in 25% yield, over 5 steps; IR (film) $\nu_{max}$ 3062, 2914, 1715, 1348, 1162, 660 cm$^{-1}$; $^1$H NMR (400 MHz, CDCl$_3$) δ 7.83 (d, J=8.2 Hz, 3H), 7.75 (d, J=7.5 Hz, 1H), 7.61 (d, J=8.1 Hz, 1H), 7.52-7.37 (m, 6H), 7.32 (d, J=7.8 Hz, 2H), 7.16-7.06 (m, 5H), 7.00 (t, J=7.8 Hz, 2H), 5.71 (d, J=5.9 Hz, 1H), 5.63 (dd, J=11.6, 6.3 Hz, 1H), 4.77-4.71 (m, 1H), 4.02 (dd, J=15.4, 7.8 Hz, 1H), 3.67 (dd, J=15.4, 9.2 Hz, 1H), 2.97 (dd, J=14.8, 2.3 Hz, 1H), 2.81 (dd, J=17.3, 8.8 Hz, 1H), 2.51 (s, 3H), 2.32 (s, 3H), 2.32-2.27 (m, 1H), 1.98 (ddd, J=13.8, 6.2, 2.3 Hz, 1H), 1.03 (td, J=13.5, 11.9 Hz, 1H); $^{13}$C NMR (100 MHz, CDCl$_3$) δ 206.7, 144.3, 143.3, 139.2, 137.5, 136.8, 136.3, 133.6, 130.4, 129.8, 129.3, 128.7, 128.6, 128.1, 128.0, 127.3, 127.2, 126.8, 126.4, 125.6, 125.1, 122.8, 122.5, 56.0, 55.3, 53.9, 46.0, 41.7, 41.6, 37.1, 21.7, 21.5; HRMS (m/z): calculated for C$_{38}$H$_{36}$N$_2$O$_5$S$_2$Na [M+Na]$^+$ 687.1959. found 687.1953.

LCMS Data of the Solid Phase Naphthyridinone Library

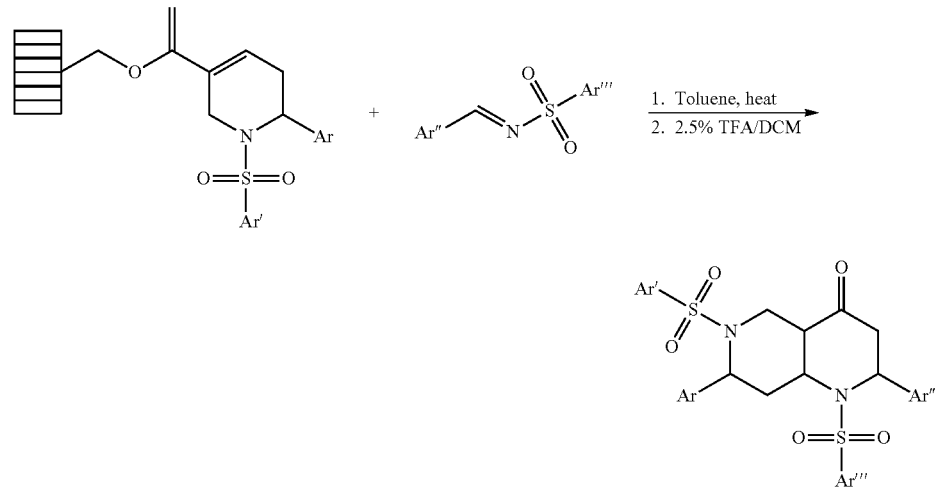

| | product | | | | | LCMS | RT$^b$ | | Purity$^d$ | | Yield$^g$ |
|---|---|---|---|---|---|---|---|---|---|---|---|
| | Ar | Ar' | Ar" | Ar''' | No. | [M]$^a$ | (min) | [M + H]$^c$ | %$^e$ | %$^f$ | (%) |
| 1 | Ph | 4-MeC$_6$H$_4$ | Ph | 4-MeC$_6$H$_4$ | 8a8a | 614.1909 | 3.70 | 615.1975 | 97 | 78 | 20 |
| 2 | Ph | 4-MeC$_6$H$_4$ | 4-MeC$_6$H$_4$ | 4-MeC$_6$H$_4$ | 8a8b | 628.2066 | 3.79 | 629.2133 | 91 | 65 | 4 |

-continued

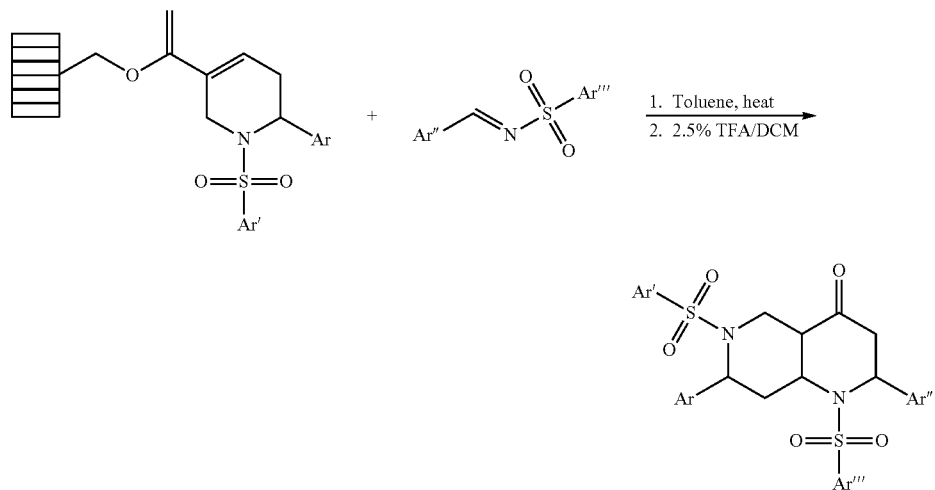

| | product | | | | LCMS | RT[b] | | Purity[d] | | Yield[g] |
|---|---|---|---|---|---|---|---|---|---|---|
| | Ar | Ar' | Ar'' | Ar''' | No. | [M][a] | (min) | [M + H][c] | %[e] | %[f] | (%) |
| 3 | Ph | 4-MeC$_6$H$_4$ | 4-EtC$_6$H$_4$ | 4-MeC$_6$H$_4$ | 8a8c | 642.2222 | 3.89 | 643.2287 | 93 | 54 | 14 |
| 4 | Ph | 4-MeC$_6$H$_4$ | 2-FC$_6$H$_4$ | 4-MeC$_6$H$_4$ | 8a8d | 632.1815 | 3.62 | 633.1880 | 96 | 69 | 18 |
| 5 | Ph | 4-MeC$_6$H$_4$ | 4-ClC$_6$H$_4$ | 4-MeC$_6$H$_4$ | 8a8e | 648.1519 | 3.81 | 649.1586 | 95 | 66 | 16 |
| 6 | Ph | 4-MeC$_6$H$_4$ | 3-ClC$_6$H$_4$ | 4-MeC$_6$H$_4$ | 8a8f | 648.1519 | 3.77 | 649.1589 | 93 | 72 | 29 |
| 7 | Ph | 4-MeC$_6$H$_5$ | 1-Naphthyl | 4-MeC$_6$H$_4$ | 8a8g | 664.2066 | 3.81 | 665.2132 | 84 | 60 | 21 |
| 8 | Ph | 4-MeC$_6$H$_4$ | 4-MeC$_6$H$_4$ | 4-ClC$_6$H$_4$ | 8a8h | 648.1519 | 3.83 | 649.1586 | 96 | 72 | 28 |
| 9 | Ph | 4-MeC$_6$H$_4$ | 4-MeOC$_6$H$_4$ | Ph | 8a8i | 630.1858 | 3.59 | 631.1926 | 91 | 45 | 11 |
| 10 | Ph | 4-MeC$_6$H$_4$ | 4-ClC$_6$H$_4$ | 2-MeC$_6$H$_4$ | 8a8j | 648.1519 | 3.82 | 649.1584 | 92 | 69 | 29 |
| 11 | 4-MeC$_6$H$_4$ | 4-MeC$_6$H$_4$ | Ph | 4-MeC$_6$H$_4$ | 8b8a | 628.2066 | 3.78 | 629.2127 | 97 | 82 | 21 |
| 12 | 4-MeC$_6$H$_4$ | 4-MeC$_6$H$_4$ | 4-MeC$_6$H$_4$ | 4-MeC$_6$H$_4$ | 8b8b | 642.2222 | 3.87 | 643.2290 | 98 | 72 | 16 |
| 13 | 4-MeC$_6$H$_4$ | 4-MeC$_6$H$_4$ | 4-EtC$_6$H$_4$ | 4-MeC$_6$H$_4$ | 8b8c | 656.2379 | 3.97 | 657.2450 | 91 | 63 | 12 |
| 14 | 4-MeC$_6$H$_4$ | 4-MeC$_6$H$_4$ | 2-FC$_6$H$_4$ | 4-MeC$_6$H$_4$ | 8b8d | 646.1971 | 3.73 | 647.2037 | 91 | 70 | 20 |
| 15 | 4-MeC$_6$H$_4$ | 4-MeC$_6$H$_4$ | 4-ClC$_6$H$_4$ | 4-MeC$_6$H$_4$ | 8b8e | 662.1676 | 3.89 | 663.1744 | 95 | 65 | 20 |
| 16 | 4-MeC$_6$H$_4$ | 4-MeC$_6$H$_4$ | 3-ClC$_6$H$_4$ | 4-MeC$_6$H$_4$ | 8b8f | 662.1676 | 3.86 | 663.1741 | 96 | 77 | 37 |
| 17 | 4-MeC$_6$H$_4$ | 4-MeC$_6$H$_4$ | 1-Naphthyl | 4-MeC$_6$H$_4$ | 8b8g | 678.2222 | 3.88 | 679.2292 | 83 | 64 | 27 |
| 18 | 4-MeC$_6$H$_4$ | 4-MeC$_6$H$_4$ | 4-MeC$_6$H$_4$ | 4-ClC$_6$H$_4$ | 8b8h | 662.1676 | 3.91 | 663.1737 | 96 | 79 | 36 |
| 19 | 4-MeC$_6$H$_4$ | 4-MeC$_6$H$_4$ | 4-MeOC$_6$H$_4$ | Ph | 8b8i | 644.2015 | 3.64 | 645.2083 | 92 | 51 | 13 |
| 20 | 4-MeC$_6$H$_4$ | 4-MeC$_6$H$_4$ | 4-ClC$_6$H$_4$ | 2-MeC$_6$H$_4$ | 8b8j | 662.1676 | 3.92 | 663.1746 | 93 | 72 | 28 |
| 21 | 4-EtC$_6$H$_4$ | 4-MeC$_6$H$_4$ | Ph | 4-MeC$_6$H$_4$ | 8c8a | 642.2222 | 3.88 | 643.2286 | 97 | 84 | 30 |
| 22 | 4-EtC$_6$H$_4$ | 4-MeC$_6$H$_4$ | 4-MeC$_6$H$_4$ | 4-MeC$_6$H$_4$ | 8c8b | 656.2379 | 3.96 | 657.2445 | 98 | 75 | 30 |
| 23 | 4-EtC$_6$H$_4$ | 4-MeC$_6$H$_4$ | 4-EtC$_6$H$_4$ | 4-MeC$_6$H$_4$ | 8c8c | 670.2535 | 4.07 | 671.2604 | 92 | 62 | 15 |
| 24 | 4-EtC$_6$H$_4$ | 4-MeC$_6$H$_4$ | 2-FC$_6$H$_4$ | 4-MeC$_6$H$_4$ | 8c8d | 660.2128 | 3.81 | 661.2195 | 91 | 68 | 21 |
| 25 | 4-EtC$_6$H$_4$ | 4-MeC$_6$H$_4$ | 4-ClC$_6$H$_4$ | 4-MeC$_6$H$_4$ | 8c8e | 676.1832 | 3.97 | 677.1900 | 94 | 69 | 17 |
| 26 | 4-EtC$_6$H$_4$ | 4-MeC$_6$H$_4$ | 3-ClC$_6$H$_4$ | 4-MeC$_6$H$_4$ | 8c8f | 676.1832 | 3.97 | 677.1896 | 96 | 81 | 35 |
| 27 | 4-EtC$_6$H$_4$ | 4-MeC$_6$H$_4$ | 1-Naphthyl | 4-MeC$_6$H$_4$ | 8c8g | 692.2379 | 3.98 | 693.2445 | 75 | 66 | 30 |
| 28 | 4-EtC$_6$H$_4$ | 4-MeC$_6$H$_4$ | 4-MeC$_6$H$_4$ | 4-ClC$_6$H$_4$ | 8c8h | 676.1832 | 4.00 | 677.1900 | 85 | 87 | 36 |
| 29 | 4-EtC$_6$H$_4$ | 4-MeC$_6$H$_4$ | 4-MeOC$_6$H$_4$ | Ph | 8c8i | 658.2171 | 3.73 | 659.2241 | 91 | 56 | 13 |
| 30 | 4-EtC$_6$H$_4$ | 4-MeC$_6$H$_4$ | 4-ClC$_6$H$_4$ | 2-MeC$_6$H$_4$ | 8c8j | 676.1832 | 4.00 | 677.1900 | 90 | 78 | 28 |
| 31 | 2-FC$_6$H$_4$ | 4-MeC$_6$H$_4$ | Ph | 4-MeC$_6$H$_4$ | 8d8a | 632.1815 | 3.71 | 633.1880 | 92 | 85 | 14 |
| 32 | 2-FC$_6$H$_4$ | 4-MeC$_6$H$_4$ | 4-MeC$_6$H$_4$ | 4-MeC$_6$H$_4$ | 8d8b | 646.1971 | 3.78 | 647.2042 | 95 | 56 | 10 |
| 33 | 2-FC$_6$H$_4$ | 4-MeC$_6$H$_4$ | 4-EtC$_6$H$_4$ | 4-MeC$_6$H$_4$ | 8d8c | 660.2128 | 3.88 | 661.2193 | 96 | 51 | 10 |
| 34 | 2-FC$_6$H$_4$ | 4-MeC$_6$H$_4$ | 2-FC$_6$H$_4$ | 4-MeC$_6$H$_4$ | 8d8d | 650.1721 | 3.61 | 651.1786 | 91 | 57 | 14 |
| 35 | 2-FC$_6$H$_4$ | 4-MeC$_6$H$_4$ | 4-ClC$_6$H$_4$ | 4-MeC$_6$H$_4$ | 8d8e | 666.1425 | 3.76 | 667.1491 | 84 | 58 | 7 |
| 36 | 2-FC$_6$H$_4$ | 4-MeC$_6$H$_4$ | 3-ClC$_6$H$_4$ | 4-MeC$_6$H$_4$ | 8d8f | 666.1425 | 3.77 | 667.1489 | 84 | 56 | 10 |
| 37 | 2-FC$_6$H$_4$ | 4-MeC$_6$H$_4$ | 1-Naphthyl | 4-MeC$_6$H$_4$ | 8d8g | 682.1971 | 3.80 | 683.2039 | 81 | 68 | 17 |
| 38 | 2-FC$_6$H$_4$ | 4-MeC$_6$H$_4$ | 4-MeC$_6$H$_4$ | 4-ClC$_6$H$_4$ | 8d8h | 666.1425 | 3.82 | 667.1490 | 92 | 71 | 17 |
| 39 | 2-FC$_6$H$_4$ | 4-MeC$_6$H$_4$ | 4-MeOC$_6$H$_4$ | Ph | 8d8i | 648.1764 | 3.59 | 649.1829 | 94 | 49 | 6 |
| 40 | 2-FC$_6$H$_4$ | 4-MeC$_6$H$_4$ | 4-ClC$_6$H$_4$ | 2-MeC$_6$H$_4$ | 8d8j | 666.1425 | 3.81 | 667.1497 | 84 | 67 | 12 |
| 41 | 4-ClC$_6$H$_4$ | 4-MeC$_6$H$_4$ | Ph | 4-MeC$_6$H$_4$ | 8e8a | 648.1519 | 3.82 | 649.1586 | 92 | 80 | 24 |
| 42 | 4-ClC$_6$H$_4$ | 4-MeC$_6$H$_4$ | 4-MeC$_6$H$_4$ | 4-MeC$_6$H$_4$ | 8e8b | 662.1676 | 3.92 | 663.1739 | 96 | 63 | 24 |
| 43 | 4-ClC$_6$H$_4$ | 4-MeC$_6$H$_4$ | 4-EtC$_6$H$_4$ | 4-MeC$_6$H$_4$ | 8e8c | 676.1832 | 4.01 | 677.1902 | 96 | 56 | 14 |
| 44 | 4-ClC$_6$H$_4$ | 4-MeC$_6$H$_4$ | 2-FC$_6$H$_4$ | 4-MeC$_6$H$_4$ | 8e8d | 666.1425 | 3.75 | 667.1494 | 85 | 64 | 17 |
| 45 | 4-ClC$_6$H$_4$ | 4-MeC$_6$H$_4$ | 4-ClC$_6$H$_4$ | 4-MeC$_6$H$_4$ | 8e8e | 682.1130 | 3.92 | 683.1199 | 94 | 57 | 16 |
| 46 | 4-ClC$_6$H$_4$ | 4-MeC$_6$H$_4$ | 3-ClC$_6$H$_4$ | 4-MeC$_6$H$_4$ | 8e8f | 682.1130 | 3.90 | 683.1194 | 96 | 68 | 30 |
| 47 | 4-ClC$_6$H$_4$ | 4-MeC$_6$H$_4$ | 1-Naphthyl | 4-MeC$_6$H$_4$ | 8e8g | 698.1676 | 3.93 | 699.1739 | 94 | 76 | 23 |
| 48 | 4-ClC$_6$H$_4$ | 4-MeC$_6$H$_4$ | 4-MeC$_6$H$_4$ | 4-ClC$_6$H$_4$ | 8e8h | 682.1130 | 3.95 | 683.1190 | 94 | 73 | 30 |
| 49 | 4-ClC$_6$H$_4$ | 4-MeC$_6$H$_4$ | 4-MeOC$_6$H$_4$ | Ph | 8e8i | 664.1469 | 3.67 | 665.1533 | 80 | 45 | 18 |
| 50 | 4-ClC$_6$H$_4$ | 4-MeC$_6$H$_4$ | 4-ClC$_6$H$_4$ | 2-MeC$_6$H$_4$ | 8e8j | 682.1130 | 3.90 | 683.1191 | 95 | 67 | 25 |
| 51 | 3-ClC$_6$H$_4$ | 4-MeC$_6$H$_4$ | Ph | 4-MeC$_6$H$_4$ | 8f8a | 648.1519 | 3.76 | 649.1590 | 95 | 78 | 24 |
| 52 | 3-ClC$_6$H$_4$ | 4-MeC$_6$H$_4$ | 4-MeC$_6$H$_4$ | 4-MeC$_6$H$_4$ | 8f8b | 662.1676 | 3.86 | 663.1737 | 83 | 52 | 6 |
| 53 | 3-ClC$_6$H$_4$ | 4-MeC$_6$H$_4$ | 4-EtC$_6$H$_4$ | 4-MeC$_6$H$_4$ | 8f8c | 676.1832 | 3.96 | 677.1891 | 84 | 44 | 2 |

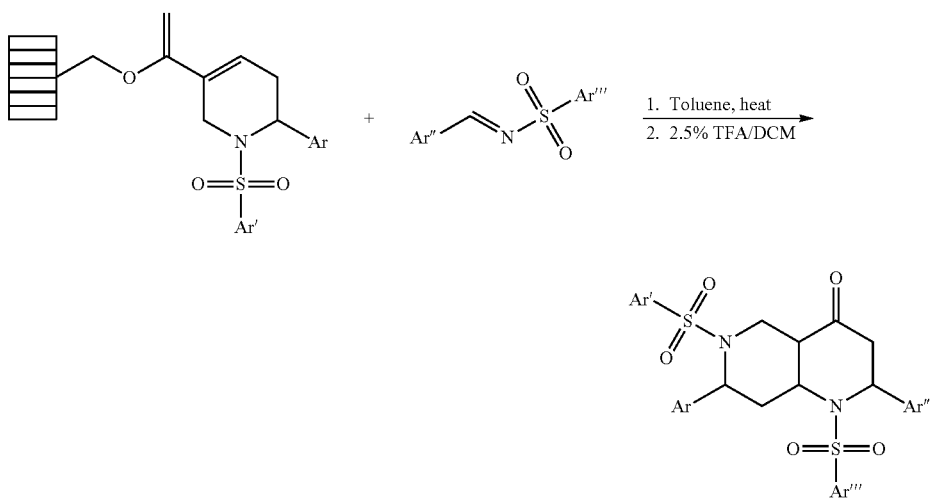

|    | product |    |    |    |    | LCMS | RT[b] |    | Purity[d] |    | Yield[g] |
|----|---------|-----|------|------|------|--------|-------|-----------|------|------|------|
|    | Ar | Ar' | Ar'' | Ar''' | No. | [M][a] | (min) | [M + H][c] | %[e] | %[f] | (%) |
| 54 | 3-ClC$_6$H$_4$ | 4-MeC$_6$H$_4$ | 2-FC$_6$H$_4$ | 4-MeC$_6$H$_4$ | 8f8d | 666.1425 | 3.70 | 667.1492 | 98 | 59 | 14 |
| 55 | 3-ClC$_6$H$_4$ | 4-MeC$_6$H$_4$ | 4-ClC$_6$H$_4$ | 4-MeC$_6$H$_4$ | 8f8e | 682.1130 | 3.86 | 683.1193 | 97 | 53 | 16 |
| 56 | 3-ClC$_6$H$_4$ | 4-MeC$_6$H$_4$ | 3-ClC$_6$H$_4$ | 4-MeC$_6$H$_4$ | 8f8f | 682.1130 | 3.83 | 683.1195 | 99 | 63 | 26 |
| 57 | 3-ClC$_6$H$_4$ | 4-MeC$_6$H$_4$ | 1-Naphthyl | 4-MeC$_6$H$_4$ | 8f8g | 698.1676 | 3.86 | 699.1736 | 81 | 60 | 23 |
| 58 | 3-ClC$_6$H$_4$ | 4-MeC$_6$H$_4$ | 4-MeC$_6$H$_4$ | 4-ClC$_6$H$_4$ | 8f8h | 682.1130 | 3.90 | 683.1191 | 93 | 70 | 29 |
| 59 | 3-ClC$_6$H$_4$ | 4-MeC$_6$H$_4$ | 4-MeOC$_6$H$_4$ | Ph | 8f8i | 664.1469 | 3.64 | 665.1538 | 99 | 46 | 18 |
| 60 | 3-ClC$_6$H$_4$ | 4-MeC$_6$H$_4$ | 4-ClC$_6$H$_4$ | 2-MeC$_6$H$_4$ | 8f8j | 682.1130 | 3.90 | 683.1195 | 94 | 65 | 25 |
| 61 | 1-Naphthyl | 4-MeC$_6$H$_4$ | Ph | 4-MeC$_6$H$_4$ | 8g8a | 664.2066 | 3.75 | 665.2134 | 93 | 81 | 19 |
| 62 | 1-Naphthyl | 4-MeC$_6$H$_4$ | 4-MeC$_6$H$_4$ | 4-MeC$_6$H$_4$ | 8g8b | 678.2222 | 3.85 | 679.2283 | 93 | 53 | 17 |
| 63 | 1-Naphthyl | 4-MeC$_6$H$_4$ | 4-EtC$_6$H$_4$ | 4-MeC$_6$H$_4$ | 8g8c | 692.2379 | 3.94 | 693.2439 | 88 | 32 | 3 |
| 64 | 1-Naphthyl | 4-MeC$_6$H$_4$ | 2-FC$_6$H$_4$ | 4-MeC$_6$H$_4$ | 8g8d | 682.1971 | 3.72 | 683.2041 | 100 | 69 | 22 |
| 65 | 1-Naphthyl | 4-MeC$_6$H$_4$ | 4-ClC$_6$H$_4$ | 4-MeC$_6$H$_4$ | 8g8e | 698.1676 | 3.87 | 699.1736 | 92 | 55 | 14 |
| 66 | 1-Naphthyl | 4-MeC$_6$H$_4$ | 3-ClC$_6$H$_4$ | 4-MeC$_6$H$_4$ | 8g8f | 698.1676 | 3.83 | 699.1742 | 72 | 58 | 39 |
| 67 | 1-Naphthyl | 4-MeC$_6$H$_4$ | 1-Naphthyl | 4-MeC$_6$H$_4$ | 8g8g | 714.2222 | 3.86 | 715.2278 | 87 | 64 | 7 |
| 68 | 1-Naphthyl | 4-MeC$_6$H$_4$ | 4-MeC$_6$H$_4$ | 4-ClC$_6$H$_4$ | 8g8h | 698.1676 | 3.88 | 699.1742 | 90 | 64 | 24 |
| 69 | 1-Naphthyl | 4-MeC$_6$H$_4$ | 4-MeOC$_6$H$_4$ | Ph | 8g8i | 680.2015 | 3.63 | 681.2081 | 89 | 41 | 8 |
| 70 | 1-Naphthyl | 4-MeC$_6$H$_4$ | 4-ClC$_6$H$_4$ | 2-MeC$_6$H$_4$ | 8g8j | 698.1676 | 3.87 | 699.1739 | 88 | 62 | 24 |
| 71 | 4-MeC$_6$H$_4$ | 4-ClC$_6$H$_4$ | Ph | 4-MeC$_6$H$_4$ | 8h8a | 648.1519 | 3.82 | 649.1585 | 94 | 81 | 21 |
| 72 | 4-MeC$_6$H$_4$ | 4-ClC$_6$H$_4$ | 4-MeC$_6$H$_4$ | 4-MeC$_6$H$_4$ | 8h8b | 662.1676 | 3.90 | 663.1742 | 90 | 48 | 19 |
| 73 | 4-MeC$_6$H$_4$ | 4-ClC$_6$H$_4$ | 4-EtC$_6$H$_4$ | 4-MeC$_6$H$_4$ | 8h8c | 676.1832 | 4.02 | 677.1891 | 100 | 62 | 16 |
| 74 | 4-MeC$_6$H$_4$ | 4-ClC$_6$H$_4$ | 2-FC$_6$H$_4$ | 4-MeC$_6$H$_4$ | 8h8d | 666.1425 | 3.77 | 667.1485 | 95 | 62 | 20 |
| 75 | 4-MeC$_6$H$_4$ | 4-ClC$_6$H$_4$ | 4-ClC$_6$H$_4$ | 4-MeC$_6$H$_4$ | 8h8e | 682.1130 | 3.80 | 683.1196 | 76 | 43 | 11 |
| 76 | 4-MeC$_6$H$_4$ | 4-ClC$_6$H$_4$ | 3-ClC$_6$H$_4$ | 4-MeC$_6$H$_4$ | 8h8f | 682.1130 | 3.89 | 683.1190 | 99 | 71 | 29 |
| 77 | 4-MeC$_6$H$_4$ | 4-ClC$_6$H$_4$ | 1-Naphthyl | 4-MeC$_6$H$_4$ | 8h8g | 698.1676 | 3.93 | 699.1738 | 92 | 71 | 21 |
| 78 | 4-MeC$_6$H$_4$ | 4-ClC$_6$H$_4$ | 4-MeC$_6$H$_4$ | 4-ClC$_6$H$_4$ | 8h8h | 682.1130 | 3.44 | 683.1190 | 97 | 71 | 24 |
| 79 | 4-MeC$_6$H$_4$ | 4-ClC$_6$H$_4$ | 4-MeOC$_6$H$_4$ | Ph | 8h8i | 664.1469 | 3.70 | 665.1531 | 95 | 43 | 12 |
| 80 | 4-MeC$_6$H$_4$ | 4-ClC$_6$H$_4$ | 4-ClC$_6$H$_4$ | 2-MeC$_6$H$_4$ | 8h8j | 682.1130 | 3.94 | 683.1191 | 96 | 70 | 25 |
| 81 | 4-MeOC$_6$H$_4$ | Ph | Ph | 4-MeC$_6$H$_4$ | 8i8a | 630.1858 | 3.56 | 631.1912 | 95 | 85 | 26 |
| 82 | 4-MeOC$_6$H$_4$ | Ph | 4-MeC$_6$H$_4$ | 4-MeC$_6$H$_4$ | 8i8b | 644.2015 | 3.65 | 645.2066 | 93 | 58 | 22 |
| 83 | 4-MeOC$_6$H$_4$ | Ph | 4-EtC$_6$H$_4$ | 4-MeC$_6$H$_4$ | 8i8c | 658.2171 | 3.75 | 659.2224 | 98 | 56 | 13 |
| 84 | 4-MeOC$_6$H$_4$ | Ph | 2-FC$_6$H$_4$ | 4-MeC$_6$H$_4$ | 8i8d | 648.1764 | 3.53 | 649.1819 | 92 | 42 | 21 |
| 85 | 4-MeOC$_6$H$_4$ | Ph | 4-ClC$_6$H$_4$ | 4-MeC$_6$H$_4$ | 8i8e | 664.1469 | 3.68 | 665.1517 | 46 | 26 | 18 |
| 86 | 4-MeOC$_6$H$_4$ | Ph | 3-ClC$_6$H$_4$ | 4-MeC$_6$H$_4$ | 8i8f | 664.1469 | 3.64 | 665.1525 | 95 | 68 | 11 |
| 87 | 4-MeOC$_6$H$_4$ | Ph | 1-Naphthyl | 4-MeC$_6$H$_4$ | 8i8g | 680.2015 | 3.68 | 681.2071 | 98 | 80 | 23 |
| 88 | 4-MeOC$_6$H$_4$ | Ph | 4-MeC$_6$H$_4$ | 4-ClC$_6$H$_4$ | 8i8h | 664.1469 | 3.71 | 682.1800 | 89 | 65 | 26 |
| 89 | 4-MeOC$_6$H$_4$ | Ph | 4-MeOC$_6$H$_4$ | Ph | 8i8i | 646.1807 | 3.47 | 647.1871 | 96 | 48 | 12 |
| 90 | 4-MeOC$_6$H$_4$ | Ph | 4-ClC$_6$H$_4$ | 2-MeC$_6$H$_4$ | 8i8j | 664.1469 | 3.56 | 682.1789 | 88 | 37 | 8 |
| 91 | 4-ClC$_6$H$_4$ | 2-MeC$_6$H$_4$ | Ph | 4-MeC$_6$H$_4$ | 8j8a | 648.1519 | 3.84 | 649.1579 | 89 | 84 | 16 |
| 92 | 4-ClC$_6$H$_4$ | 2-MeC$_6$H$_4$ | 4-MeC$_6$H$_4$ | 4-MeC$_6$H$_4$ | 8j8b | 662.1676 | 3.94 | 663.1741 | 93 | 64 | 24 |
| 93 | 4-ClC$_6$H$_4$ | 2-MeC$_6$H$_4$ | 4-EtC$_6$H$_4$ | 4-MeC$_6$H$_4$ | 8j8c | 676.1832 | 4.04 | 677.1889 | 94 | 37 | 11 |
| 94 | 4-ClC$_6$H$_4$ | 2-MeC$_6$H$_4$ | 2-FC$_6$H$_4$ | 4-MeC$_6$H$_4$ | 8j8d | 666.1425 | 3.77 | 667.1490 | 80 | 62 | 23 |
| 95 | 4-ClC$_6$H$_4$ | 2-MeC$_6$H$_4$ | 4-ClC$_6$H$_4$ | 4-MeC$_6$H$_4$ | 8j8e | 682.1130 | 3.94 | 683.1182 | 94 | 56 | 14 |
| 96 | 4-ClC$_6$H$_4$ | 2-MeC$_6$H$_4$ | 3-ClC$_6$H$_4$ | 4-MeC$_6$H$_4$ | 8j8f | 682.1130 | 3.92 | 683.1188 | 92 | 71 | 25 |
| 97 | 4-ClC$_6$H$_4$ | 2-MeC$_6$H$_4$ | 1-Naphthyl | 4-MeC$_6$H$_4$ | 8j8g | 698.1676 | 3.97 | 699.1747 | 84 | 69 | 24 |
| 98 | 4-ClC$_6$H$_4$ | 2-MeC$_6$H$_4$ | 4-MeC$_6$H$_4$ | 4-ClC$_6$H$_4$ | 8j8h | 682.1130 | 4.00 | 683.1172 | 74 | 76 | 19 |

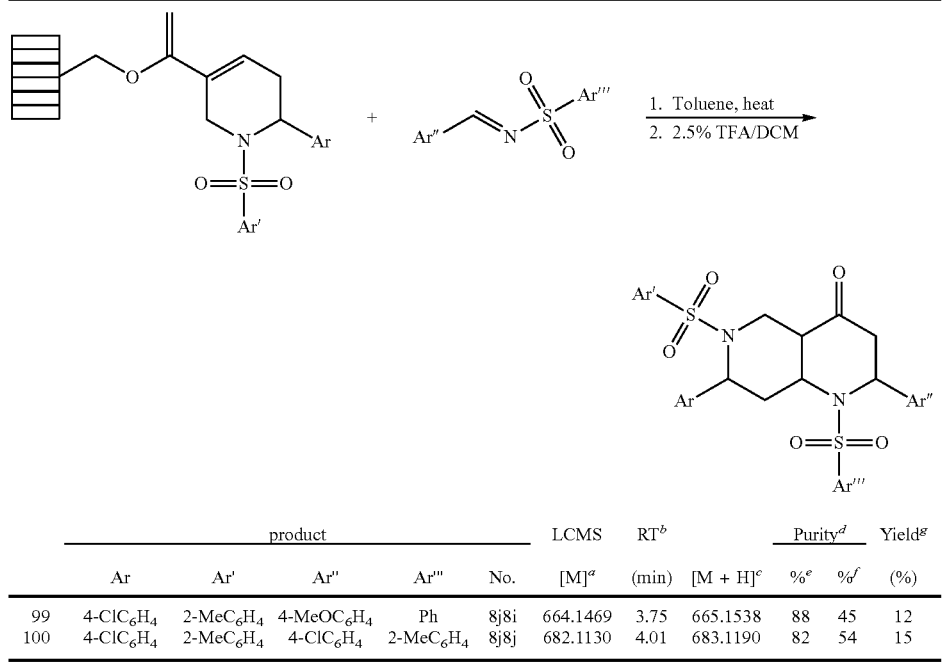

| | | product | | | LCMS [M]$^a$ | RT$^b$ (min) | [M + H]$^c$ | Purity$^d$ %$^e$ | %$^f$ | Yield$^g$ (%) |
|---|---|---|---|---|---|---|---|---|---|---|
| | Ar | Ar' | Ar'' | Ar''' | No. | | | | | |
| 99 | 4-ClC$_6$H$_4$ | 2-MeC$_6$H$_4$ | 4-MeOC$_6$H$_4$ | Ph | 8j8i | 664.1469 | 3.75 | 665.1538 | 88 | 45 | 12 |
| 100 | 4-ClC$_6$H$_4$ | 2-MeC$_6$H$_4$ | 4-ClC$_6$H$_4$ | 2-MeC$_6$H$_4$ | 8j8j | 682.1130 | 4.01 | 683.1190 | 82 | 54 | 15 |

$^a$Calculated exact mass.
$^b$Retention time.
$^c$High resolution mass found.
$^d$UV area percent.
$^e$Final purity after prep HPLC purification.
$^f$Crude purity after TFA cleaving.
$^g$Final isolated yield based on the lantern capacity after prep HPLC isolation.

Solution Phase Medicinal Chemistry and Characterization of Compounds

Synthesis of Naphthyridine Enol Ethers 11' and Naphthyridinones 11

All dienes (9), naphthyridine enol ethers (11'), and naphthyridinones (11) were synthesized according to procedures reported previously (Wang Z, et al. (2010) Diversity Through a Branched Reaction Pathway: Generation of Multicyclic Scaffolds and Identification of Antimigratory Agents. *Chem. Eur J* Published online on November 9; DOI: 10.1002/chem.201002195).

Reaction Sequence for Naphthyridinone Library Synthesis

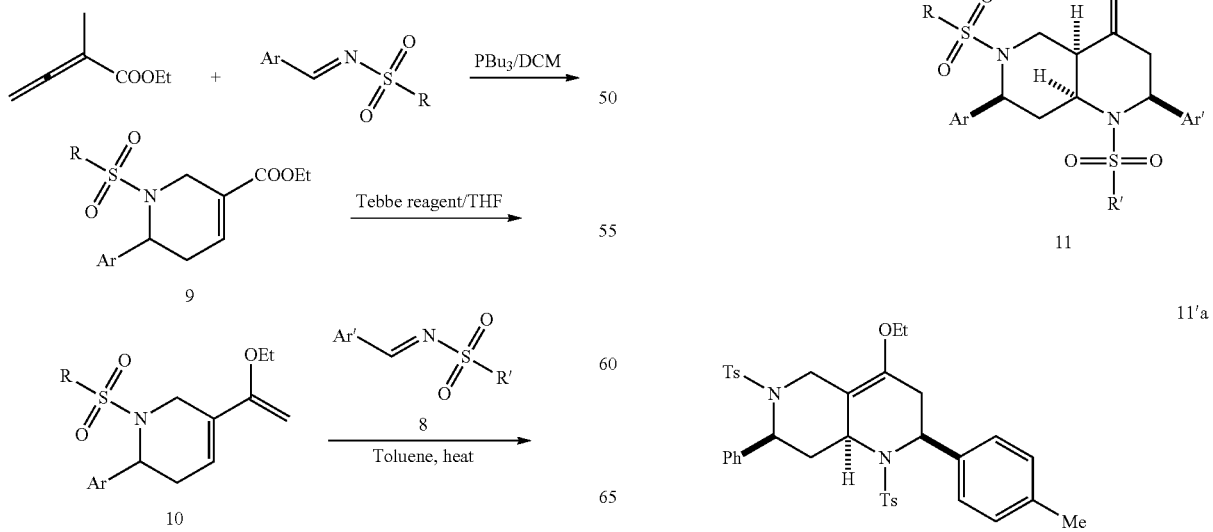

71% yield; white solid; IR (film) $v_{max}$ 3030, 2978, 2923, 1701, 1346, 1162, 668 cm$^{-1}$; $^1$H NMR (500 MHz, CDCl$_3$) δ 7.55 (d, J=8.2 Hz, 2H), 7.51 (d, J=8.2 Hz, 2H), 7.28 (d, J=8.1 Hz, 2H), 7.22 (d, J=8.0 Hz, 4H), 7.14-7.11 (m, 3H), 7.05 (d, J=8.0 Hz, 2H), 6.93-6.92 (m, 2H), 5.15 (d, J=5.8 Hz, 1H), 4.80 (t, J=8.7 Hz, 1H), 4.26 (d, J=16.4 Hz, 1H), 4.14-4.08 (m, 2H), 3.80 (dq, J=9.8, 7.1 Hz, 1H), 3.64 (dq, J=9.8, 7.1 Hz, 1H), 2.51 (d, J=16.5 Hz, 1H), 2.45 (s, 3H), 2.39 (s, 3H), 2.26-2.20 (m, 4H), 1.93-1.88 (m, 1H), 1.23-1.15 (m, 4H); $^{13}$C NMR (125 MHz, CDCl$_3$) δ 143.4, 142.9, 142.6, 140.8, 137.5, 137.1, 136.6, 136.5, 129.7, 129.3, 128.9, 127.9, 127.3, 127.2, 127.1, 126.7, 126.6, 110.6, 63.3, 58.3, 52.4, 51.7, 42.7, 38.5, 25.6, 21.5, 21.4, 20.8, 15.1; MS (MALDI) calcd. for C$_{37}$H$_{40}$N$_2$O$_5$S$_2$Na [M+Na]$^+$ 679.23. found 679.68.

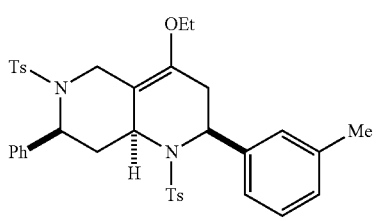
11'b

78% yield; white solid; IR (film) $v_{max}$ 3030, 2978, 2917, 1702, 1346, 1161, 656 cm$^{-1}$; $^1$H NMR (500 MHz, CDCl$_3$) δ 7.55 (d, J=8.2 Hz, 2H), 7.52 (d, J=8.2 Hz, 2H), 7.28 (d, J=8.0 Hz, 2H), 7.22 (d, J=8.1 Hz, 4H), 7.18 (s, 1H), 7.14-7.13 (m, 5H), 7.00-6.94 (m, 3H), 5.15 (d, J=6.3 Hz, 1H), 4.85 (t, J=8.7 Hz, 1H), 4.28 (d, J=16.7 Hz, 1H), 4.18-4.12 (m, 2H), 3.80 (dq, J=9.8, 7.1 Hz, 1H), 3.64 (dq, J=9.8, 7.1 Hz, 1H), 2.51 (d, J=16.5 Hz, 1H), 2.44 (s, 3H), 2.38 (s, 3H), 2.30-2.25 (m, 4H), 1.92-1.87 (m, 1H), 1.28 (td, J=12.7, 10.0 Hz, 1H), 1.15 (t, J=7.1 Hz, 3H); $^{13}$C NMR (125 MHz, CDCl$_3$) δ 143.5, 143.0, 142.7, 140.8, 139.7, 137.8, 137.4, 136.7, 129.8, 129.4, 128.4, 128.2, 128.1, 128.0, 127.1, 126.7, 126.6, 124.2, 110.5, 63.3, 58.2, 52.6, 51.7, 42.7, 38.4, 25.4, 21.5, 21.45, 21.42, 15.1; MS (MALDI) calcd. for C$_{37}$H$_{40}$N$_2$O$_5$S$_2$Na [M+Na]$^+$ 679.23. found 679.66.

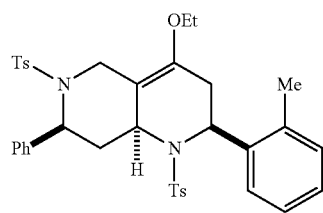
11'c

68% yield; white solid; IR (film) $v_{max}$ 3030, 2979, 2925, 1702, 1348, 1162, 654 cm$^{-1}$; $^1$H NMR (500 MHz, CDCl$_3$) δ 7.62 (d, J=8.2 Hz, 2H), 7.45 (d, J=8.2 Hz, 2H), 7.27 (d, J=8.0 Hz, 2H), 7.18 (d, J=8.1 Hz, 2H), 7.13-7.06 (m, 7H), 6.87 (dd, J=7.8, 1.1 Hz, 2H), 5.47 (d, J=6.1 Hz, 1H), 4.71 (dd, J=9.6, 7.6 Hz, 1H), 4.25-4.19 (m, 2H), 4.13 (d, J=17.1 Hz, 1H), 3.64 (dq, J=10.0, 7.1 Hz, 1H), 3.46 (dq, J=10.0, 7.1 Hz, 1H), 2.49 (s, 3H), 2.42 (s, 3H), 2.39-2.36 (m, 4H), 2.26-2.21 (m, 1H), 2.10-2.04 (m, 1H), 1.27-1.16 (m, 1H), 1.01 (t, J=7.1 Hz, 3H); $^{13}$C NMR (125 MHz, CDCl$_3$) δ 143.6, 143.2, 142.9, 140.4, 137.8, 137.4, 136.6, 136.6, 131.3, 129.6, 129.2, 127.9, 127.8, 127.4, 127.2, 127.1, 126.9, 126.8, 125.4, 110.7, 63.2, 58.6, 52.0, 51.3, 42.9, 36.6, 27.0, 21.4, 20.2, 14.9; MS (MALDI) calcd. for C$_{37}$H$_{40}$N$_2$O$_5$S$_2$Na [M+Na]$^+$ 679.23. found 679.50.

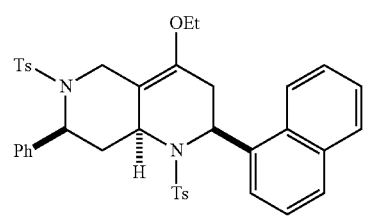
11'd

67% yield; white solid; IR (film) $v_{max}$ 3053, 2978, 2921, 1702, 1346, 1161, 658 cm$^{-1}$; $^1$H NMR (500 MHz, CDCl$_3$) δ 8.68 (d, J=8.7 Hz, 1H), 7.78 (d, J=8.2 Hz, 1H), 7.72 (d, J=7.9 Hz, 1H), 7.66 (d, J=8.1 Hz, 2H), 7.59 (t, J=7.6 Hz, 1H), 7.48-7.45 (m, 3H), 7.36-7.30 (m, 2H), 7.27-7.26 (m, 2H), 7.20 (d, J=8.0 Hz, 2H), 7.12-7.07 (m, 3H), 6.81 (d, J=6.5 Hz, 2H), 6.12 (d, J=6.2 Hz, 1H), 4.58 (t, J=8.6 Hz, 1H), 4.24 (s, 2H), 4.14 (d, J=12.0 Hz, 1H), 3.67 (dq, J=9.9, 7.1 Hz, 1H), 3.52 (dq, J=9.9, 7.1 Hz, 1H), 2.60 (d, J=16.6 Hz, 1H), 2.48-2.42 (m, 4H), 2.39 (s, 3H), 1.76-1.72 (m, 1H), 1.08-1.01 (m, 4H); $^{13}$C NMR (125 MHz, CDCl$_3$) δ 143.8, 143.5, 136.6, 135.0, 133.8, 129.6, 129.3, 128.9, 128.7, 127.9, 127.6, 127.1, 126.8, 126.4, 125.7, 125.1, 124.6, 124.4, 124.0, 110.2, 63.3, 58.5, 52.0, 50.4, 42.9, 36.3, 27.8, 21.4, 15.0; MS (MALDI) calcd. for C$_{40}$H$_{40}$N$_2$O$_5$S$_2$Na [M+Na]$^+$ 715.23. found 715.54.

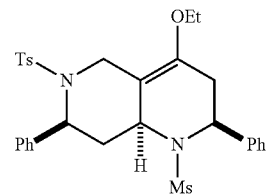
11'e

60% yield; white solid; IR (film) $v_{max}$ 3030, 2979, 2929, 1673, 1336, 1157, 664 cm$^{-1}$; $^1$H NMR (500 MHz, CDCl$_3$) δ 7.57 (d, J=8.2 Hz, 2H), 7.33 (d, J=7.7 Hz, 2H), 7.26-7.21 (m, 4H), 7.19-7.14 (m, 4H), 7.02-7.00 (m, 2H), 5.24 (d, J=5.7 Hz, 1H), 4.81 (dd, J=10.1, 7.8 Hz, 1H), 4.55 (d, J=17.4 Hz, 1H), 4.05 (d, J=17.6 Hz, 1H), 3.96 (dq, J=9.6, 7.1 Hz, 1H), 3.84 (dq, J=9.6, 7.1 Hz, 1H), 3.55 (d, J=12.4 Hz, 1H), 2.83 (d, J=16.6 Hz, 1H), 2.63 (s, 3H), 2.56-2.51 (m, 1H), 2.38 (s, 3H), 2.30-2.28 (m, 1H), 1.32 (t, J=7.1 Hz, 1H), 1.15 (td, J=12.8, 10.5 Hz, 1H); $^{13}$C NMR (125 MHz, CDCl$_3$) δ 143.0, 142.7, 140.8, 139.6, 136.7, 129.4, 128.9, 128.3, 128.1, 127.5, 127.2, 127.1, 126.2, 110.7, 63.5, 58.0, 52.6, 51.3, 42.5, 38.0, 37.9, 27.0, 21.4, 15.5; MS (MALDI) calcd. for C$_{30}$H$_{34}$N$_2$O$_5$S$_2$Na [M+Na]$^+$ 589.18. found 589.32.

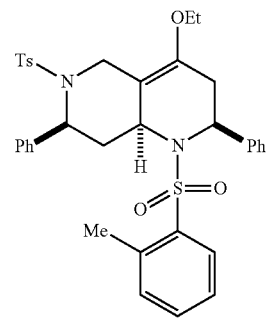
11'f

80% yield; white solid; IR (film) $v_{max}$ 3062, 2978, 2925, 1674, 1311, 1161, 664 cm$^{-1}$; $^1$H NMR (500 MHz, CDCl$_3$)

δ 7.77 (d, J=7.8 Hz, 1H), 7.49-7.46 (m, 3H), 7.37-7.30 (m, 4H), 7.24 (d, J=7.8 Hz, 2H), 7.20-7.11 (m, 6H), 6.94-6.92 (m, 2H), 5.06 (d, J=5.8 Hz, 1H), 4.68 (dd, J=9.7, 7.5 Hz, 1H), 4.29 (s, 2H), 4.18 (d, J=12.2 Hz, 1H), 3.91 (dq, J=9.7, 7.1 Hz, 1H), 3.78 (dq, J=9.7, 7.1 Hz, 1H), 2.63 (d, J=16.0 Hz, 1H), 2.56 (s, 3H), 2.33-2.29 (m, 4H), 2.17-2.12 (m, 1H), 1.28-1.19 (m, 4H); $^{13}$C NMR (125 MHz, CDCl$_3$) δ 143.1, 143.0, 140.7, 139.6, 138.0, 137.5, 136.3, 132.9, 132.8, 129.4, 129.2, 128.3, 128.0, 127.6, 127.2, 127.0, 126.7, 126.2, 110.7, 63.5, 58.6, 52.2, 51.5, 43.2, 38.1, 26.4, 21.4, 20.6, 15.3; MS (MALDI) calcd. for C$_{36}$H$_{38}$N$_2$O$_5$S$_2$Na [M+Na]$^+$ 665.21. found 665.48.

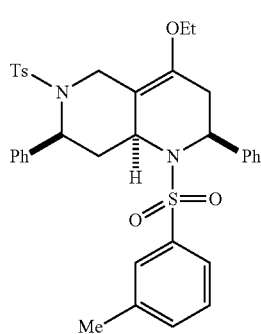

11'g

61% yield; white solid; IR (film) ν$_{max}$ 3060, 2977, 2921, 1699, 1344, 1160, 663 cm$^{-1}$; $^1$H NMR (500 MHz, CDCl$_3$) δ 7.64 (s, 1H), 7.47 (d, J=8.0 Hz, 2H), 7.42-7.35 (m, 5H), 7.25-7.23 (m, 2H), 7.19-7.16 (m, 3H), 7.11-7.09 (m, 3H), 6.89 (d, J=6.9 Hz, 2H), 4.82 (t, J=8.7 Hz, 1H), 4.28-4.22 (m, 2H), 4.11 (d, J=17.3 Hz, 1H), 3.81 (dq, J=9.9, 7.5 Hz, 1H), 3.64 (dq, J=9.9, 7.5 Hz, 1H), 2.54 (d, J=16.5 Hz, 1H), 2.44 (s, 3H), 2.36 (s, 3H), 2.27-2.22 (m, 1H), 1.96-1.92 (m, 1H), 1.88-1.14 (m, 4H); $^{13}$C NMR (125 MHz, CDCl$_3$) δ 142.9, 142.5, 140.6, 140.1, 139.6, 139.4, 136.6, 133.5, 129.3, 129.0, 128.3, 128.0, 127.4, 127.3, 127.1, 126.7, 123.6, 110.9, 63.4, 58.3, 52.6, 51.8, 42.7, 38.5, 25.5, 21.4, 21.3, 15.1; MS (MALDI) calcd. for C$_{36}$H$_{38}$N$_2$O$_5$S$_2$Na [M+Na]$^+$ 665.21. found 665.45.

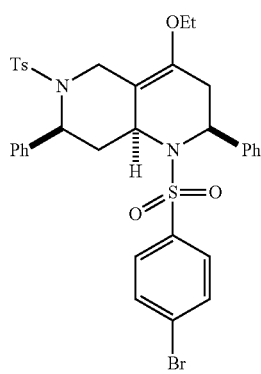

11'h

75% yield; white solid; IR (film) ν$_{max}$ 3060, 2977, 1699, 1346, 1162, 664 cm$^{-1}$; $^1$H NMR (500 MHz, CDCl$_3$) δ 7.65 (d, J=8.5 Hz, 2H), 7.56 (d, J=8.5 Hz, 2H), 7.49 (d, J=8.2 Hz, 2H), 7.35 (d, J=7.7 Hz, 2H), 7.28-7.25 (m, 2H), 7.21-7.18 (m, 3H), 7.13-7.09 (m, 3H), 6.90 (dd, J=7.5, 1.6 Hz, 2H), 5.21 (d, J=5.8 Hz, 1H), 4.84 (dd, J=9.6, 8.0 Hz, 1H), 4.28 (d, J=17.0 Hz, 1H), 4.17 (d, J=12.4 Hz, 1H), 4.08 (d, J=17.0 Hz, 1H), 3.83 (dq, J=9.8, 7.1 Hz, 1H), 3.67 (dq, J=9.8, 7.1 Hz, 1H), 2.59 (d, J=16.5 Hz, 1H), 2.38 (s, 3H), 2.28-2.23 (m, 1H), 1.98-1.93 (m, 1H), 1.23-1.14 (m, 4H); $^{13}$C NMR (125 MHz, CDCl$_3$) δ 143.0, 142.4, 140.5, 139.4, 139.3, 136.7, 132.5, 129.3, 128.4, 128.2, 128.0, 127.63, 127.62, 127.4, 127.2, 127.1, 126.6, 110.7, 63.4, 58.1, 52.7, 52.0, 42.6, 38.3, 25.6, 21.4, 15.1; MS (MALDI) calcd. for C$_{35}$H$_{35}$BrN$_2$O$_5$S$_2$Na [M+Na]$^+$ 731.10. found 731.40.

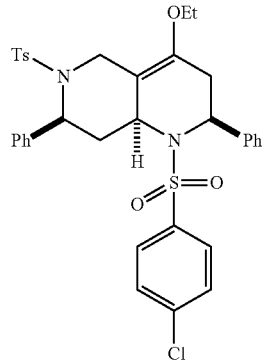

11'i

76% yield; white solid; IR (film) ν$_{max}$ 3062, 2979, 2925, 1699, 1346, 1163, 665 cm$^{-1}$; $^1$H NMR (500 MHz, CDCl$_3$) δ 7.63 (d, J=8.6 Hz, 2H), 7.49-7.47 (m, 4H), 7.35 (d, J=7.7 Hz, 2H), 7.27-7.24 (m, 2H), 7.20-7.18 (m, 3H), 7.14-7.09 (m, 3H), 6.89 (dd, J=7.6, 1.6 Hz, 2H), 5.21 (d, J=5.8 Hz, 1H), 4.84 (dd, J=9.6, 8.0 Hz, 1H), 4.28 (d, J=16.7 Hz, 1H), 4.17 (d, J=12.4 Hz, 1H), 4.08 (d, J=17.0 Hz, 1H), 3.83 (dq, J=9.8, 7.1 Hz, 1H), 3.66 (dq, J=9.8, 7.1 Hz, 1H), 2.59 (d, J=16.5 Hz, 1H), 2.38 (s, 3H), 2.28-2.23 (m, 1H), 1.98-1.92 (m, 1H), 1.21-1.13 (m, 4H); $^{13}$C NMR (125 MHz, CDCl$_3$) δ 142.9, 142.4, 140.5, 139.3, 139.2, 138.9, 136.7, 129.5, 129.3, 128.4, 128.1, 128.0, 127.6, 127.4, 127.2, 127.1, 126.6, 110.7, 63.4, 58.1, 52.7, 51.9, 42.6, 38.3, 25.6, 21.4, 15.1; MS (MALDI) calcd. for C$_{35}$H$_{35}$ClN$_2$O$_5$S$_2$Na [M+Na]$^+$ 685.16. found 685.48.

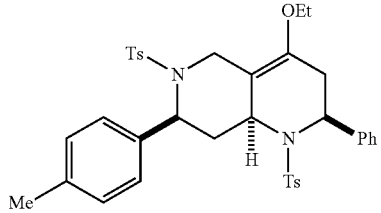

11'j

81% yield; white solid; IR (film) ν$_{max}$ 3027, 2978, 2917, 1700, 1344, 1162, 655 cm$^{-1}$; $^1$H NMR (400 MHz, CDCl$_3$) δ 7.56 (d, J=8.3 Hz, 2H), 7.50 (d, J=8.3 Hz, 2H), 7.36 (d, J=7.5 Hz, 2H), 7.30-7.18 (m, 7H), 6.92 (d, J=7.9 Hz, 2H), 6.81 (d, J=8.0 Hz, 2H), 5.19 (d, J=5.7 Hz, 1H), 4.77 (dd, J=9.7, 7.7 Hz, 1H), 4.26 (d, J=16.6 Hz, 1H), 4.17-4.09 (m, 2H), 3.81 (dq, J=9.8, 7.0 Hz, 1H), 3.65 (dq, J=9.8, 7.0 Hz, 1H), 2.53 (d, J=16.5 Hz, 1H), 2.44 (s, 3H), 2.38 (s, 3H), 2.26-2.19 (m, 4H), 1.95-1.88 (m, 1H), 1.22-1.15 (m, 4H); $^{13}$C NMR (125 MHz, CDCl$_3$) δ 143.6, 143.0, 142.6, 139.8, 137.8, 137.6, 136.9, 136.8, 129.9, 129.4, 128.9, 128.4, 127.6, 127.3, 126.9, 126.7, 111.0, 63.5, 58.4, 52.7, 52.0, 42.8, 38.7, 25.6, 21.6, 21.0, 15.2; MS (MALDI) calcd. for C$_{37}$H$_{40}$N$_2$O$_5$S$_2$Na [M+Na]$^+$ 679.23. found 679.55.

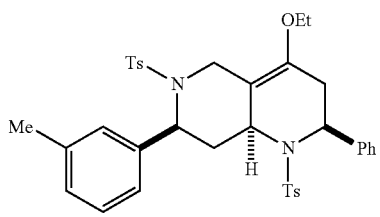
11'k

85% yield; white solid; IR (film) ν$_{max}$ 3029, 2978, 2913, 1702, 1345, 1162, 656 cm$^{-1}$; $^1$H NMR (400 MHz, CDCl$_3$) δ 7.58 (d, J=7.6 Hz, 2H), 7.47 (d, J=7.7 Hz, 2H), 7.36 (d, J=7.6 Hz, 2H), 7.29 (d, J=8.0 Hz, 2H), 7.24 (d, J=7.6 Hz, 2H), 7.19-7.16 (m, 3H), 7.01 (t, J=7.5 Hz, 1H), 6.92 (d, J=7.4 Hz, 1H), 6.74 (d, J=7.5 Hz, 1H), 6.63 (s, 1H), 5.19 (d, J=5.7 Hz, 1H), 4.76 (dd, J=9.8, 7.6 Hz, 1H), 4.29 (d, J=16.7 Hz, 1H), 4.18-4.11 (m, 2H), 3.82 (dq, J=9.5, 6.9 Hz, 1H), 3.65 (dq, J=9.5, 6.9 Hz, 1H), 2.54 (d, J=16.4 Hz, 1H), 2.45 (s, 3H), 2.37 (s, 3H), 2.24-2.19 (m, 1H), 2.16 (s, 3H), 1.95-1.91 (m, 1H), 1.20-1.16 (m, 4H); $^{13}$C NMR (125 MHz, CDCl$_3$) δ 143.5, 142.8, 142.5, 140.5, 139.7, 137.5, 137.4, 136.9, 129.8, 129.2, 128.2, 127.9, 127.8, 127.4, 127.37, 127.35, 127.1, 126.8, 123.8, 111.0, 63.4, 58.5, 52.6, 51.9, 42.8, 38.7, 25.6, 21.5, 21.4, 21.2, 15.1; MS (MALDI) calcd. for C$_{37}$H$_{40}$N$_2$O$_5$S$_2$Na [M+Na]$^+$ 679.23. found 679.73.

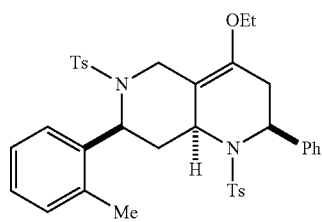
11'l 83 yield; white solid; IR (film) ν$_{max}$ 3063, 2978, 2921, 1699, 1345, 1162, 656 cm$^{-1}$; $^1$H NMR (400 MHz, CDCl$_3$) δ 7.65 (d, J=8.1 Hz, 2H), 7.38-7.30 (m, 6H), 7.28-7.23 (m, 2H), 7.17 (t, J=7.2 Hz, 1H), 7.11 (d, J=8.1 Hz, 2H), 7.00 (t, J=7.4 Hz, 1H), 6.92 (d, J=7.4 Hz, 1H), 6.87 (t, J=7.4 Hz, 1H), 6.78 (d, J=7.7 Hz, 1H), 5.23 (d, J=5.8 Hz, 1H), 4.79 (dd, J=11.3, 5.7 Hz, 1H), 4.43 (d, J=16.3 Hz, 1H), 4.26-4.20 (m, 2H), 3.86 (dq, J=9.6, 7.0 Hz, 1H), 3.70 (dq, J=9.6, 7.0 Hz, 1H), 2.59 (d, J=16.5 Hz, 1H), 2.45 (s, 3H), 2.36 (s, 3H), 2.18 (s, 3H), 2.14-2.10 (m, 1H), 2.02-1.97 (m, 1H), 1.28-1.20 (m, 4H); $^{13}$C NMR (100 MHz, CDCl$_3$) δ 143.5, 142.7, 142.6, 139.7, 138.9, 137.4, 136.7, 134.9, 130.1, 129.8, 129.0, 128.3, 127.4, 127.3, 127.0, 126.9, 126.8, 126.5, 125.7, 111.2, 63.5, 56.9, 52.8, 43.9, 38.5, 25.9, 21.5, 21.3, 19.0, 15.2; MS (MALDI) calcd. for C$_{37}$H$_{40}$N$_2$O$_5$S$_2$Na [M+Na]$^+$ 679.23. found 679.37.

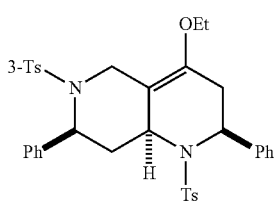
11'm

87% yield; white solid; IR (film) ν$_{max}$ 3057, 2978, 2914, 1699, 1301, 1161, 657 cm$^{-1}$; $^1$H NMR (500 MHz, CDCl$_3$) δ 7.55 (d, J=8.0 Hz, 2H), 7.45-7.44 (m, 1H), 7.36-7.23 (m, 9H), 7.17 (t, J=7.2 Hz, 1H), 7.12-7.09 (m, 3H), 6.92-6.91 (m, 2H), 5.18 (d, J=5.7 Hz, 1H), 4.85 (dd, J=10.4, 7.1 Hz, 1H), 4.35 (d, J=16.8 Hz, 1H), 4.15 (d, J=12.3 Hz, 1H), 4.09 (d, J=16.8 Hz, 1H), 3.81 (dq, J=9.7, 7.0 Hz, 1H), 3.65 (dq, J=9.7, 7.0 Hz, 1H), 2.54 (d, J=16.5 Hz, 1H), 2.45 (s, 3H), 2.31-2.24 (m, 4H), 1.94-1.89 (m, 1H), 1.23-1.16 (m, 4H); $^{13}$C NMR (125 MHz, CDCl$_3$) δ 143.4, 142.5, 140.6, 139.7, 139.6, 139.0, 137.4, 132.9, 129.8, 128.5, 128.2, 128.0, 127.5, 127.4, 127.3, 127.1, 126.8, 126.6, 124.2, 111.0, 63.4, 58.4, 52.6, 51.8, 42.6, 38.5, 25.6, 21.4, 21.2, 15.1; MS (MALDI) calcd. for C$_{36}$H$_{38}$N$_2$O$_5$S$_2$Na [M+Na]$^+$ 665.21. found 665.62.

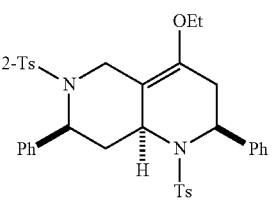
11'n

86% yield; white solid; IR (film) ν$_{max}$ 3060, 2978, 2924, 1703, 1338, 1158, 656 cm$^{-1}$; $^1$H NMR (500 MHz, CDCl$_3$) δ 7.73 (d, J=8.2 Hz, 2H), 7.44 (d, J=7.6 Hz, 2H), 7.34-7.20 (m, 8H), 7.12 (t, J=7.8 Hz, 1H), 6.97-6.90 (m, 2H), 6.83 (t, J=7.7 Hz, 2H), 6.56 (t, J=7.3 Hz, 2H), 5.35 (d, J=6.1 Hz, 1H), 4.66 (d, J=15.3 Hz, 1H), 4.53 (dd, J=10.6, 5.7 Hz, 1H), 4.42 (d, J=12.0 Hz, 1H), 3.88-3.82 (m, 2H), 3.68 (dq, J=9.6, 7.0 Hz, 1H), 2.60 (d, J=16.6 Hz, 1H), 2.48 (s, 3H), 2.45 (s, 3H), 2.13-2.09 (m, 1H), 2.04-2.00 (m, 1H), 1.19-1.06 (m, 4H); $^{13}$C NMR (125 MHz, CDCl$_3$) δ 143.5, 143.3, 140.0, 138.7, 137.5, 137.0, 131.9, 131.7, 129.9, 129.3, 128.2, 127.8, 127.7, 127.5, 127.4, 127.3, 126.7, 125.6, 110.9, 63.6, 60.0, 52.6, 42.5, 39.0, 25.3, 21.4, 19.8, 15.0; MS (MALDI) calcd. for C$_{36}$H$_{38}$N$_2$O$_5$S$_2$Na [M+Na]$^+$ 665.21. found 665.60.

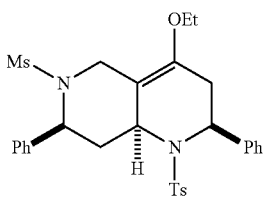
11'o

81% yield; white solid; IR (film) ν$_{max}$ 3031, 2979, 2930, 1701, 1341, 1164, 657 cm$^{-1}$; $^1$H NMR (500 MHz, CDCl$_3$) δ 7.79 (d, J=8.2 Hz, 2H), 7.43 (d, J=7.7 Hz, 2H), 7.34 (d, J=8.2 Hz, 2H), 7.30-7.26 (m, 2H), 7.24-7.18 (m, 4H), 7.03-7.02 (m, 2H), 5.37 (d, J=5.8 Hz, 1H), 4.88 (dd, J=9.7, 8.0 Hz, 1H), 4.53 (d, J=12.2 Hz, 1H), 4.26 (d, J=16.2 Hz, 1H), 4.07 (d, J=16.4 Hz, 1H), 3.85 (dq, J=9.6, 7.1 Hz, 1H), 3.64 (dq, J=9.6, 7.1 Hz, 1H), 2.64 (d, J=16.5 Hz, 1H), 2.43 (s, 3H), 2.35-2.30 (m, 1H), 2.28 (s, 3H), 2.14-2.09 (m, 1H), 1.26 (td, J=12.7, 10.2 Hz, 1H), 1.15 (t, J=7.1 Hz, 3H); $^{13}$C NMR (125 MHz, CDCl$_3$) δ 143.7, 142.7, 139.9, 139.8, 137.3, 130.0, 128.5, 128.3, 127.9, 127.6, 127.5, 127.3, 126.7, 110.4, 63.6, 58.4, 52.6, 51.7, 42.4, 39.4, 37.9, 25.5, 21.5, 15.1; MS (MALDI) calcd. for C$_{30}$H$_{34}$N$_2$O$_5$S$_2$Na [M+Na]$^+$ 589.18. found 589.33.

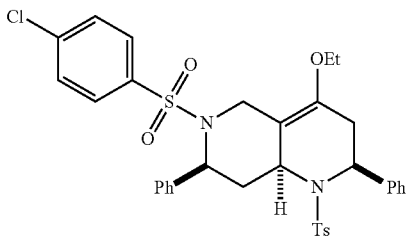

11'p

82% yield; white solid; IR (film) $v_{max}$ 3062, 2979, 2925, 1699, 1349, 1163, 657 cm$^{-1}$; $^1$H NMR (500 MHz, CDCl$_3$) δ 7.61 (d, J=8.2 Hz, 2H), 7.47 (d, J=8.6 Hz, 2H), 7.37 (d, J=7.6 Hz, 2H), 7.34-7.31 (m, 4H), 7.26-7.24 (m, 2H), 7.19-7.15 (m, 1H), 7.13-7.08 (m, 3H), 6.90 (d, J=6.7 Hz, 2H), 5.23 (d, J=5.7 Hz, 1H), 4.83 (dd, J=10.2, 7.4 Hz, 1H), 4.33 (d, J=16.7 Hz, 1H), 4.19-4.11 (m, 2H), 3.82 (dq, J=9.7, 7.0 Hz, 1H), 3.65 (dq, J=9.7, 7.0 Hz, 1H), 2.57 (d, J=16.4 Hz, 1H), 2.44 (s, 3H), 2.33-2.28 (m, 1H), 1.96-1.91 (m, 1H), 1.23 (td, J=12.7, 10.7 Hz, 1H), 1.16 (t, J=7.0 Hz, 3H); $^{13}$C NMR (125 MHz, CDCl$_3$) δ 143.7, 142.9, 140.2, 139.7, 138.5, 138.4, 137.2, 130.0, 128.9, 128.5, 128.3, 128.1, 127.5, 127.39, 127.37, 126.7, 126.6, 110.2, 63.3, 58.8, 52.7, 51.9, 42.8, 38.7, 25.6, 21.5, 15.2; MS (MALDI) calcd. for C$_{35}$H$_{35}$ClN$_2$O$_5$S$_2$Na [M+Na]$^+$ 685.16. found 685.24.

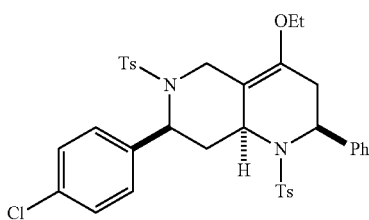

11'q

85% yield; white solid; IR (film) $v_{max}$ 3062, 2978, 2917, 1702, 1346, 1162, 655 cm$^{-1}$; $^1$H NMR (500 MHz, CDCl$_3$) δ 7.54 (d, J=8.2 Hz, 2H), 7.49 (d, J=8.6 Hz, 2H), 7.35 (d, J=7.6 Hz, 2H), 7.28-7.16 (m, 6H), 7.06 (d, J=8.5 Hz, 2H), 6.82 (d, J=8.4 Hz, 2H), 5.17 (d, J=5.7 Hz, 1H), 4.71 (dd, J=9.8, 7.4 Hz, 1H), 4.21-4.10 (m, 3H), 3.80 (dq, J=9.7, 7.0 Hz, 1H), 3.63 (dq, J=9.7, 7.0 Hz, 1H), 2.52 (d, J=16.6 Hz, 1H), 2.42 (s, 3H), 2.38 (s, 3H), 2.21-2.14 (m, 1H), 1.92-1.87 (m, 1H), 1.16-1.06 (m, 4H); $^{13}$C NMR (125 MHz, CDCl$_3$) δ 143.6, 143.2, 142.9, 139.6, 139.3, 137.4, 136.4, 132.9, 129.8, 129.4, 128.3, 128.1, 128.0, 127.48, 127.47, 127.1, 126.7, 110.2, 63.4, 57.9, 52.5, 51.7, 42.9, 38.7, 25.3, 21.5, 15.1; MS (MALDI) calcd. for C$_{36}$H$_{37}$ClN$_2$O$_5$S$_2$Na [M+Na]$^+$ 699.17. found 699.41.

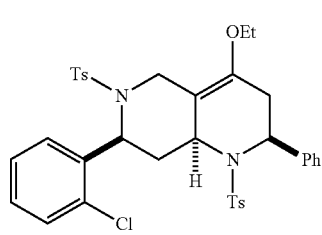

11'r

85% yield; white solid; IR (film) $v_{max}$ 3062, 2978, 2917, 1698, 1348, 1163, 656 cm$^{-1}$; $^1$H NMR (500 MHz, CDCl$_3$) δ 7.58 (d, J=8.2 Hz, 2H), 7.53 (d, J=8.2 Hz, 2H), 7.33-7.28 (m, 4H), 7.24-7.21 (m, 4H), 7.17-7.13 (m, 2H), 7.08-7.04 (m, 4H), 5.22 (d, J=5.7 Hz, 1H), 4.94 (dd, J=12.3, 6.9 Hz, 1H), 4.39-4.32 (m, 2H), 4.02 (d, J=12.2 Hz, 1H), 3.85 (dq, J=9.7, 7.1 Hz, 1H), 3.70 (dq, J=9.7, 7.1 Hz, 1H), 2.57 (d, J=16.4 Hz, 1H), 2.44 (s, 3H), 2.40 (s, 3H), 2.26-2.22 (m, 1H), 2.01-1.96 (m, 1H), 1.21 (t, J=7.1 Hz, 3H), 1.08 (td, J=12.6, 12.2 Hz, 1H); $^{13}$C NMR (125 MHz, CDCl$_3$) δ 143.6, 143.1, 142.9, 139.7, 138.8, 137.3, 135.9, 131.6, 129.8, 129.3, 129.2, 128.3, 128.2, 128.0, 127.4, 127.3, 127.2, 126.9, 126.6, 110.8, 63.5, 56.8, 52.7, 52.4, 43.9, 37.6, 26.0, 21.5, 15.2; MS (MALDI) calcd. for C$_{36}$H$_{37}$ClN$_2$O$_5$S$_2$Na [M+Na]$^+$ 699.17. found 699.38.

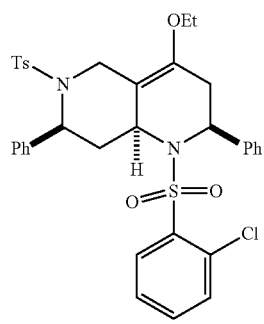

11's

81% yield; white solid; IR (film) $v_{max}$ 3063, 2979, 1700, 1346, 1162, 700 cm$^{-1}$; $^1$H NMR (500 MHz, CDCl$_3$) δ 8.10 (d, J=8.0 Hz, 1H), 7.53-7.38 (m, 7H), 7.27-7.24 (m, 2H), 7.20-7.10 (m, 6H), 6.93-6.91 (m, 2H), 5.08 (d, J=5.7 Hz, 1H), 4.71 (t, J=8.5 Hz, 1H), 4.30 (d, J=16.4 Hz, 1H), 4.16 (d, J=16.4 Hz, 1H), 3.92-3.86 (m, 1H), 3.79-3.73 (m, 1H), 2.60 (d, J=16.5 Hz, 1H), 2.36 (s, 3H), 2.29-2.25 (m, 2H), 1.31-1.24 (m, 4H); $^{13}$C NMR (125 MHz, CDCl$_3$) δ 143.1, 143.0, 140.8, 139.4, 137.2, 136.3, 133.9, 132.4, 132.1, 131.7, 129.4, 128.3, 128.0, 127.6, 127.3, 127.2, 127.1, 126.8, 110.8, 63.6, 58.8, 52.6, 52.2, 43.2, 38.6, 26.5, 21.4, 15.3; MS (MALDI) calcd. for C$_{35}$H$_{35}$ClN$_2$O$_5$S$_2$Na [M+Na]$^+$ 685.16. found 685.68.

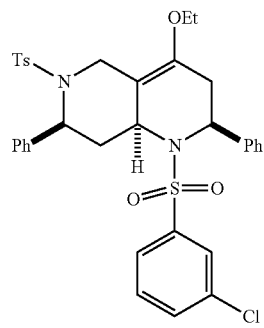

11't

70% yield; white solid; IR (film) $v_{max}$ 3063, 2979, 1672, 1345, 1164, 668 cm$^{-1}$; $^1$H NMR (500 MHz, CDCl$_3$) δ 7.73 (t, J=1.7 Hz, 1H), 7.58-7.55 (m, 2H), 7.51 (d, J=8.3 Hz, 2H), 7.45 (d, J=7.9 Hz, 1H), 7.37 (d, J=7.7 Hz, 2H), 7.27-7.24 (m, 2H), 7.22-7.18 (m, 3H), 7.14-7.10 (m, 3H), 6.91-6.89 (m, 2H), 5.20 (d, J=5.9 Hz, 1H), 4.84 (t, J=8.7 Hz, 1H), 4.28 (d, J=16.6 Hz, 1H), 4.17-4.12 (m, 2H), 3.83 (dq, J=9.8, 7.1 Hz, 1H), 3.67 (dq, J=9.8, 7.1 Hz, 1H), 2.58 (d, J=16.6 Hz, 1H), 2.35 (s, 3H), 2.26-2.21 (m, 1H), 2.00-1.95 (m, 1H), 1.23-1.17 (m, 4H); $^{13}$C NMR (125 MHz, CDCl$_3$) δ 143.1, 142.6, 142.1, 140.5, 139.2, 136.6, 135.3, 132.8, 130.6, 129.5, 128.4, 128.0, 127.6, 127.4, 127.2, 127.1, 126.6, 124.8, 110.6, 63.5, 58.1, 52.7, 52.0, 42.7, 38.2, 25.6, 21.4, 15.2; MS (MALDI) calcd. for C$_{35}$H$_{35}$ClN$_2$O$_5$S$_2$Li [M+Li]$^+$ 669.18. found 669.26.

11'u

60% yield; white solid; IR (film) $v_{max}$ 3063, 2979, 1699, 1348, 1163, 670 cm$^{-1}$; $^1$H NMR (500 MHz, CDCl$_3$) δ 7.62-7.58 (m, 4H), 7.36-7.25 (m, 8H), 7.19 (d, J=8.1 Hz, 2H), 7.16-7.11 (m, 3H), 5.48 (d, J=4.7 Hz, 1H), 4.90 (dd, J=11.3, 6.4 Hz, 1H), 4.75 (d, J=16.9 Hz, 1H), 3.76 (d, J=11.5 Hz, 1H), 3.45 (dq, J=9.9, 7.1 Hz, 1H), 3.34 (dq, J=9.9, 7.1 Hz, 1H), 2.94-2.89 (m, 1H), 2.50 (d, J=16.1 Hz, 1H), 2.42 (s, 3H), 2.39 (s, 3H), 1.94-1.83 (m, 2H), 0.97 (t, J=7.1 Hz, 3H); $^{13}$C NMR (125 MHz, CDCl$_3$) δ 143.8, 143.7, 143.1, 141.7, 138.4, 136.4, 135.8, 132.0, 129.7, 129.2, 128.8, 128.7, 128.4, 127.5, 127.3, 127.2, 126.5, 126.0, 110.1, 63.2, 58.2, 53.3, 52.5, 41.2, 38.6, 28.3, 21.5, 15.0; MS (MALDI) calcd. for C$_{36}$H$_{37}$ClN$_2$O$_5$S$_2$Na [M+Na]$^+$ 699.17. found 699.38.

11'v

76% yield; white solid; IR (film) $v_{max}$ 3059, 2980, 1697, 1341, 1162, 656 cm$^{-1}$; $^1$H NMR (500 MHz, CDCl$_3$) δ 7.73 (d, J=8.2 Hz, 2H), 7.46 (d, J=7.8 Hz, 2H), 7.37-7.26 (m, 7H), 7.21 (t, J=7.3 Hz, 1H), 7.00-6.94 (m, 2H), 6.85 (t, J=7.6 Hz, 2H), 6.68 (d, J=7.6 Hz, 2H), 5.35 (d, J=6.0 Hz, 1H), 4.74 (d, J=15.5 Hz, 1H), 4.65 (dd, J=10.6, 5.9 Hz, 1H), 4.42 (d, J=11.9 Hz, 1H), 4.03 (d, J=15.6 Hz, 1H), 3.86 (dq, J=9.7, 7.1 Hz, 1H), 3.69 (dq, J=9.7, 7.1 Hz, 1H), 2.61 (d, J=16.7 Hz, 1H), 2.45 (s, 3H), 2.14-2.04 (m, 2H), 1.28 (td, J=12.5, 10.9 Hz, 1H), 1.16 (t, J=7.1 Hz, 3H); $^{13}$C NMR (125 MHz, CDCl$_3$) δ 143.5, 143.1, 139.9, 138.6, 138.4, 137.5, 132.6, 131.7, 131.1, 131.0, 129.8, 128.3, 127.8, 127.6, 127.4, 127.2, 126.7, 126.3, 110.9, 63.5, 59.8, 52.6, 52.5, 43.6, 38.8, 25.4, 21.4, 15.0; MS (MALDI) calcd. for C$_{35}$H$_{35}$ClN$_2$O$_5$S$_2$Na [M+Na]$^+$ 685.16. found 685.67.

11'w

72% yield; white solid; IR (film) $v_{max}$ 3063, 2979, 1701, 1351, 1164, 699 cm$^{-1}$; $^1$H NMR (500 MHz, CDCl$_3$) δ 7.61 (d, J=8.2 Hz, 2H), 7.44-7.42 (m, 3H), 7.37-7.24 (m, 7H), 7.18 (t, J=7.2 Hz, 1H), 7.13-7.08 (m, 3H), 6.88 (d, J=7.1 Hz, 2H), 5.23 (d, J=5.6 Hz, 1H), 4.79 (dd, J=10.4, 7.3 Hz, 1H), 4.35 (d, J=16.1 Hz, 1H), 4.17-4.14 (m, 2H), 3.86 (dq, J=9.7, 7.1 Hz, 1H), 3.69 (dq, J=9.7, 7.1 Hz, 1H), 2.59 (d, J=16.5 Hz, 1H), 2.47 (s, 3H), 2.28-2.24 (m, 1H), 2.02-1.97 (m, 1H), 1.22-1.18 (m, 4H); $^{13}$C NMR (125 MHz, CDCl$_3$) δ 143.6, 143.0, 141.6, 139.8, 139.6, 137.3, 134.7, 132.1, 129.9, 128.3, 128.0, 127.5, 127.4, 127.3, 127.0, 126.8, 126.7, 125.0, 110.3, 63.4, 59.0, 52.6, 51.9, 42.9, 38.6, 25.7, 21.4, 15.2; MS (MALDI) calcd. for C$_{35}$H$_{35}$ClN$_2$O$_5$S$_2$Na [M+Na]$^+$ 685.16. found 685.59.

11'x

73% yield; white solid; IR (film) $v_{max}$ 3063, 2979, 1699, 1347, 1163, 664 cm$^{-1}$; $^1$H NMR (500 MHz, CDCl$_3$) δ 7.64 (d, J=8.6 Hz, 2H), 7.48-7.46 (m, 4H), 7.35 (d, J=7.6 Hz, 2H), 7.26 (t, J=7.5 Hz, 2H), 7.22-7.19 (m, 3H), 7.08-7.03 (m, 2H), 6.82 (d, J=7.2 Hz, 1H), 6.74 (s, 1H), 5.22 (d, J=5.8 Hz, 1H), 4.74 (dd, J=9.8, 7.6 Hz, 1H), 4.22 (d, J=16.0 Hz, 1H), 4.16-4.13 (m, 2H), 3.83 (dq, J=9.7, 7.1 Hz, 1H), 3.67 (dq, J=9.7, 7.1 Hz, 1H), 2.58 (d, J=16.6 Hz, 1H), 2.37 (s, 3H), 2.22-2.17 (m, 1H), 1.99-1.94 (m, 1H), 1.18 (t, J=7.1 Hz, 3H), 1.07 (td, J=12.7, 10.2 Hz, 1H); $^{13}$C NMR (125 MHz, CDCl$_3$) δ 143.3, 142.9, 142.5, 139.3, 139.2, 138.8, 136.4, 133.8, 129.5, 129.4, 129.3, 128.4, 128.1, 127.7, 127.4, 127.3, 127.1, 126.7, 125.0, 110.0, 63.4, 57.8, 52.7, 51.8, 42.8, 38.4, 25.6, 21.4, 15.1; MS (MALDI) calcd. for C$_{35}$H$_{34}$Cl$_2$N$_2$O$_5$S$_2$Na [M+Na]$^+$ 719.12. found 719.34.

11'y

56% yield; white solid; IR (film) $v_{max}$ 3031, 2978, 1700, 1347, 1162, 657 cm$^{-1}$; $^1$H NMR (500 MHz, CDCl$_3$) δ 7.56 (d, J=8.2 Hz, 2H), 7.49 (d, J=8.2 Hz, 2H), 7.37 (d, J=8.5 Hz, 2H), 7.30 (d, J=8.1 Hz, 2H), 7.22-7.20 (m, 4H), 7.17-7.15

(m, 3H), 6.92-6.90 (m, 2H), 5.12 (d, J=5.7 Hz, 1H), 4.82 (dd, J=9.8, 7.6 Hz, 1H), 4.26 (d, J=16.5 Hz, 1H), 4.15 (d, J=12.2 Hz, 1H), 4.09 (d, J=16.8 Hz, 1H), 3.79 (dq, J=9.8, 7.1 Hz, 1H), 3.63 (dq, J=9.8, 7.1 Hz, 1H), 2.48-2.45 (m, 4H), 2.38 (s, 3H), 2.30-2.26 (m, 1H), 1.94-1.89 (m, 1H), 1.21-1.14 (m, 4H); $^{13}$C NMR (125 MHz, CDCl$_3$) δ 143.7, 143.0, 142.3, 140.6, 138.9, 137.1, 136.6, 131.4, 129.8, 129.4, 129.3, 128.1, 127.2, 127.1, 126.7, 126.5, 121.4, 110.9, 63.4, 58.2, 52.2, 51.8, 42.6, 38.8, 25.5, 21.5, 21.4, 15.1; MS (MALDI) calcd. for C$_{36}$H$_{37}$BrN$_2$O$_5$S$_2$Na [M+Na]$^+$ 745.12. found 745.31.

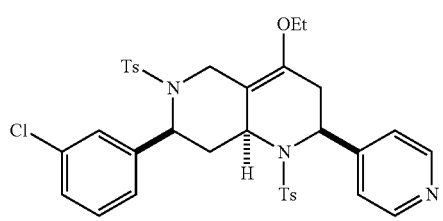

11'z

80% yield; white solid; IR (film) ν$_{max}$ 3031, 2979, 2925, 1700, 1346, 1162, 656 cm$^{-1}$; $^1$H NMR (500 MHz, CDCl$_3$) δ 8.47 (d, J=5.7 Hz, 2H), 7.55 (d, J=8.2 Hz, 2H), 7.46 (d, J=8.2 Hz, 2H), 7.29 (d, J=8.0 Hz, 2H), 7.24 (d, J=5.7 Hz, 2H), 7.08-7.02 (m, 2H), 6.82-6.80 (m, 2H), 5.07 (d, J=5.3 Hz, 1H), 4.81 (dd, J=10.5, 7.3 Hz, 1H), 4.41 (d, J=17.0 Hz, 1H), 4.09 (d, J=11.8 Hz, 1H), 3.98 (d, J=17.2 Hz, 1H), 3.79 (dq, J=9.7, 7.1 Hz, 1H), 3.62 (dq, J=9.7, 7.1 Hz, 1H), 2.50 (d, J=16.5 Hz, 1H), 2.42 (s, 3H), 2.38-2.35 (m, 4H), 1.88-1.84 (m, 1H), 1.17-1.10 (m, 4H); $^{13}$C NMR (125 MHz, CDCl$_3$) δ 149.9, 149.0, 144.0, 143.3, 142.6, 142.3, 136.6, 136.5, 134.0, 130.0, 129.6, 129.4, 127.4, 127.0, 126.8, 126.3, 124.4, 122.2, 110.7, 63.5, 57.7, 52.1, 51.9, 42.4, 39.1, 25.2, 21.5, 21.4, 15.1; MS (MALDI) calcd. for C$_{35}$H$_{36}$ClN$_3$O$_5$S$_2$Na [M+Na]$^+$ 700.17. found 701.25.

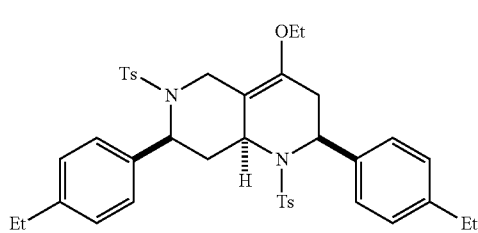

11'aa

70% yield; white solid; IR (film) ν$_{max}$ 2965, 2925, 1702, 1346, 1162, 655 cm$^{-1}$; $^1$H NMR (500 MHz, CDCl$_3$) δ 7.57 (d, J=8.2 Hz, 2H), 7.48 (d, J=8.2 Hz, 2H), 7.30-7.27 (m, 4H), 7.19 (d, J=8.0 Hz, 2H), 7.09 (d, J=8.2 Hz, 2H), 6.93 (d, J=8.2 Hz, 2H), 6.82 (d, J=8.2 Hz, 2H), 5.18 (d, J=5.8 Hz, 1H), 4.76 (dd, J=9.8, 7.6 Hz, 1H), 4.24-4.15 (m, 3H), 3.82 (dq, J=9.8, 7.1 Hz, 1H), 3.65 (dq, J=9.8, 7.1 Hz, 1H), 2.61-2.51 (m, 5H), 2.44 (s, 3H), 2.37 (s, 3H), 2.23-2.17 (m, 1H), 1.96-1.90 (m, 1H), 1.20-1.15 (m, 10H); $^{13}$C NMR (125 MHz, CDCl$_3$) δ 143.5, 143.4, 143.1, 142.8, 142.7, 137.9, 137.6, 136.9, 136.8, 129.8, 129.3, 127.7, 127.5, 127.4, 127.2, 126.8, 126.7, 110.8, 63.4, 58.4, 52.4, 51.8, 42.8, 38.5, 28.3, 25.6, 21.5, 21.4, 15.5, 15.4, 15.1; MS (MALDI) calcd. for C$_{40}$H$_{46}$N$_2$O$_5$S$_2$Na [M+Na]$^+$ 721.27. found 721.18.

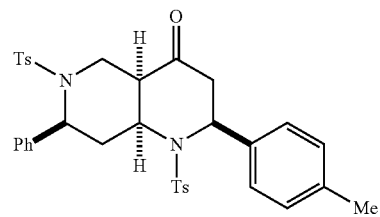

H7

89% yield; white solid; IR (film) ν$_{max}$ 3031, 2919, 2868, 1713, 1347, 1162, 659 cm$^{-1}$; $^1$H NMR (500 MHz, CDCl$_3$) δ 7.76 (d, J=8.2 Hz, 2H), 7.46 (d, J=7.9 Hz, 2H), 7.38 (d, J=8.0 Hz, 2H), 7.24 (d, J=8.2 Hz, 2H), 7.18 (d, J=8.1 Hz, 2H), 7.13-7.10 (m, 3H), 7.02 (d, J=8.0 Hz, 2H), 6.86 (dd, J=7.5, 1.0 Hz, 2H), 5.67 (d, J=6.6 Hz, 1H), 4.91 (dd, J=11.3, 7.0 Hz, 1H), 4.60-4.56 (m, 1H), 3.80 (dd, J=15.4, 8.0 Hz, 1H), 3.43 (dd, J=15.4, 9.3 Hz, 1H), 2.92 (dd, J=14.8, 1.9 Hz, 1H), 2.67 (dd, J=17.5, 8.8 Hz, 1H), 2.48 (s, 3H), 2.38 (s, 3H), 2.23-2.19 (m, 4H), 1.79-1.74 (m, 1H), 0.99 (td, J=13.5, 11.5 Hz, 1H); $^{13}$C NMR (125 MHz, CDCl$_3$) δ 206.7, 144.1, 143.2, 140.2, 137.8, 137.4, 137.1, 136.3, 130.3, 129.4, 129.1, 128.2, 127.3, 127.2, 127.0, 126.6, 125.9, 58.5, 54.9, 53.2, 45.4, 41.5, 40.5, 36.2, 21.5, 21.4, 20.8; MS (MALDI) calcd. for C$_{35}$H$_{36}$N$_2$O$_5$S$_2$Na [M+Na]$^+$ 651.20. found 651.52.

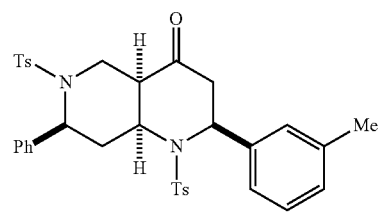

H8

92% yield; white solid; IR (film) ν$_{max}$ 3060, 2922, 1713, 1347, 1162, 660 cm$^{-1}$; $^1$H NMR (500 MHz, CDCl$_3$) δ 7.77 (d, J=8.0 Hz, 2H), 7.44 (d, J=8.1 Hz, 2H), 7.38 (d, J=8.1 Hz, 2H), 7.20-7.08 (m, 8H), 6.96 (d, J=7.2 Hz, 1H), 6.86 (d, J=7.0 Hz, 2H), 5.67 (d, J=6.7 Hz, 1H), 4.91 (dd, J=11.3, 7.0 Hz, 1H), 4.62-4.58 (m, 1H), 3.79 (dd, J=15.4, 8.0 Hz, 1H), 3.47 (dd, J=15.4, 9.1 Hz, 1H), 2.93 (dd, J=14.8, 1.4 Hz, 1H), 2.67 (dd, J=17.5, 8.7 Hz, 1H), 2.48 (s, 3H), 2.37 (s, 3H), 2.24-2.20 (m, 4H), 1.79-1.74 (m, 1H), 1.04 (td, J=12.5, 11.6 Hz, 1H); $^{13}$C NMR (125 MHz, CDCl$_3$) δ 206.6, 144.1, 143.2, 140.2, 139.4, 138.2, 137.4, 137.1, 130.3, 129.4, 128.7, 128.3, 128.2, 128.1, 127.3, 127.0, 126.6, 125.9, 124.2, 58.5, 55.1, 53.3, 45.4, 41.4, 40.5, 36.2, 21.5, 21.4, 21.3; MS (MALDI) calcd. for C$_{35}$H$_{36}$N$_2$O$_5$S$_2$Na [M+Na]$^+$ 651.20. found 651.57.

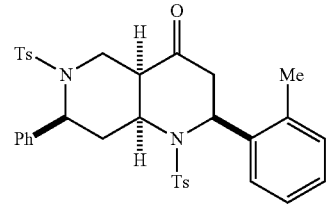

H9

83% yield; white solid; IR (film) ν$_{max}$ 3060, 2959, 1722, 1350, 1162, 660 cm$^{-1}$; $^1$H NMR (500 MHz, CDCl$_3$) δ 7.76

(d, J=8.0 Hz, 2H), 7.36-7.34 (m, 4H), 7.14-7.08 (m, 7H), 7.03-7.01 (m, 2H), 6.85-6.83 (m, 2H), 5.81 (t, J=5.5 Hz, 1H), 4.77 (dd, J=11.4, 6.5 Hz, 1H), 4.53-4.48 (m, 1H), 3.78 (dd, J=14.8, 7.5 Hz, 1H), 3.47 (dd, J=14.8, 8.9 Hz, 1H), 2.88 (dd, J=16.2, 4.7 Hz, 1H), 2.72-2.66 (m, 2H), 2.53 (s, 3H), 2.47 (s, 3H), 2.36 (s, 3H), 1.78-1.73 (m, 1H), 1.27 (td, J=13.5, 11.6 Hz, 1H); $^{13}$C NMR (125 MHz, CDCl$_3$) δ 207.2, 144.4, 143.2, 140.0, 138.2, 137.3, 136.7, 136.3, 131.2, 129.3, 128.2, 128.1, 127.5, 127.4, 127.1, 126.3, 126.2, 126.0, 58.9, 53.9, 52.5, 45.2, 43.5, 41.8, 36.0, 21.5, 21.4, 20.2; MS (MALDI) calcd. for C$_{35}$H$_{36}$N$_2$O$_5$S$_2$Na [M+Na]$^+$ 651.20. found 651.78.

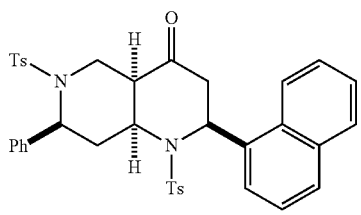

H10

85% yield; white solid; IR (film) ν$_{max}$ 3060, 2951, 2923, 1704, 1352, 1161, 661 cm$^{-1}$; $^1$H NMR (500 MHz, CDCl$_3$) δ 8.71 (d, J=8.6 Hz, 1H), 7.87 (d, J=8.3 Hz, 2H), 7.78 (d, J=7.7 Hz, 1H), 7.71 (d, J=7.7 Hz, 1H), 7.65-7.62 (m, 1H), 7.51 (t, J=7.5 Hz, 1H), 7.37-7.24 (m, 6H), 7.12-7.08 (m, 3H), 7.05-7.02 (m, 2H), 6.69 (d, J=7.2 Hz, 2H), 6.55 (dd, J=6.7, 2.5 Hz, 1H), 4.53 (dd, J=11.3, 6.8 Hz, 1H), 4.33-4.28 (m, 1H), 3.90 (dd, J=15.1, 7.8 Hz, 1H), 3.42 (dd, J=15.1, 9.3 Hz, 1H), 3.11 (dd, J=15.9, 2.9 Hz, 1H), 2.98 (dd, J=16.0, 7.1 Hz, 1H), 2.48 (s, 3H), 2.37 (s, 3H), 1.17-1.13 (m, 1H), 1.03 (td, J=13.5, 11.6 Hz, 1H); $^{13}$C NMR (125 MHz, CDCl$_3$) δ 207.9, 144.6, 143.2, 139.9, 136.8, 136.0, 135.8, 133.8, 131.4, 130.2, 130.0, 129.3, 128.7, 128.1, 127.7, 127.4, 127.0, 126.7, 126.2, 126.0, 125.0, 124.4, 124.3, 58.5, 52.8, 52.7, 45.2, 43.8, 41.4, 34.5, 21.6, 21.4; MS (MALDI) calcd. for C$_{38}$H$_{36}$N$_2$O$_5$S$_2$Na [M+Na]$^+$ 687.20. found 688.43.

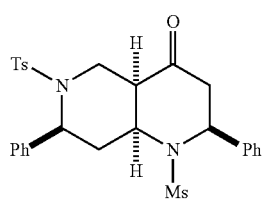

H11

80% yield; white solid; IR (film) ν$_{max}$ 3062, 2928, 1713, 1344, 1157, 661 cm$^{-1}$; $^1$H NMR (500 MHz, CDCl$_3$) δ 7.47 (d, J=8.0 Hz, 2H), 7.35 (d, J=7.4 Hz, 2H), 7.24-7.11 (m, 8H), 6.90 (d, J=6.2 Hz, 2H), 5.69 (d, J=5.9 Hz, 1H), 4.83 (dd, J=10.8, 7.2 Hz, 1H), 4.17 (t, J=10.7 Hz, 1H), 3.95 (dd, J=15.3, 7.9 Hz, 1H), 3.56 (dd, J=15.3, 9.1 Hz, 1H), 3.17 (d, J=15.0 Hz, 1H), 3.01 (dd, J=17.1, 8.5 Hz, 1H), 2.93 (s, 3H), 2.81 (dd, J=14.9, 7.0 Hz, 1H), 2.37 (s, 3H), 1.78-1.74 (m, 1H), 1.01 (td, J=12.5, 11.9 Hz, 1H); $^{13}$C NMR (125 MHz, CDCl$_3$) δ 206.2, 143.4, 140.0, 139.4, 136.9, 129.6, 128.6, 128.3, 128.1, 127.4, 127.3, 127.0, 125.8, 58.5, 55.0, 52.9, 45.9, 42.8, 40.7, 40.1, 36.1, 21.4; MS (MALDI) calcd. for C$_{28}$H$_{30}$N$_2$O$_5$S$_2$Na [M+Na]$^+$ 561.15. found 561.52.

2A2

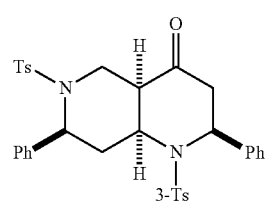

2-Ts

90% yield; white solid; IR (film) ν$_{max}$ 3062, 2975, 1713, 1346, 1162, 735 cm$^{-1}$; $^1$H NMR (500 MHz, CDCl$_3$) δ 8.05 (d, J=7.6 Hz, 1H), 7.54 (t, J=7.3 Hz, 1H), 7.42-7.36 (m, 4H), 7.26-7.24 (m, 2H), 7.19-7.16 (m, 2H), 7.14-7.06 (m, 6H), 6.83 (d, J=7.2 Hz, 2H), 5.62 (d, J=6.5 Hz, 1H), 4.81 (dd, J=11.3, 6.8 Hz, 1H), 4.61-4.57 (m, 1H), 3.81 (dd, J=15.2, 7.9 Hz, 1H), 3.55 (dd, J=15.2, 8.8 Hz, 1H), 3.07 (dd, J=14.9, 1.4 Hz, 1H), 2.92 (dd, J=17.0, 8.5 Hz, 1H), 2.73 (s, 3H), 2.33 (s, 3H), 1.73-1.70 (m, 1H), 1.03 (td, J=12.6, 11.7 Hz, 1H); $^{13}$C NMR (125 MHz, CDCl$_3$) δ 206.8, 143.2, 140.0, 139.4, 137.2, 137.1, 136.9, 133.4, 133.2, 130.1, 129.4, 128.5, 128.2, 128.1, 127.4, 127.3, 126.9, 126.8, 126.0, 58.8, 55.0, 52.7, 46.4, 42.3, 40.8, 36.1, 21.4, 21.0; MS (MALDI) calcd. for C$_{34}$H$_{34}$N$_2$O$_5$S$_2$Na [M+Na]$^+$ 637.18. found 637.48.

2A3

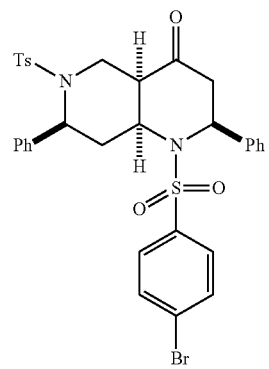

3-Ts

85% yield; white solid; IR (film) ν$_{max}$ 3063, 2923, 1713, 1347, 1158, 661 cm$^{-1}$; $^1$H NMR (500 MHz, CDCl$_3$) δ 7.84 (s, 1H), 7.69-7.67 (m, 1H), 7.48-7.47 (m, 2H), 7.42-7.36 (m, 4H), 7.24-7.21 (m, 2H), 7.18-7.14 (m, 3H), 7.11-7.06 (m, 3H), 6.82-6.81 (m, 2H), 5.75 (d, J=6.7 Hz, 1H), 4.96 (dd, J=11.2, 7.1 Hz, 1H), 4.69-4.65 (m, 1H), 3.76 (dd, J=15.3, 8.0 Hz, 1H), 3.41 (dd, J=15.3, 9.2 Hz, 1H), 2.97 (dd, J=14.8, 1.9 Hz, 1H), 2.69 (dd, J=17.5, 8.9 Hz, 1H), 2.50 (s, 3H), 2.36 (s, 3H), 2.29 (dd, J=14.5, 7.2 Hz, 1H), 1.80-1.76 (m, 1H), 0.97 (td, J=13.5, 11.4 Hz, 1H); $^{13}$C NMR (125 MHz, CDCl$_3$) δ 206.6, 143.2, 140.2, 140.0, 139.4, 136.9, 134.0, 129.5, 129.4, 128.5, 128.2, 128.0, 127.3, 127.2, 127.1, 125.6, 123.5, 58.2, 55.2, 53.3, 45.6, 41.4, 40.4, 36.1, 21.4, 21.3; MS (MALDI) calcd. for C$_{34}$H$_{34}$N$_2$O$_5$S$_2$Na [M+Na]$^+$ 637.18. found 637.64.

2A4

90% yield; white solid; IR (film) ν$_{max}$ 3062, 2917, 1713, 1348, 1164, 661 cm$^{-1}$; $^1$H NMR (500 MHz, CDCl$_3$) δ 7.81-7.74 (m, 4H), 7.44-7.37 (m, 4H), 7.26-7.08 (m, 8H), 6.83 (d, J=6.3 Hz, 2H), 5.74 (d, J=6.3 Hz, 1H), 4.96 (t, J=8.8 Hz, 1H), 4.62 (t, J=11.0 Hz, 1H), 3.77 (dd, J=14.8, 7.5 Hz, 1H), 3.41 (dd, J=13.4, 10.1 Hz, 1H), 3.01 (d, J=14.9 Hz, 1H), 2.72 (dd, J=15.9, 7.5 Hz, 1H), 2.37 (s, 3H), 2.28 (dd, J=16.4, 10.7 Hz, 1H), 1.80-1.76 (m, 1H), 0.97 (td, J=12.2, 11.1 Hz, 1H); $^{13}$C NMR (125 MHz, CDCl$_3$) δ 206.1, 143.3, 140.0, 139.4, 139.0, 136.8, 133.0, 129.4, 128.6, 128.3, 128.2, 128.1, 127.4, 127.3, 127.1, 58.1, 55.3, 53.4, 45.6, 41.6, 40.3, 36.0, 21.4; MS (MALDI) calcd. for C$_{33}$H$_{31}$BrN$_2$O$_5$S$_2$Na [M+Na]$^+$ 703.07. found 703.63.

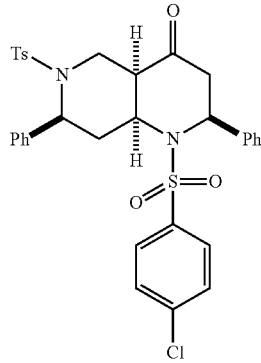

2A5

88% yield; white solid; IR (film) ν$_{max}$ 3062, 2923, 2865, 1725, 1334, 1162, 667 cm$^{-1}$; $^1$H NMR (500 MHz, CDCl$_3$) δ 7.88 (d, J=8.6 Hz, 2H), 7.59 (d, J=8.6 Hz, 2H), 7.44 (d, J=8.3 Hz, 2H), 7.38 (d, J=8.0 Hz, 2H), 7.24 (t, J=8.3 Hz, 2H), 7.19-7.16 (m, 3H), 7.13-7.08 (m, 3H), 6.83-6.82 (m, 2H), 5.75 (d, J=6.6 Hz, 1H), 4.96 (dd, J=11.1, 7.2 Hz, 1H), 4.63 (t, J=10.5 Hz, 1H), 3.77 (dd, J=15.5, 8.1 Hz, 1H), 3.41 (dd, J=15.5, 9.2 Hz, 1H), 3.01 (dd, J=14.9, 2.0 Hz, 1H), 2.72 (dd, J=17.6, 8.8 Hz, 1H), 2.37 (s, 3H), 2.31 (dd, J=14.7, 7.1 Hz, 1H), 1.80-1.76 (m, 1H), 0.97 (td, J=13.5, 11.5 Hz, 1H); $^{13}$C NMR (125 MHz, CDCl$_3$) δ 203.4, 142.9, 140.8, 139.8, 138.0, 137.4, 135.3, 129.8, 129.0, 128.6, 128.5, 127.8, 127.5, 127.4, 127.0, 126.5, 55.6, 55.2, 51.6, 46.5, 42.4, 37.7, 33.0, 21.6; MS (MALDI) calcd. for C$_{33}$H$_{31}$ClN$_2$O$_5$S$_2$Na [M+Na]$^+$ 657.12. found 657.69.

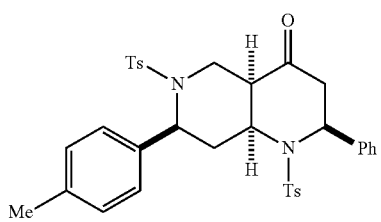

2A7

89% yield; white solid; IR (film) ν$_{max}$ 3029, 2922, 2864, 1712, 1347, 1162, 660 cm$^{-1}$; $^1$H NMR (500 MHz, CDCl$_3$) δ 7.76 (d, J=8.2 Hz, 2H), 7.44 (d, J=8.2 Hz, 2H), 7.39-7.37 (m, 4H), 7.24-7.21 (m, 2H), 7.18-7.15 (m, 3H), 6.89 (d, J=7.8 Hz, 1H), 6.73 (d, J=8.0 Hz, 2H), 5.71 (d, J=6.5 Hz, 1H), 4.87 (dd, J=11.1, 7.0 Hz, 1H), 4.61-4.56 (m, 1H), 3.77 (dd, J=15.4, 8.0 Hz, 1H), 3.44 (dd, J=15.3, 9.1 Hz, 1H), 2.94 (d, J=14.8 Hz, 1H), 2.67 (dd, J=17.4, 8.7 Hz, 1H), 2.48 (s, 3H), 2.38 (s, 3H), 2.25-2.21 (m, 4H), 1.76-1.72 (m, 1H), 0.98 (td, J=12.5, 11.6 Hz, 1H); $^{13}$C NMR (125 MHz, CDCl$_3$) δ 206.6, 144.2, 143.2, 139.4, 137.4, 137.2, 137.0, 130.3, 129.4, 128.8, 128.5, 128.0, 127.3, 127.0, 126.6, 125.8, 58.3, 55.2, 53.4, 45.5, 41.4, 40.4, 36.3, 21.6, 21.4, 20.9; MS (MALDI) calcd. for C$_{35}$H$_{36}$N$_2$O$_5$S$_2$Na [M+Na]$^+$ 651.20. found 651.56.

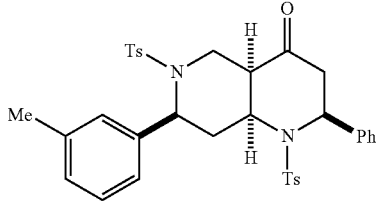

2A8

88% yield; white solid; IR (film) ν$_{max}$ 3061, 2922, 2864, 1713, 1348, 1162, 660 cm$^{-1}$; $^1$H NMR (500 MHz, CDCl$_3$) δ 7.79 (d, J=7.9 Hz, 2H), 7.43 (d, J=8.0 Hz, 2H), 7.40-7.38 (m, 4H), 7.25-7.22 (m, 2H), 7.17-7.16 (m, 3H), 6.98 (t, J=7.5 Hz, 1H), 6.91 (d, J=7.4 Hz, 1H), 6.65 (d, J=7.4 Hz, 1H), 6.51 (s, 1H), 5.73 (d, J=6.5 Hz, 1H), 4.84 (dd, J=11.2, 6.9 Hz, 1H), 4.63-4.58 (m, 1H), 3.79 (dd, J=15.3, 7.9 Hz, 1H), 3.47 (dd, J=15.2, 9.1 Hz, 1H), 2.96 (d, J=14.8 Hz, 1H), 2.68 (dd, J=17.4, 8.7 Hz, 1H), 2.48 (s, 3H), 2.37 (s, 3H), 2.28-2.22 (m, 1H), 2.11 (s, 3H), 1.76-1.72 (m, 1H), 0.97 (td, J=13.0, 12.7 Hz, 1H); $^{13}$C NMR (125 MHz, CDCl$_3$) δ 206.6, 144.2, 143.1, 139.9, 139.5, 137.7, 137.4, 137.2, 130.3, 129.3, 128.5, 128.1, 128.0, 127.9, 127.3, 127.0, 126.7, 126.6, 123.2, 58.6, 55.2, 53.4, 45.6, 41.4, 40.6, 36.4, 21.5, 21.4, 21.1; MS (MALDI) calcd. for C$_{35}$H$_{36}$N$_2$O$_5$S$_2$Na [M+Na]$^+$ 651.20. found 651.84.

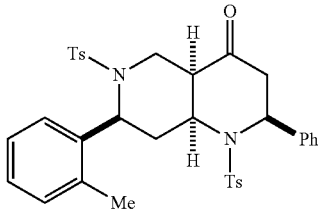

2A9

91% yield; white solid; IR (film) ν$_{max}$ 3058, 2953, 2914, 1713, 1362, 1162, 660 cm$^{-1}$; $^1$H NMR (500 MHz, CDCl$_3$) δ 7.80 (d, J=8.2 Hz, 2H), 7.39 (d, J=8.0 Hz, 2H), 7.36-7.33 (m, 4H), 7.19 (t, J=7.6 Hz, 2H), 7.13-7.10 (m, 3H), 7.00-6.95 (m, 2H), 6.80 (t, J=7.2 Hz, 1H), 6.66 (d, J=7.7 Hz, 1H), 5.72 (d, J=6.2 Hz, 1H), 5.01 (dd, J=11.7, 6.2 Hz, 1H), 4.62-4.57 (m, 1H), 3.90 (dd, J=15.2, 7.8 Hz, 1H), 3.58 (dd, J=15.3, 9.2 Hz, 1H), 2.96 (dd, J=14.9, 2.2 Hz, 1H), 2.76 (dd, J=17.4, 8.8 Hz, 1H), 2.48 (s, 3H), 2.35 (s, 3H), 2.29 (dd, J=14.7, 7.2 Hz, 1H), 2.21 (s, 3H), 1.68-1.64 (m, 1H), 0.90 (td, J=12.7, 12.0 Hz, 1H); $^{13}$C NMR (125 MHz, CDCl$_3$) δ 206.5, 144.2, 143.1, 139.3, 138.8, 137.3, 136.9, 134.3, 130.3, 130.2, 129.3, 128.5, 128.0, 127.2, 127.1, 127.0, 126.7, 125.9, 125.1, 56.0, 55.1, 53.6, 45.8, 41.6, 41.5, 36.2, 21.5, 21.4, 19.0; MS (MALDI) calcd. for C$_{35}$H$_{36}$N$_2$O$_5$S$_2$Na [M+Na]$^+$ 651.20. found 651.84.

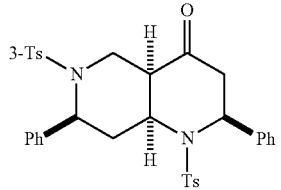

2A10

90% yield; white solid; IR (film) ν$_{max}$ 3062, 2921, 1713, 1347, 1162, 699 cm$^{-1}$; $^1$H NMR (500 MHz, CDCl$_3$) δ 7.78 (d, J=8.2 Hz, 2H), 7.39-7.38 (m, 5H), 7.29-7.21 (m, 5H), 7.16 (t, J=7.3 Hz, 1H), 7.11-7.06 (m, 3H), 6.84-6.82 (m, 2H), 5.73 (d, J=6.7 Hz, 1H), 4.93 (dd, J=11.3, 7.0 Hz, 1H), 4.65-4.60 (m, 1H), 3.82 (dd, J=15.2, 8.0 Hz, 1H), 3.46 (dd, J=15.3, 9.2 Hz, 1H), 2.96 (dd, J=14.8, 2.0 Hz, 1H), 2.68 (dd, J=17.5, 8.9 Hz, 1H), 2.49 (s, 3H), 2.28-2.23 (m, 4H), 1.79-1.74 (m, 1H), 0.98 (td, J=13.5, 11.5 Hz, 1H); $^{13}$C NMR (125 MHz, CDCl$_3$) δ 206.6, 144.2, 140.0, 139.9, 139.4, 139.1, 137.4, 133.1, 130.3, 128.6, 128.5, 128.1, 128.0, 127.40, 127.39, 127.3, 126.6, 125.9, 124.0, 58.7, 55.1, 53.3, 45.6, 41.4, 40.5, 36.4, 21.5, 21.1; MS (MALDI) calcd. for C$_{34}$H$_{34}$N$_2$O$_5$S$_2$Na [M+Na]$^+$ 637.18. found 637.52.

2A11

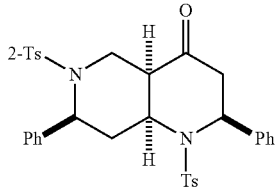

90% yield; white solid; IR (film) ν$_{max}$ 3062, 2921, 1713, 1309, 1162, 699 cm$^{-1}$; $^1$H NMR (500 MHz, CDCl$_3$) δ 7.93 (d, J=8.2 Hz, 2H), 7.66 (dd, J=7.9, 0.9 Hz, 1H), 7.44-7.41 (m, 4H), 7.31-7.23 (m, 3H), 7.16 (t, J=7.3 Hz, 1H), 7.10 (t, J=7.6 Hz, 1H), 7.05-7.01 (m, 2H), 6.95-6.92 (m, 2H), 6.62 (d, J=7.3 Hz, 2H), 5.82 (d, J=6.5 Hz, 1H), 4.89-4.84 (m, 1H), 4.70 (dd, J=11.2, 6.5 Hz, 1H), 3.75 (dd, J=15.2, 7.5 Hz, 1H), 3.66 (dd, J=15.2, 8.3 Hz, 1H), 3.02 (dd, J=14.8, 2.2 Hz, 1H), 2.71 (dd, J=16.4, 8.1 Hz, 1H), 2.48 (s, 3H), 2.39 (dd, J=14.3, 7.2 Hz, 1H), 2.28 (s, 3H), 1.73-1.68 (m, 1H), 1.08 (td, J=13.4, 11.4 Hz, 1H); $^{13}$C NMR (125 MHz, CDCl$_3$) δ 206.5, 144.2, 139.8, 138.0, 137.3, 137.2, 132.6, 132.2, 130.4, 129.9, 128.5, 128.0, 127.9, 127.3, 126.8, 126.1, 125.8, 58.8, 55.5, 53.6, 46.0, 41.6, 40.4, 36.0, 21.5, 19.8; MS (MALDI) calcd. for C$_{34}$H$_{34}$N$_2$O$_5$S$_2$Na [M+Na]$^+$ 637.18. found 637.50.

2B2

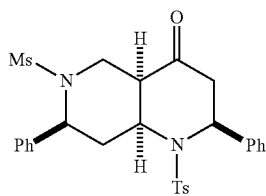

87% yield; white solid; IR (film) ν$_{max}$ 3062, 3027, 2925, 1713, 1333, 1163, 670 cm$^{-1}$; $^1$H NMR (500 MHz, CDCl$_3$) δ 7.91 (d, J=8.2 Hz, 2H), 7.43-7.39 (m, 4H), 7.26-7.16 (m, 6H), 7.00-6.98 (m, 2H), 5.83 (d, J=6.7 Hz, 1H), 4.87 (dd, J=11.2, 7.1 Hz, 1H), 4.75-4.71 (m, 1H), 3.80 (dd, J=15.0, 8.2 Hz, 1H), 3.48 (dd, J=14.9, 9.2 Hz, 1H), 3.03 (dd, J=14.8, 1.7 Hz, 1H), 2.75 (dd, J=17.6, 8.8 Hz, 1H), 2.46 (s, 3H), 2.43-2.39 (m, 4H), 1.80-1.74 (m, 1H), 1.04 (td, J=13.3, 11.5 Hz, 1H); $^{13}$C NMR (125 MHz, CDCl$_3$) δ 206.6, 144.3, 139.6, 139.5, 137.2, 130.4, 128.7, 128.5, 128.1, 128.0, 127.4, 126.7, 126.0, 58.2, 55.2, 53.2, 46.2, 41.6, 40.4, 40.3, 36.7, 21.5; MS (MALDI) calcd. for C$_{28}$H$_{30}$N$_2$O$_5$S$_2$Na [M+Na]$^+$ 561.15. found 561.45.

2B3

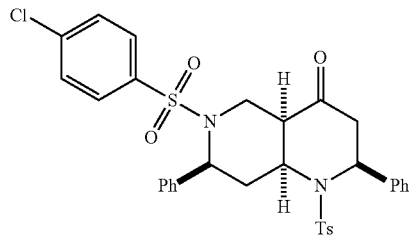

90% yield; white solid; IR (film) ν$_{max}$ 3063, 2917, 1713, 1349, 1163, 699 cm$^{-1}$; $^1$H NMR (500 MHz, CDCl$_3$) δ 7.82 (d, J=8.0 Hz, 2H), 7.41-7.36 (m, 6H), 7.28-7.20 (m, 4H), 7.17-7.10 (m, 2H), 7.07-7.02 (m, 2H), 6.78 (d, J=7.8 Hz, 2H), 5.75 (d, J=6.5 Hz, 1H), 4.85 (dd, J=11.4, 6.7 Hz, 1H), 4.65-4.60 (m, 1H), 3.78 (dd, J=15.1, 7.8 Hz, 1H), 3.52 (dd, J=15.1, 9.0 Hz, 1H), 2.99 (d, J=14.9 Hz, 1H), 2.70 (dd, J=17.1, 8.6 Hz, 1H), 2.47 (s, 3H), 2.31 (dd, J=14.9, 7.1 Hz, 1H), 1.76-1.72 (m, 1H), 1.00 (td, J=12.6, 11.8 Hz, 1H); $^{13}$C NMR (125 MHz, CDCl$_3$) δ 206.3, 144.3, 139.4, 139.3, 138.7, 138.6, 137.3, 130.4, 128.9, 128.5, 128.3, 128.2, 128.0, 127.6, 127.3, 126.6, 126.1, 59.0, 55.1, 53.4, 45.6, 41.4, 40.8, 36.5, 21.5; MS (MALDI) calcd. for C$_{33}$H$_{31}$ClN$_2$O$_5$S$_2$Na [M+Na]$^+$ 657.12. found 657.43.

2B4

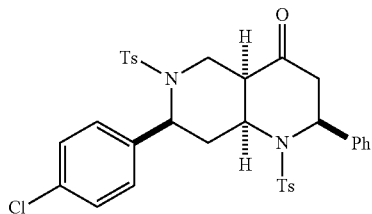

90% yield; white solid; IR (film) ν$_{max}$ 3062, 2923, 2864, 1713, 1347, 1162, 660 cm$^{-1}$; $^1$H NMR (500 MHz, CDCl$_3$) δ 7.73 (d, J=8.0 Hz, 2H), 7.46 (d, J=8.1 Hz, 2H), 7.37-7.36 (m, 4H), 7.23-7.14 (m, 5H), 7.03 (d, J=8.4 Hz, 2H), 6.75 (d, J=8.4 Hz, 2H), 5.68 (d, J=6.5 Hz, 1H), 4.82 (dd, J=11.2, 6.9 Hz, 1H), 4.56-4.52 (m, 1H), 3.79 (dd, J=15.4, 7.9 Hz, 1H), 3.44 (dd, J=15.3, 9.0 Hz, 1H), 2.93 (d, J=14.8 Hz, 1H), 2.64 (dd, J=17.2, 8.6 Hz, 1H), 2.45 (s, 3H), 2.38 (s, 3H), 2.20 (dd, J=14.8, 7.1 Hz, 1H), 1.74-1.69 (m, 1H), 0.87 (td, J=12.6, 11.8 Hz, 1H); $^{13}$C NMR (125 MHz, CDCl$_3$) δ 206.3, 144.2, 143.5, 139.3, 138.7, 137.3, 136.9, 133.1, 130.3, 129.6, 128.5, 128.3, 128.0, 127.3, 127.2, 127.0, 126.6, 58.0, 55.1, 53.2, 45.3, 41.3, 40.5, 36.4, 21.5, 21.4; MS (MALDI) calcd. for C$_{34}$H$_{33}$ClN$_2$O$_5$S$_2$Na [M+Na]$^+$ 671.14. found 671.33.

2B5

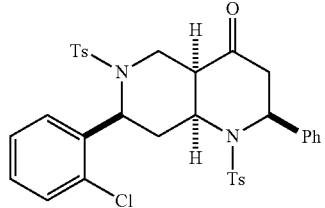

91% yield; white solid; IR (film) ν$_{max}$ 3063, 2946, 2923, 1712, 1349, 1162, 660 cm$^{-1}$; $^1$H NMR (500 MHz, CDCl$_3$)

δ 7.69 (d, J=8.3 Hz, 2H), 7.57 (d, J=8.2 Hz, 2H), 7.37 (d, J=5.3 Hz, 2H), 7.30 (d, J=7.8 Hz, 2H), 7.26-7.24 (m, 2H), 7.19-7.09 (m, 4H), 7.06-6.98 (m, 2H), 6.94 (dd, J=7.6, 1.6 Hz, 1H), 5.68 (d, J=6.2 Hz, 1H), 5.10 (dd, J=11.6, 6.3 Hz, 1H), 4.42-4.38 (m, 1H), 4.06 (dd, J=15.6, 7.9 Hz, 1H), 3.55 (dd, J=15.6, 9.6 Hz, 1H), 2.93 (dd, J=14.9, 2.2 Hz, 1H), 2.69 (dd, J=17.8, 9.1 Hz, 1H), 2.47 (s, 3H), 2.40 (s, 3H), 2.26 (dd, J=14.6, 7.1 Hz, 1H), 1.86-1.82 (m, 1H), 0.74 (td, J=12.6, 11.8 Hz, 1H); $^{13}$C NMR (125 MHz, CDCl$_3$) δ 206.5, 144.2, 143.6, 139.1, 138.4, 137.3, 136.5, 131.1, 130.2, 129.6, 129.5, 128.5, 128.4, 128.2, 128.0, 127.2, 127.1, 126.9, 126.7, 56.6, 54.9, 53.2, 45.3, 41.6, 41.4, 34.8, 21.5, 21.4; MS (MALDI) calcd. for C$_{34}$H$_{33}$ClN$_2$O$_5$S$_2$Na [M+Na]$^+$ 671.14. found 671.72.

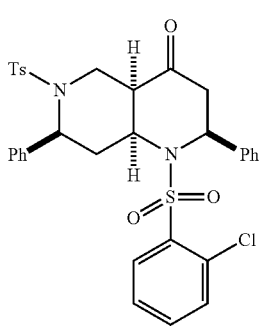

G3

88% yield; white solid; IR (film) ν$_{max}$ 3063, 2917, 1713, 1348, 1164, 662 cm$^{-1}$; $^1$H NMR (500 MHz, CDCl$_3$) δ 8.28 (dd, J=7.8, 1.4 Hz, 1H), 77.63-7.58 (m, 2H), 7.53-7.50 (m, 1H), 7.40 (d, J=7.7 Hz, 2H), 7.36 (d, J=8.2 Hz, 2H), 7.22 (t, J=7.5 Hz, 2H), 7.18-7.06 (m, 6H), 6.84 (d, J=6.8 Hz, 2H), 5.72 (d, J=5.4 Hz, 1H), 4.88 (dd, J=11.4, 6.8 Hz, 1H), 3.84 (dd, J=15.2, 7.9 Hz, 1H), 3.45 (dd, J=15.3, 9.2 Hz, 1H), 3.07 (dd, J=15.0, 2.0 Hz, 1H), 2.92 (dd, J=17.5, 8.8 Hz, 1H), 2.76 (dd, J=14.8, 7.0 Hz, 1H), 2.35 (s, 3H), 1.92-1.88 (m, 1H), 1.04 (td, J=13.5, 11.8 Hz, 1H); $^{13}$C NMR (125 MHz, CDCl$_3$) δ 206.8, 143.2, 140.2, 139.3, 136.9, 136.7, 134.2, 132.8, 132.3, 131.2, 129.4, 128.6, 128.2, 128.1, 127.6, 127.5, 127.3, 126.9, 125.9, 58.4, 55.2, 53.1, 46.1, 42.5, 40.8, 36.2, 21.4; MS (MALDI) calcd. for C$_{33}$H$_{31}$ClN$_2$O$_5$S$_2$Na [M+Na]$^+$ 657.12. found 657.43.

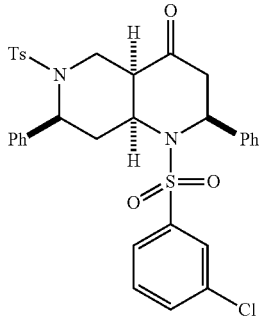

G4

85% yield; white solid; IR (film) ν$_{max}$ 3064, 2921, 1713, 1348, 1165, 668 cm$^{-1}$; $^1$H NMR (500 MHz, CDCl$_3$) δ 7.92 (t, J=1.8 Hz, 1H), 7.80 (d, J=8.8 Hz, 1H), 7.64-7.62 (m, 1H), 7.55 (t, J=7.9 Hz, 1H), 7.46 (d, J=8.2 Hz, 2H), 7.37 (d, J=7.9 Hz, 2H), 7.23 (t, J=7.5 Hz, 2H), 7.19-7.16 (m, 3H), 7.13-7.08 (m, 3H), 6.85-6.83 (m, 2H), 5.72 (d, J=6.5 Hz, 1H), 4.93 (dd, J=11.1, 7.1 Hz, 1H), 4.59 (t, J=10.4 Hz, 1H), 3.80 (dd, J=15.4, 8.1 Hz, 1H), 3.45 (dd, J=15.5, 9.1 Hz, 1H), 3.01 (dd, J=14.9, 2.0 Hz, 1H), 2.74 (dd, J=17.5, 8.7 Hz, 1H), 2.36 (s, 3H), 2.31 (dd, J=14.9, 7.1 Hz, 1H), 1.80-1.75 (m, 1H), 0.99 (td, J=13.5, 11.7 Hz, 1H); $^{13}$C NMR (125 MHz, CDCl$_3$) δ 206.0, 143.4, 142.0, 140.0, 139.0, 136.8, 135.9, 133.4, 131.0, 129.5, 128.6, 128.2, 128.1, 127.4, 127.3, 127.1, 126.6, 125.8, 124.8, 58.2, 55.4, 53.4, 45.6, 41.7, 40.4, 36.1, 21.4; MS (MALDI) calcd. for C$_{33}$H$_{31}$ClN$_2$O$_5$S$_2$Na [M+Na]$^+$ 657.12. found 657.38.

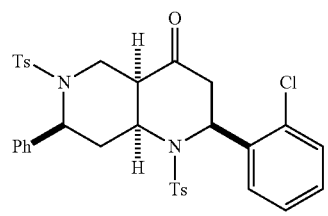

G5

80% yield; white solid; IR (film) ν$_{max}$ 3063, 2923, 1725, 1351, 1165, 658 cm$^{-1}$; $^1$H NMR (500 MHz, CDCl$_3$) δ 7.73 (d, J=8.3 Hz, 2H), 7.41-7.31 (m, 6H), 7.21-7.12 (m, 7H), 7.00 (d, J=7.1 Hz, 2H), 5.54 (dd, J=10.1, 5.7 Hz, 1H), 4.71 (dd, J=11.2, 5.6 Hz, 1H), 4.51-4.46 (m, 1H), 3.85 (dd, J=14.2, 7.2 Hz, 1H), 3.54 (dd, J=14.1, 6.6 Hz, 1H), 2.88 (dd, J=16.8, 5.7 Hz, 1H), 2.65 (dd, J=16.8, 10.2 Hz, 1H), 2.53 (dd, J=14.4, 7.1 Hz, 1H), 2.46 (s, 3H), 2.42-2.38 (m, 4H), 1.86 (td, J=13.3, 11.4 Hz, 1H); $^{13}$C NMR (125 MHz, CDCl$_3$) δ 205.1, 144.5, 143.3, 139.64, 139.62, 136.7, 131.7, 130.1, 129.9, 129.3, 128.8, 128.2, 127.6, 127.5, 127.4, 127.3, 127.2, 126.8, 60.0, 54.6, 53.1, 45.5, 43.8, 43.2, 39.5, 21.5, 21.4; MS (MALDI) calcd. for C$_{34}$H$_{33}$ClN$_2$O$_5$S$_2$Na [M+Na]$^+$ 671.14. found 671.53.

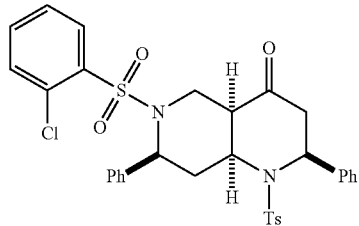

G7

87% yield; white solid; IR (film) ν$_{max}$ 3063, 2921, 1714, 1336, 1163, 661 cm$^{-1}$; $^1$H NMR (500 MHz, CDCl$_3$) δ 7.90 (d, J=8.2 Hz, 2H), 7.73 (d, J=7.5 Hz, 1H), 7.42-7.40 (m, 4H), 7.28-7.22 (m, 4H), 7.17-7.11 (m, 2H), 6.99-6.92 (m, 3H), 6.73 (d, J=6.9 Hz, 2H), 5.80 (d, J=6.5 Hz, 1H), 4.84 (dd, J=11.1, 6.9 Hz, 1H), 4.80-4.75 (m, 1H), 4.17 (dd, J=15.3, 8.0 Hz, 1H), 3.68 (dd, J=15.4, 9.1 Hz, 1H), 3.02 (dd, J=14.9, 2.1 Hz, 1H), 2.69 (dd, J=17.4, 8.8 Hz, 1H), 2.48 (s, 3H), 2.38 (dd, J=14.7, 7.1 Hz, 1H), 1.80-1.75 (m, 4H), 1.05 (td, J=13.5, 11.6 Hz, 1H); $^{13}$C NMR (125 MHz, CDCl$_3$) δ 206.2, 144.2, 139.6, 139.0, 137.6, 137.3, 133.2, 131.8, 131.4, 130.4, 128.5, 128.0, 127.9, 127.4, 127.3, 126.7, 126.6, 125.6, 59.0, 55.3, 53.3, 46.2, 41.6, 36.3, 21.5; MS (MALDI) calcd. for $C_{33}H_{31}ClN_2O_5S_2Na$ [M+Na]⁺ 657.12. found 657.62.

G8

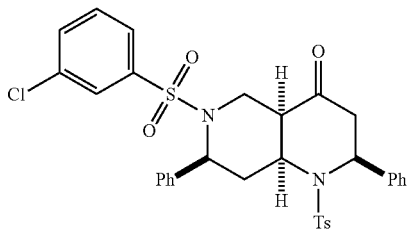

84% yield; white solid; IR (film) $v_{max}$ 3063, 2917, 1713, 1349, 1163, 660 cm⁻¹; ¹H NMR (500 MHz, CDCl₃) δ 7.84 (d, J=8.2 Hz, 2H), 7.42-7.39 (m, 5H), 7.34 (d, J=7.9 Hz, 1H), 7.30 (s, 1H), 7.24-7.21 (m, 3H), 7.17-7.11 (m, 2H), 7.06 (t, J=7.5 Hz, 2H), 6.78 (d, J=7.4 Hz, 2H), 5.77 (d, J=6.5 Hz, 1H), 4.84 (dd, J=11.4, 6.7 Hz, 1H), 4.65 (t, J=10.1 Hz, 1H), 3.81 (dd, J=15.0, 7.8 Hz, 1H), 3.56 (dd, J=15.0, 8.9 Hz, 1H), 3.01 (dd, J=14.9, 1.7 Hz, 1H), 2.74 (dd, J=17.1, 8.5 Hz, 1H), 2.49 (s, 3H), 2.34 (dd, J=15.3, 6.5 Hz, 1H), 1.75-1.71 (m, 1H), 1.03 (td, J=13.5, 11.9 Hz, 1H); ¹³C NMR (125 MHz, CDCl₃) δ 206.3, 144.3, 141.8, 139.4, 139.0, 137.3, 134.8, 132.3, 130.4, 130.0, 128.5, 128.2, 128.0, 127.9, 127.3, 126.9, 126.7, 126.2, 124.8, 59.2, 55.2, 53.4, 45.8, 41.5, 40.9, 36.4, 21.5; MS (MALDI) calcd. for $C_{33}H_{31}ClN_2O_5S_2Na$ [M+Na]⁺ 657.12. found 657.48.

G10

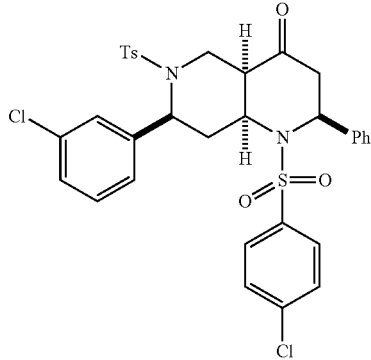

83% yield; white solid; IR (film) $v_{max}$ 3060, 2918, 1717, 1349, 1164, 661 cm⁻¹; ¹H NMR (500 MHz, CDCl₃) δ 7.87 (d, J=8.4 Hz, 2H), 7.87 (d, J=8.4 Hz, 2H), 7.58 (d, J=8.4 Hz, 2H), 7.47 (d, J=8.1 Hz, 2H), 7.38 (d, J=7.6 Hz, 2H), 7.27-7.24 (m, 2H), 7.21-7.19 (m, 3H), 7.08-7.02 (m, 2H), 6.74 (d, J=7.4 Hz, 1H), 6.63 (s, 1H), 5.75 (d, J=6.6 Hz, 1H), 4.85 (dd, J=11.2, 7.0 Hz, 1H), 4.59 (t, J=10.2 Hz, 1H), 3.77 (dd, J=15.4, 7.9 Hz, 1H), 3.43 (dd, J=15.4, 8.9 Hz, 1H), 3.02 (dd, J=14.9, 1.5 Hz, 1H), 2.71 (dd, J=17.2, 8.6 Hz, 1H), 2.39 (s, 3H), 2.32 (dd, J=14.8, 7.1 Hz, 1H), 1.76-1.71 (m, 1H), 0.89 (td, J=13.4, 11.5 Hz, 1H); ¹³C NMR (125 MHz, CDCl₃) δ 205.8, 143.7, 141.8, 139.8, 139.1, 138.8, 136.6, 134.1, 130.0, 129.5, 128.6, 128.2, 128.1, 127.5, 127.3, 127.1, 125.9, 124.2, 57.7, 55.3, 53.3, 45.5, 41.6, 40.5, 36.0, 21.4; MS (MALDI) calcd. for $C_{33}H_{30}Cl_2N_2O_5S_2Na$ [M+Na]⁺ 691.09. found 691.46.

G11

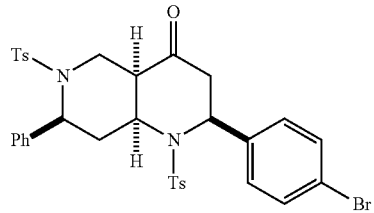

85% yield; white solid; IR (film) $v_{max}$ 3060, 2921, 1714, 1347, 1163, 660 cm⁻¹; ¹H NMR (500 MHz, CDCl₃) δ 7.77 (d, J=8.2 Hz, 2H), 7.44 (d, J=8.2 Hz, 2H), 7.40-7.34 (m, 4H), 7.27 (d, J=7.4 Hz, 2H), 7.18-7.11 (m, 5H), 6.86-6.85 (m, 2H), 5.64 (d, J=6.6 Hz, 1H), 4.95 (dd, J=11.1, 7.0 Hz, 1H), 4.64 (t, J=10.3 Hz, 1H), 3.76 (dd, J=15.4, 8.0 Hz, 1H), 3.46 (dd, J=15.4, 9.1 Hz, 1H), 2.89 (dd, J=14.7, 1.9 Hz, 1H), 2.69 (dd, J=17.4, 8.6 Hz, 1H), 2.49 (s, 3H), 2.38 (s, 3H), 2.32 (dd, J=14.7, 7.1 Hz, 1H), 1.83-1.79 (m, 1H), 0.99 (td, J=13.5, 11.6 Hz, 1H); ¹³C NMR (125 MHz, CDCl₃) δ 206.2, 144.3, 143.3, 139.9, 138.5, 137.1, 137.0, 131.6, 130.3, 129.4, 129.0, 128.3, 127.4, 127.1, 126.6, 125.8, 122.2, 58.4, 54.9, 53.5, 45.6, 41.3, 40.3, 36.5, 21.5, 21.4; MS (MALDI) calcd. for $C_{34}H_{34}BrN_2O_5S_2Na$ [M+Na]⁺ 695.11. found 695.44.

H2

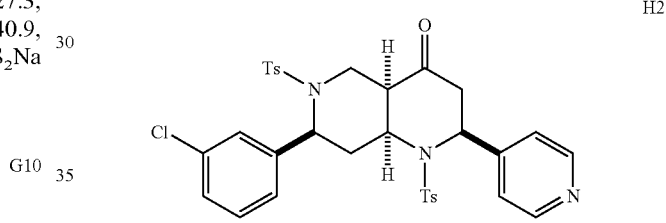

87% yield; white solid; IR (film) $v_{max}$ 3061, 2923, 1715, 1349, 1162, 660 cm⁻¹; ¹H NMR (500 MHz, CDCl₃) δ 8.48 (d, J=5.6 Hz, 2H), 7.77 (d, J=8.2 Hz, 2H), 7.45-7.31 (m, 6H), 7.19-7.14 (m, 2H), 7.06-7.00 (m, 2H), 6.71-6.67 (m, 2H), 5.63 (d, J=6.2 Hz, 1H), 4.87 (dd, J=11.0, 6.9 Hz, 1H), 4.62 (t, J=10.2 Hz, 1H), 3.77 (dd, J=15.3, 7.9 Hz, 1H), 3.47 (dd, J=15.3, 8.8 Hz, 1H), 2.91 (dd, J=14.7, 2.0 Hz, 1H), 2.68 (dd, J=16.9, 8.5 Hz, 1H), 2.46 (s, 3H), 2.36 (s, 3H), 2.29-2.24 (m, 1H), 1.84-1.81 (m, 1H), 0.87 (td, J=13.3, 12.4 Hz, 1H); ¹³C NMR (125 MHz, CDCl₃) δ 205.3, 150.2, 148.5, 143.7, 141.7, 136.7, 136.6, 134.2, 130.5, 129.7, 129.6, 127.6, 127.0, 126.6, 125.8, 123.8, 122.1, 58.0, 54.7, 53.8, 45.5, 40.7, 40.4, 36.8, 21.6, 21.4; MS (MALDI) calcd. for $C_{33}H_{32}ClN_3O_5S_2Na$ [M+Na]⁺ 672.14. found 673.50.

D10

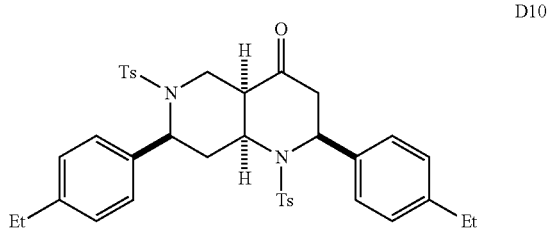 [SMILES: CCc1ccc([C@@H]2C[C@H]3[C@@H](CN2S(=O)(=O)c2ccc(C)cc2)C(=O)C[C@@H](c2ccc(CC)cc2)N3S(=O)(=O)c2ccc(C)cc2)cc1]

88% yield; white solid; IR (film) $v_{max}$ 2965, 2930, 1713, 1347, 1162, 660 cm⁻¹; ¹H NMR (500 MHz, CDCl₃) δ 7.76 (d, J=8.3 Hz, 2H), 7.42 (d, J=8.3 Hz, 2H), 7.37 (d, J=8.0 Hz, 2H), 7.27 (d, J=8.0 Hz, 2H), 7.16 (d, J=8.0 Hz, 2H), 7.05 (d, J=8.2 Hz, 2H), 6.89 (d, J=8.1 Hz, 2H), 6.73 (d, J=8.1 Hz, 2H), 5.69 (d, J=6.5 Hz, 1H), 4.85 (dd, J=11.3, 6.9 Hz, 1H), 4.56 (t, J=10.5 Hz, 1H), 3.78 (dd, J=15.3, 8.0 Hz, 1H), 3.41 (dd, J=15.3, 9.2 Hz, 1H), 2.93 (dd, J=14.9, 2.0 Hz, 1H), 2.668 (dd, J=17.5, 8.9 Hz, 1H), 2.55-2.50 (m, 4H), 2.48 (s, 3H), 2.37 (s, 3H), 2.23 (dd, J=14.8, 7.1 Hz, 1H), 1.74-1.69 (m, 1H), 1.15 (t, J=7.0 Hz, 3H), 1.07 (t, J=7.0 Hz, 1H), 0.94 (td, J=13.6, 11.6 Hz, 1H); $^{13}$C NMR (125 MHz, CDCl$_3$) δ 206.7, 144.3, 144.1, 143.4, 143.0, 137.5, 137.3, 137.2, 136.6, 130.2, 129.4, 128.0, 127.5, 127.4, 127.0, 126.6, 126.0, 58.3, 54.9, 53.1, 45.4, 41.5, 40.5, 36.3, 28.3, 21.5, 21.4, 15.5, 14.4; MS (MALDI) calcd. for C$_{38}$H$_{42}$N$_2$O$_5$S$_2$Na [M+Na]$^+$ 693.24. found 693.77.

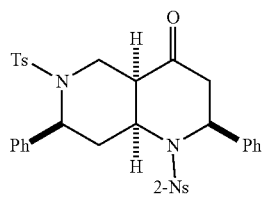

2A6

81% yield; white solid; IR (film) $v_{max}$ 3064, 2921, 1714, 1544, 1373, 1165, 699 cm$^{-1}$; $^1$H NMR (500 MHz, CDCl$_3$) δ 8.30-8.28 (m, 1H), 7.84-7.79 (m, 2H), 7.77-7.74 (m, 1H), 7.41-7.37 (m, 4H), 7.24 (t, J=7.5 Hz, 2H), 7.18 (t, J=7.2 Hz, 1H), 7.13-7.07 (m, 5H), 6.81 (d, J=7.1 Hz, 2H), 5.86 (d, J=6.4 Hz, 1H), 4.99 (dd, J=11.1, 7.1 Hz, 1H), 4.60 (t, J=10.3 Hz, 1H), 3.79 (dd, J=15.3, 8.1 Hz, 1H), 3.46 (dd, J=15.4, 9.1 Hz, 1H), 3.18 (dd, J=15.1, 2.0 Hz, 1H), 3.03 (dd, J=15.1, 7.1 Hz, 1H), 2.93 (dd, J=17.4, 8.7 Hz, 1H), 2.38 (s, 3H), 1.95-1.91 (m, 1H), 1.03 (td, J=13.2, 11.3 Hz, 1H); $^{13}$C NMR (125 MHz, CDCl$_3$) δ 206.8, 147.6, 143.4, 140.0, 139.3, 136.5, 134.2, 132.9, 132.5, 131.8, 129.4, 128.6, 128.2, 128.1, 127.4, 127.3, 127.1, 125.8, 124.5, 58.1, 55.9, 53.5, 46.2, 42.6, 40.6, 35.5, 21.4; MS (MALDI) calcd. for C$_{33}$H$_{31}$N$_3$O$_7$S$_2$Na [M+Na]$^+$ 668.15. found 668.42.

Procedure for the Synthesis of Naphthyridine Enol Ether 15'

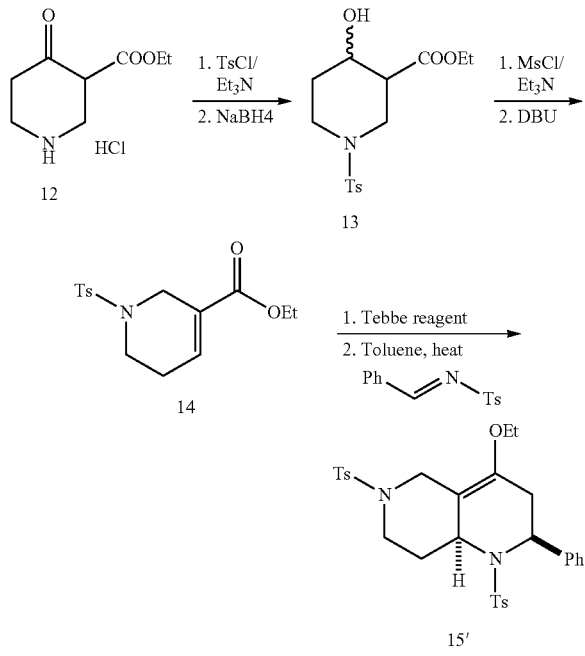

To a solution of ethyl 4-piperidone-3-carboxylate hydrochloride (2.0 g, 9.6 mmol) in DCM (40 mL) was added dropwise at 0° C. Et$_3$N (5.3 mL, 4.0 eq.). After 30 mins, a solution of TsCl in DCM (20 mL) was added dropwise to the mixture. After stirring over night at room temperature, the reaction mixture was washed by 2 N HCl (3×30 mL), saturated NaHCO$_3$ (2×30 mL), and brine (2×30 mL). The organic phase was dried over anhydrous Na$_2$SO$_4$ and concentrated. The crude residue was used for the next step without any purification. To a stirred solution of the crude residue (~9.6 mmol) in absolute ethanol (15 ml) was added dropwise at 0° C. a solution of NaBH$_4$ (363 mg, 9.6 mmol) in absolute ethanol (15 mL). Stirring was continued for an additional 13 h, during which the reaction temperature rose slowly to room temperature. A few drops of aqueous acetic acids followed by water were added to the reaction mixture which was then extracted with DCM (3×30 mL). The organic phase was dried over anhydrous Na$_2$SO$_4$ and concentrated. The crude residue was purified by flash column chromatography on the silica gel using 33% ethyl acetate in hexanes to afford the product alcohol in 54% yield, two steps. To a stirred solution of the alcohol (1.7 g, 5.2 mmol) and Et$_3$N (2.2 mL, 3.0 eq.) in ether (12 mL) was added dropwise at 0° C. methanesulfonyl chloride (0.8 mL). The reaction was stirred for 3 h after which a solution of DBU (1.5 mL) in ether (6 mL) was added to it. Stirring was continued for an additional 4 h after which the reaction mixture was quenched by the addition of water, and then extracted with ether (3×30 mL). The organic phase was dried over anhydrous Na$_2$SO$_4$ and concentrated. The crude residue was purified by flash column chromatography on the silica gel using 20% ethyl acetate in hexanes to afford the product α,β-unsaturated ester in 70% yield, two steps (Kosugi, H., et al., J. Chem. Soc. Perkin Trans. 217-221 (1998)). Naphthyridine enol ether (15') was synthesized following the same procedure of naphthyridine enol ethers (11') synthesis from the α,β-unsaturated ester as white solid in 53% yield, two steps. IR (film) $v_{max}$ 3060, 2978, 2921, 1699, 1343, 1165, 655 cm$^{-1}$; $^1$H NMR (500 MHz, CDCl$_3$) δ 7.67 (d, J=7.9 Hz, 2H), 7.60 (d, J=8.2 Hz, 2H), 7.42 (d, J=7.6 Hz, 2H), 7.34-7.26 (m, 7H), 5.31 (d, J=6.6 Hz, 1H), 4.86 (dd, J=12.1, 2.0 Hz, 1H), 4.02 (d, J=11.8 Hz, 1H), 3.82 (dq, J=9.5, 7.1 Hz, 1H), 3.74 (dq, J=9.5, 7.1 Hz, 1H), 3.53 (d, J=12.0 Hz, 1H), 2.60 (d, J=17.1 Hz, 1H), 2.47-2.44 (m, 4H), 2.41 (s, 3H), 2.23 (td, J=12.2, 2.3 Hz, 1H), 2.09-2.04 (m, 1H), 1.67-1.63 (m, 1H), 1.19 (t, J=7.1 Hz, 3H), 0.96 (ddd, J=24.8, 12.4, 4.4 Hz, 1H); $^{13}$C NMR (125 MHz, CDCl$_3$) δ 144.1, 143.5, 139.6, 137.5, 132.8, 129.8, 129.5, 128.4, 127.7, 127.6, 126.5, 110.0, 63.9, 53.9, 52.4, 46.1, 44.6, 32.7, 24.6, 21.5, 21.4, 15.0; MS (MALDI) calcd. for C$_{30}$H$_{34}$N$_2$O$_5$S$_2$Na [M+Na]$^+$ 589.18. found 589.60.

H6

Naphthyridinone (H6) was synthesized following the same procedure of naphthyridinone (11) synthesis from naphthyridine enol ether (15') in 87% yield; white solid; IR (film) $v_{max}$ 3059, 2922, 2843, 1725, 1338, 1165, 656 cm$^{-1}$;

$^1$H NMR (500 MHz, CDCl$_3$) δ 7.73 (d, J=8.3 Hz, 2H), 7.58 (d, J=8.2 Hz, 2H), 7.39 (d, J=7.5 Hz, 2H), 7.32-7.29 (m, 6H), 7.27-7.26 (m, 1H), 5.61 (dd, J=7.1, 3.9 Hz, 1H), 4.37-4.33 (m, 1H), 4.27 (d, J=12.0 Hz, 1H), 3.53-3.51 (m, 1H), 3.01 (dd, J=15.5, 4.0 Hz, 1H), 2.51 (dd, J=15.5, 7.4 Hz, 1H), 2.43 (s, 6H), 2.29-2.26 (m, 1H), 2.13-2.08 (m, 2H), 1.49-1.47 (m, 1H), 1.32-1.24 (m, 1H); $^{13}$C NMR (125 MHz, CDCl$_3$) δ 202.7, 144.2, 143.6, 140.7, 137.0, 132.8, 130.2, 129.5, 128.6, 127.7, 127.6, 126.9, 126.7, 56.2, 55.6, 46.4, 45.7, 43.5, 42.2, 31.0, 21.5, 21.4; MS (MALDI) calcd. For C$_{28}$H$_{30}$N$_2$O$_5$S$_2$Na [M+Na]$^+$561.15. found 561.77.

Synthesis of Compounds 2B6 and 2B7

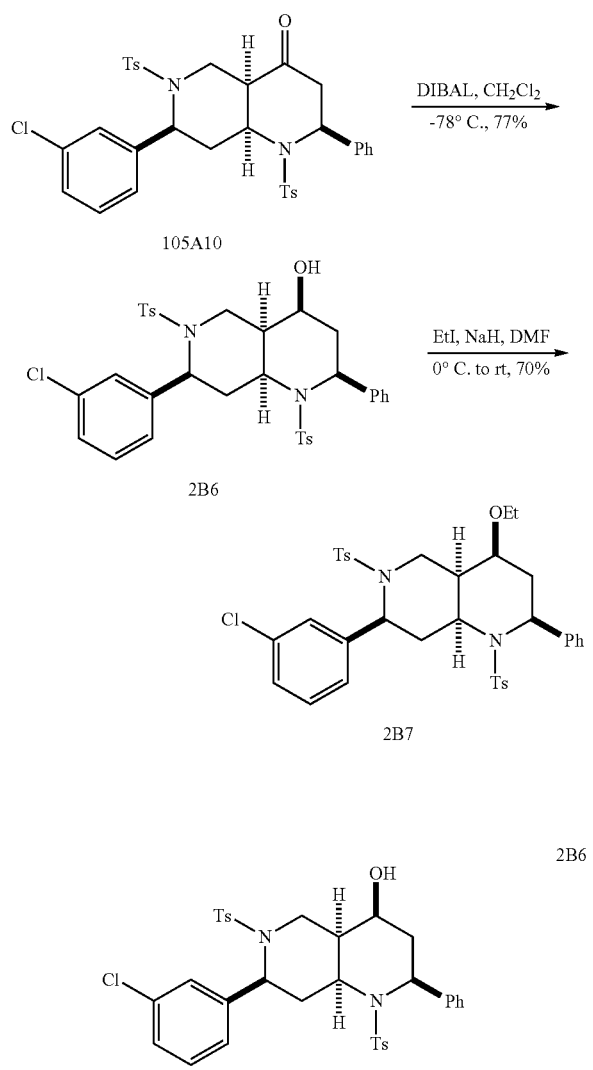

To a solution of naphthyridinone (105A10, 0.22 mmol) in CH$_2$Cl$_2$ (6 mL) at −78° C., 0.55 mL diisobutylaluminium hydride (DIBAL, 1.0 M in CH$_2$Cl$_2$) was added dropwise. The reaction was finished in an hour. Water (0.03 mL) was added at −78° C. and the reaction was warmed up to room temperature. Anhydrous Na$_2$SO$_4$ (0.1 g) was added. The reaction mixture was filtered through the Celite pad and the filtrate was concentrated. The crude residue was purified by flash column chromatography on the silica gel using 33% ethyl acetate in hexanes to afford the product (2B6) as a white solid in 77% yield; IR (film) ν$_{max}$ 3516, 3061, 2954, 2925, 1598, 1344, 1161, 667 cm$^{-1}$; $^1$H NMR (500 MHz, CDCl$_3$) δ 7.63 (d, J=8.2 Hz, 2H), 7.43 (d, J=8.3 Hz, 2H), 7.36 (d, J=7.8 Hz, 2H), 7.31-7.24 (m, 4H), 7.19-7.16 (m, 3H), 7.13-7.10 (m, 2H), 7.00-6.97 (m, 1H), 6.88 (s, 1H), 5.07 (t, J=7.9 Hz, 1H), 4.83 (dd, J=11.9, 6.0 Hz, 1H), 4.29-4.24 (m, 1H), 3.83 (dd, J=14.7, 6.7 Hz, 1H), 3.47 (dd, J=14.8, 10.8 Hz, 1H), 3.43-3.39 (m, 1H), 2.46 (s, 3H), 2.40 (s, 3H), 2.33-2.24 (m, 2H), 2.17-2.10 (m, 1H), 2.00-1.90 (m, 2H), 1.67 (d, J=3.6 Hz, 1H); $^{13}$C NMR (125 MHz, CDCl$_3$) δ 143.8, 143.5, 143.2, 142.5, 137.0, 136.6, 134.2, 129.9, 129.7, 129.5, 128.3, 127.5, 126.9, 126.8, 126.7, 126.0, 125.6, 124.3, 65.6, 58.6, 56.0, 50.8, 41.6, 38.8, 35.8, 33.3, 21.5, 21.4; MS (MALDI) calcd. for C$_{34}$H$_{35}$ClN$_2$O$_5$S$_2$Na [M+Na]$^+$ 673.16. found 673.79.

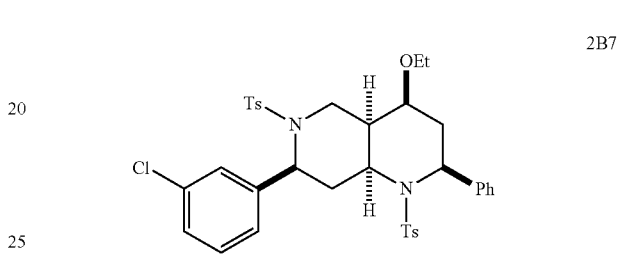

To a solution of 2B7 (0.16 mmol) and NaH (60% in mineral oil, 0.24 mmol) in anhydrous DMF (2.5 mL), ethyl iodide (0.24 mmol) was added dropwise at 0° C. and the reaction was warmed up to room temperature. The mixture was stirred at 50° C. for 5 hours. The saturated NaCl (2.0 mL) was added and the mixture was extracted by ethyl acetate (3×10 mL). The organic phase was dried over anhydrous Na$_2$SO$_4$ and concentrated. The crude residue was purified by flash column chromatography on the silica gel using 20% ethyl acetate in hexanes to afford final product 2B7 as yellow oil in 70% yield; IR (film) ν$_{max}$ 3061, 2971, 1598, 1345, 1161, 665 cm$^{-1}$; $^1$H NMR (500 MHz, CDCl$_3$) δ 7.62 (d, J=8.2 Hz, 2H), 7.46 (d, J=8.3 Hz, 2H), 7.34-7.30 (m, 4H), 7.27-7.24 (m, 2H), 7.21-7.15 (m, 3H), 7.00-6.97 (m, 1H), 7.12-7.10 (m, 2H), 7.01-6.98 (m, 1H), 6.93 (s, 1H), 5.01-4.93 (m, 2H), 4.32-4.27 (m, 1H), 3.81 (dd, J=15.0, 7.0 Hz, 1H), 3.30 (dd, J=15.0, 11.8 Hz, 1H), 3.19-3.05 (m, 2H), 2.64-2.60 (m, 1H), 2.47 (s, 3H), 2.44-2.40 (m, 4H), 2.29-2.25 (m, 1H), 2.11-2.04 (m, 1H), 1.94-1.83 (m, 2H), 0.96 (t, J=7.0 Hz, 3H). $^{13}$C NMR (125 MHz, CDCl$_3$) δ 143.7, 143.4, 143.3, 142.5, 137.5, 136.8, 134.2, 129.8, 129.7, 129.4, 128.2, 127.4, 126.8, 125.8, 125.4, 124.2, 72.3, 64.2, 58.0, 56.6, 50.7, 40.5, 38.4, 34.6, 30.4, 21.5, 21.4, 14.8; MS (MALDI) calcd. for C$_{36}$H$_{39}$ClN$_2$O$_5$S$_2$Na [M+Na]$^+$701.19. found 701.75.

Synthesis of Compound G9

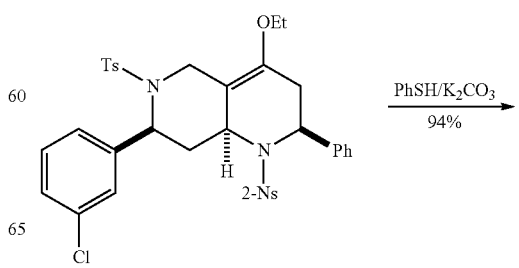

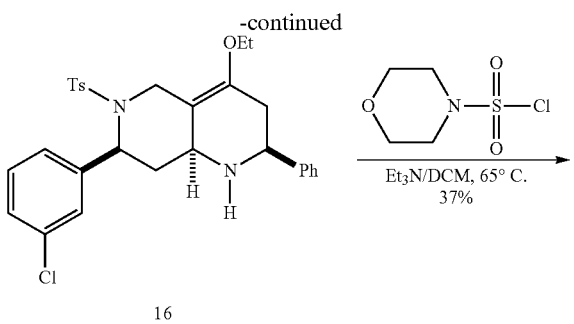

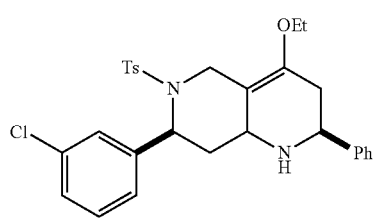

To a mixture of naphthyridine enol ether (0.10 mmol) and K$_2$CO$_3$ (0.30 mmol) in anhydrous CH$_3$CN (2.5 mL), PhSH (0.12 mmol) was added dropwise at room temperature. The mixture was stirred at 50° C. for 8 hours. The saturated NaCl (2.0 mL) was added and the mixture was extracted by ethyl acetate (3×10 mL). The organic phase was dried over anhydrous Na$_2$SO$_4$ and concentrated. The crude residue was purified by flash column chromatography on the silica gel using 1% triethylamine and 80% ethyl acetate in hexanes to afford final product 16 as white solid in 94% yield; IR (film) ν$_{max}$ 3400, 3062, 2977, 1597, 1346, 1161, 701 cm$^{-1}$; $^1$H NMR (500 MHz, CDCl$_3$) δ 7.62 (d, J=8.3 Hz, 2H), 7.34-7.16 (m, 11H), 4.86 (dd, J=10.8, 6.9 Hz, 1H), 4.71 (d, J=17.2 Hz, 1H), 4.14 (dt, J=17.2, 1.4 Hz, 1H), 3.84-3.71 (m, 2H), 3.56 (dd, J=10.5, 4.4 Hz, 1H), 2.91 (d, J=11.3 Hz, 1H), 2.43 (s, 3H), 2.30 (d, J=14.8 Hz, 1H), 2.25-2.14 (m, 2H), 1.70 (td, J=12.1, 11.5 Hz, 1H), 1.57 (br, 1H), 1.26 (t, J=7.0 Hz, 3H); $^{13}$C NMR (125 MHz, CDCl$_3$) δ 145.4, 144.2, 143.3, 143.2, 136.6, 134.1, 129.6, 129.3, 128.6, 127.5, 127.3, 127.2, 126.3, 126.2, 124.4, 111.7, 62.8, 58.3, 56.9, 51.9, 41.4, 37.6, 34.0, 21.4, 15.5; MS (MALDI) calcd. for C$_{29}$H$_{31}$ClN$_2$O$_3$SNa [M+Na]$^+$ 545.16. found 545.79.

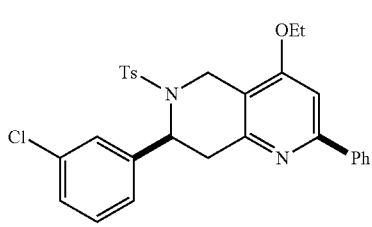

To a solution of 16 (0.10 mmol) and triethylamine (0.30 mmol) in anhydrous CH$_2$Cl$_2$ (2.5 mL), the sulfonyl chloride (0.12 mmol) was added dropwise at room temperature. The mixture was stirred at 65° C. for 12 hours. The saturated NaCl (2.0 mL) was added and the mixture was extracted by ethyl acetate (3×10 mL). The organic phase was dried over anhydrous Na$_2$SO$_4$ and concentrated. The crude residue was purified by flash column chromatography on the silica gel using 50% ethyl acetate in hexanes to afford final product G9 as white solid in 37% yield; IR (film) ν$_{max}$ 3061, 2982, 2932, 1589, 1346, 1160, 663 cm$^{-1}$; $^1$H NMR (500 MHz, CDCl$_3$) δ 7.90-7.88 (m, 2H), 7.71 (d, J=8.3 Hz, 2H), 7.46-7.43 (m, 2H), 7.41-7.37 (m, 1H), 7.26 (s, 1H), 7.21 (d, J=8.0 Hz, 2H), 7.18-7.12 (m, 3H), 6.96 (s, 1H), 5.53 (d, J=5.9 Hz, 1H), 4.93 (d, J=18.0 Hz, 1H), 4.16-4.07 (m, 2H), 3.94 (d, J=18.0 Hz, 1H), 3.34 (dd, J=17.2, 0.7 Hz, 1H), 3.14 (dd, J=17.3, 6.5 Hz, 1H), 2.35 (s, 3H), 1.44 (t, J=7.0 Hz, 3H); $^{13}$C NMR (125 MHz, CDCl$_3$) δ 161.6, 157.8, 152.5, 143.5, 140.6, 139.5, 137.3, 134.4, 129.7, 128.9, 128.6, 127.7, 127.6, 126.8, 126.7, 125.3, 114.6, 101.6, 63.8, 53.7, 38.5, 33.4, 21.4, 14.4; MS (MALDI) calcd. for C$_{29}$H$_{27}$ClN$_2$O$_3$SNa [M+Na]$^+$ 541.13. found 542.64.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

REFERENCES

1. Schreiber S L, Kapoor, T M, Wess G, Eds. (2008) *Chemical Biology: From Small Molecules to Systems Biology and Drug Design* (Wiley-VCH, Weinheim, Germany).
2. Schreiber S L (2000) Target-oriented and diversity-oriented organic synthesis in drug discovery. *Science* 287: 1964-1969.
3. Hopkins A L, Groom C R (2002) The druggable genome. *Nat Rev Drug Discov* 1:727-730.
4. Strausberg R L, Schreiber S L (2003) From knowing to controlling: a path from genomics to drugs using small molecule probes. *Science* 300:294-295.
5. Dolle R E, et al. (2010) Comprehensive survey of chemical libraries for drug discovery and chemical biology: 2009. *J Comb Chem* 12:765-806.
6. Terret N K (1998) *Combinatorial Chemistry* (Oxford University Press, Oxford, UK).
7. Burke M D, Schreiber S L (2004) A planning strategy for diversity-oriented synthesis. *Angew Chem Int Ed Engl* 43:46-58.
8. Nielsen T E, Schreiber S L (2008) Towards the optimal screening collection: a synthesis strategy. *Angew Chem Int Ed Engl* 47:48-56.
9. Spandl R J, Bender A, Spring D R (2008) Diversity-oriented synthesis; a spectrum of approaches and results. *Org Biomol Chem* 6:1149-1158.
10. Galloway W R J D, Isidro-Llobet A, Spring D R (2010) Diversity-oriented synthesis as a tool for the discovery of novel biologically active small molecules. *Nat Commun* 1: 80-92.
11. Zhu X F, Lan J, Kwon O (2003) An expedient phosphine-catalyzed [4+2] annulation: synthesis of highly functionalized tetrahydropyridines. *J Am Chem Soc* 125:4716-4717.

12. Lu K, Kwon O (2009) Phosphine-Catalyzed [4+2] Annulation: Synthesis of Ethyl 6-Phenyl-1-Tosyl-1,2,5,6-Tetrahydropyridine-3-Carboxylate. *Org. Synth* 2009:212-224.
13. Xu Z, Lu X (1998) A Novel [3+2] Cycloaddition Approach to Nitrogen Heterocycles via Phosphine-Catalyzed Reactions of 2,3-Butadienoates or 2-Butynoates and Dimethyl Acetylenedicarboxylates with Imines: A Convenient Synthesis of Pentabromopseudilin. *J Org Chem* 63:5031-5041.
14. Zhu X, Henry C E, Kwon O (2005) A highly diastereoselective synthesis of 3-carbethoxy-2,5-disubstituted-3pyrrolines by phosphine catalysis. Tetrahedron 61:6276-6282.
15. Zhu X F, Henry C E, Wang J, Dudding T, Kwon O (2005) Phosphine-catalyzed synthesis of 1,3-dioxan-4-ylidenes. *Org Lett* 7:1387-1390.
16. Zhu X F, Schaffner A P, Li R C, Kwon O (2005) Phosphine-catalyzed synthesis of 6-substituted 2-pyrones: manifestation of E/Z-isomerism in the zwitterionic intermediate. *Org Lett* 7:2977-2980.
17. Creech G S, Kwon O (2008) Alcohol-assisted phosphine catalysis: one-step syntheses of dihydropyrones from aldehydes and allenoates. *Org Lett* 10:429-432.
18. Creech G S, Zhu X, Fonovic B, Dudding T, Kwon O (2008) Theory-Guided Design of Bronsted Acid-Assisted Phosphine Catalysis: Synthesis of Dihydropyrones from Aldehydes and Allenoates. *Tetrahedron* 64:6935-6942.
19. Guo H, Xu Q, Kwon O (2009) Phosphine-promoted [3+3] annulations of aziridines with allenoates: facile entry into highly functionalized tetrahydropyridines. *J Am Chem Soc* 131:6318-6319.
20. Tran Y S, Kwon O (2007) Phosphine-catalyzed [4+2] annulation: synthesis of cyclohexenes. *J Am Chem Soc* 129:12632-12633.
21. Sriramurthy V, Barcan G A, Kwon O (2007) Bisphosphine-catalyzed mixed double-Michael reactions: asymmetric synthesis of oxazolidines, thiazolidines, and pyrrolidines. *J Am Chem Soc* 129:12928-12929.
22. Sriramurthy V, Kwon O (2010) Diphosphine-catalyzed mixed double-Michael reaction: a unified synthesis of indolines, dihydropyrrolopyridines, benzimidazolines, tetrahydroquinolines, tetrahydroisoquinolines, dihydrobenzo-1,4-oxazines, and dihydrobenzo-3,1-oxazines. *Org Lett* 12:1084-1087.
23. Watanabe M, et al. (2008) Inhibitors of protein geranylgeranyltransferase I and Rab geranylgeranyltransferase identified from a library of allenoate-derived compounds. *J Biol Chem* 283:9571-9579.
24. Wang Z, et al. (2011) Diversity Through a Branched Reaction Pathway: Generation of Multicyclic Scaffolds and Identification of Antimigratory Agents. *Chem. Eur J* 17:649-654.
25. Castellano S, et al. (2007) Small-molecule inhibitors of protein geranylgeranyltransferase type I. *J Am Chem Soc* 129:5843-5845.
26. Lu J, et al. (2009) In vivo antitumor effect of a novel inhibitor of protein geranylgeranyltransferase I. *Mol Cancer Ther* 8:1218-1226.
27. Butcher E C, Berg E L, Kunkel E J (2004) Systems biology in drug discovery. *Nat Biotechnol* 22:1253-1259.
28. Berg E L, Kunkel E J, Hytopoulos E, Plavec I (2006) Characterization of compound mechanisms and secondary activities by BioMAP analysis. *J Pharmacol Toxicol Methods* 53:67-74.
29. Nakamoto T, Inagawa H, Takagi K, Soma G (2000) A new method of antitumor therapy with a high dose of TNF perfusion for unresectable liver tumors. *Anticancer Res* 20:4087-4096.
30. Sorensen E W, Gerber S A, Frelinger J G, Lord E M (2010) IL-12 suppresses vascular endothelial growth factor receptor 3 expression on tumor vessels by two distinct IFN-gamma-dependent mechanisms. *J Immunol* 184:1858-1866.
31. Miller C H, Maher S G, Young H A (2009) Clinical Use of Interferon-gamma. *Ann N Y Acad Sci* 1182:69-79.
32. Ghazizadeh R, Shimizu H, Tosa M, Ghazizadeh M (2010) Pathogenic mechanisms shared between psoriasis and cardiovascular disease. *Int J Med Sci* 7:284-289.
33. Rice J W, Davis J E, Crowl R M, Johnston P A (1996) Development of a high volume screen to identify inhibitors of endothelial cell activation. *Anal Biochem* 241:254-259.
34. Zerwes H G, Peter J C, Link M, Gubler H, Scheel G (2002) A multiparameter screening assay to assess the cytokine-induced expression of endothelial cell adhesion molecules. *Anal Biochem* 304:166-173.
35. Ren D C, Du G H, Zhang J T (2003) High throughput screening for intercellular adhesion molecule-1 inhibitor. *Yao Xue Xue Bao* 38:405-408.
36. May M J, Wheeler-Jones C P, Pearson J D (1996) Effects of protein tyrosine kinase inhibitors on cytokine-induced adhesion molecule expression by human umbilical vein endothelial cells. *Br J Pharmacol* 118:1761-1771.
37. Pandey M K, et al. (2010) Design, synthesis and anti-inflammatory evaluation of PEGylated 4-methyl and 4,8-dimethylcoumarins. *Eur J Pharm Sci* 39:134-140.
38. Vergeer M, Stroes E S (2009) The pharmacology and off-target effects of some cholesterol ester transfer protein inhibitors. *Am J Cardiol* 104:32 E-38E.
39. Barter P J, et al. (2007) Effects of torcetrapib in patients at high risk for coronary events. *N Engl J Med* 357:2109-2122.
40. Metcalfe C, Wheeler B W, Gunnell D, Martin R M (2010) International regulatory activity restricting COX-2 inhibitor use and deaths due to gastrointestinal haemorrhage and myocardial infarction. *Pharmacoepidemiol Drug Saf* 19:778-785.
41. Nissen S E, Wolski K (2007) Effect of rosiglitazone on the risk of myocardial infarction and death from cardiovascular causes. *N Engl J Med* 356:2457-2471.
42. Lukacs N W, et al. (1994) Intercellular adhesion molecule-1 mediates the expression of monocyte-derived MIP-1 alpha during monocyte-endothelial cell interactions. *Blood* 83:1174-1178.
43. Ball C P, et al (1998) Chameleon catches in combinatorial chemistry: Tebbe olefination of polymer supported esters and the synthesis of amines, cyclohexanones, enones, methyl ketones and thiazoles. *Chem Commun* 2019-2020.
44. Barrett A M G, Procopiou P A, Voigtmann U (2001) Solid-phase synthesis of isoxazoles using vinyl ethers as chameleon catches. *Org Lett* 3:3165-3168.
45. Fukuyama T, Cheung M, Kan T (1999) N-Carboalkoxy-2-Nitrobenzenesulfonamides: A practical preparation of n-Boc, N-Alloc, and N-Cbz-protected primary amines. *Synlett* 1301-1303.
46. Zhou Y, et al. (2008) Library Synthesis Using 5,6,7,8-Tetrahydro-1,6-naphthyridines as Scaffolds *J Comb Chem* 10:534-540.

47. Eriksson E E, Xie X, Werr J, Thoren P, Lindbom L (2001) Direct viewing of atherosclerosis in vivo: plaque invasion by leukocytes is initiated by the endothelial selectins. *FASEB J* 15:1149-1157.

48. Rossi B, Constantin G (2008) Anti-selectin therapy for the treatment of inflammatory diseases. *Inflamm Allergy Drug Targets* 7:85-93.

49. Laffer C L, Elijovich F. (2010) Inflammation and Therapy for Hypertension. *Curr Hypertens Rep.* 12:233-242.

50. Short K R, Blackett P R, Gardner A W, Copeland K C (2009) Vascular health in children and adolescents: effects of obesity and diabetes. *Vasc Health Risk Manag* 5:973-990.

51. Cocchi F, et al. (1995) Identification of RANTES, MIP-1 alpha, and MIP-1 beta as the major HIV-suppressive factors produced by CD8+ T cells. *Science* 270:1811-1815.

52. Nakashima E, et al. (1996) A candidate for cancer gene therapy: MIP-1 alpha gene transfer to an adenocarcinoma cell line reduced tumorigenicity and induced protective immunity in immunocompetent mice. *Pharm Res* 13:1896-1901.

We claim:

1. A pharmaceutically acceptable pro-inflammatory composition comprising a pharmaceutically acceptable carrier and an effective amount of one or more of octahydro-1,6-naphthyridin-4-one or a pro-inflammatory analog for augmenting innate immune responses in a mammal, wherein the one or more octahydro-1,6-naphthyridin-4-one or pro-inflammatory analog thereof is octahydro-1,6-naphthyridin-4-one, a compound represented by the formula 104A5, 104A7, 104A8, 104B9, 104B10, 104B11, 104C2, 104C3, 104C4, 104C5, 104C6, 104E2, 104E4, 104E6, 104F8, 104F9, 104F11, 104G2, 104H3, 104H4, 104H5, 104H6, 104H7, 104H8, 104H9, 104H10, 104H11, 105A3, 105A6, 105A7, 105A8, 105A9, 105A10, 105A11, 105B2, 105B3, G2, G3, G4, G6, G7, G8, G10, G11, H2, H3, H4, H5, H6, H7, H8, H9, H10, 2A2, 2A3, 2A4, 2A5, 2A6, 2A7, 2A8, 2A9, 2A10, 2A11, 2B3, 2B4, 2B5, 2B6, 2B7,

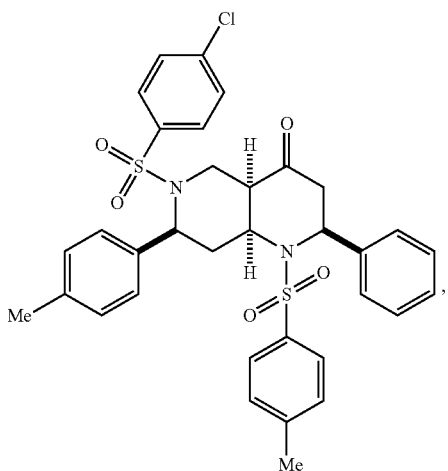

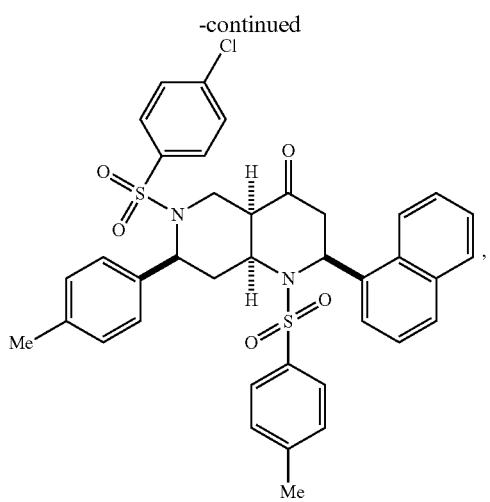

-continued

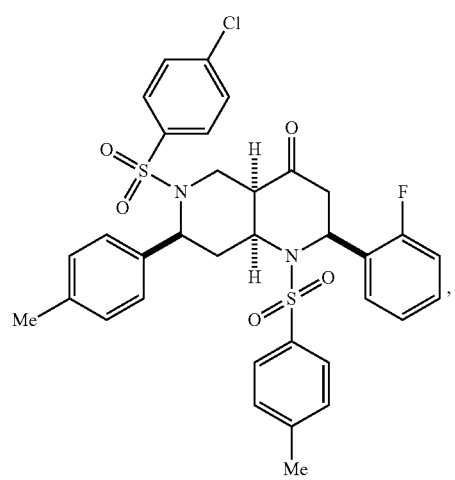

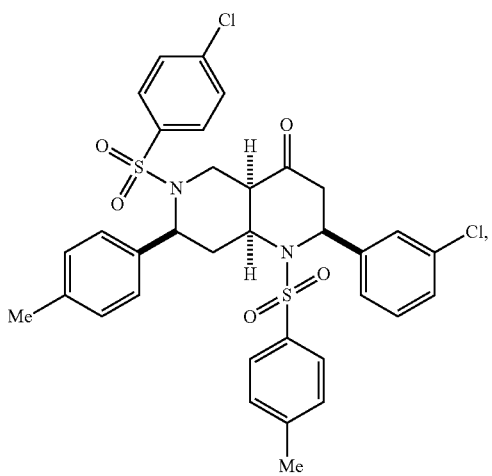

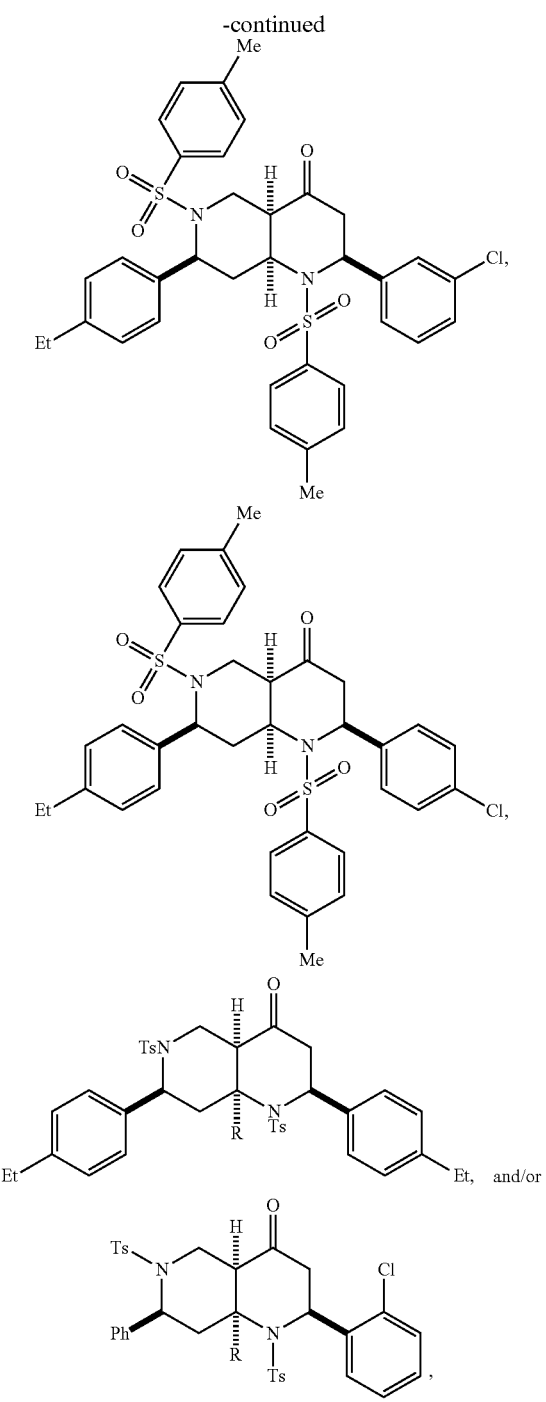

or pharmaceutically acceptable salt thereof.

2. A method of preparing the pharmaceutically acceptable pro-inflammatory composition of claim 1, comprising preparing the octahydro-1,6-naphthyridin-4-one compound or analog, wherein preparing the octahydro-1,6-naphthyridin-4-one compound or analog comprises:
- forming an enol ether intermediate via phosphine-catalyzed [4+2] annulation of an allenoate with a first imine building block followed by treatment with Tebbe reagent and anhydrous pyridine to form an enol ether intermediate,
- subjecting the enol ether intermediate to endo-selective Diels-Alder reaction with a second imine building block to yield an octahydro-1,6-naphthyridine intermediate, and
- forming the octahydro-1,6-naphthyridine-4-one compound or analog.

3. The method of claim 2, wherein the allenoate is formed by coupling a Wang resin having reactive hydroxyl groups with 2-methyl-2,3-butadienoic acid, and wherein the method is solid phase synthesis.

4. The method of claim 3, wherein the solid phase synthesis is carried out via combinatorial library construction.

5. The method of claim 4, wherein the solid support comprises Synphase lanterns wherein the first imine building block is encoded by tagging individual lanterns.

6. A pharmaceutically acceptable pro-inflammatory composition comprising a pharmaceutically acceptable carrier and an effective amount of one or more octahydro-1,6-naphthyridin-4-one analog represented by the formula 105A3-B2:

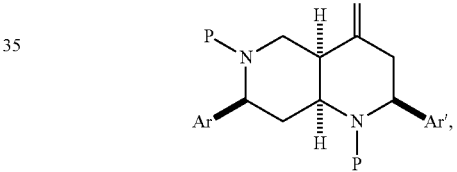

wherein:
Ar=phenyl, 4-MeC$_6$H$_4$, 4-EtC$_6$H$_4$, 4-ClC$_6$H$_4$, 3-ClC$_6$H$_4$, 2-thiophenyl, or 1-naphthyl;
P=tosyl, or benzenesulfonyl;
Ar'=phenyl, 4-EtC$_6$H$_4$, 4-ClC$_6$H$_4$, or 2-thiophenyl,
or a pharmaceutically acceptable salt thereof for augmenting innate immune responses in a mammal.

7. The pharmaceutically acceptable pro-inflammatory composition of claim 6, wherein:
Ar=4-EtC6H4;
P=tosyl; and
Ar'=4-EtC6H4,
or a pharmaceutically acceptable salt thereof.

* * * * *